United States Patent [19]

Shimizu et al.

[11] Patent Number: 4,474,754

[45] Date of Patent: Oct. 2, 1984

[54] HUMAN INTERFERON-RELATED PEPTIDES, ANTIGENS, ANTIBODIES AND PROCESS FOR PREPARING THE SAME

[75] Inventors: Fumio Shimizu; Yasukazu Ohmoto; Kenichi Imagawa, all of Tokushima, Japan

[73] Assignee: Otsuka Pharmaceutical Co., Ltd., Tokyo, Japan

[21] Appl. No.: 363,505

[22] Filed: Mar. 30, 1982

[30] Foreign Application Priority Data

| Mar. 31, 1981 | [JP] | Japan | 56-47840 |
| Jun. 30, 1981 | [JP] | Japan | 56-102731 |
| Aug. 24, 1981 | [JP] | Japan | 56-133124 |
| Aug. 24, 1981 | [JP] | Japan | 56-133127 |
| Aug. 24, 1981 | [JP] | Japan | 56-133128 |
| Aug. 24, 1981 | [JP] | Japan | 56-133129 |

[51] Int. Cl.$^3$ .................. A61K 39/395; A61K 45/02; C07O 7/00
[52] U.S. Cl. ................. 424/85; 260/112 R; 260/112.5 R
[58] Field of Search .................. 424/88, 85; 260/112.5 R, 112 R

[56] References Cited

U.S. PATENT DOCUMENTS

| 4,341,761 | 7/1982 | Ganfield et al. | 424/85 |
| 4,370,312 | 1/1983 | Jung et al. | 260/112.5 R |
| 4,376,760 | 3/1983 | Jung et al. | 260/112.5 R |

OTHER PUBLICATIONS

Abiko, T., et al., Chem. Pharm. Bull., vol. 29, pp. 1390–1397, 1981.
Levy et al., Proc. Natl. Acad. Sci., vol. 78, No. 10, pp. 6186–6190, 1981.
Zoon et al., J. Interferon Research, vol. 2, pp. 253–260, 1982.
Zoon et al., Science, vol. 207, pp. 527–528, 1980.
Knight et al., Science, vol. 207, pp. 525–526, 1980.

*Primary Examiner*—Blondel Hazel
*Attorney, Agent, or Firm*—Finnegan, Henderson, Farabow, Garrett & Dunner

[57] ABSTRACT

Human interferons related peptides and derivatives thereof, antigens, antibodies prepared therefrom, immobilized antibodies to be used for affinity chromatography, and novel method for assaying human interferons by using said affinity chromatography.

10 Claims, 10 Drawing Figures

HUMAN INTERFERON-RELATED PEPTIDES, ANTIGENS, ANTIBODIES AND PROCESS FOR PREPARING THE SAME

The present invention relates to human interferon-α and -β related peptides and derivatives thereof, process for preparing antigens and antibodies prepared by using said peptides, as well as immobilized said antibodies, used for affinity chromatography, and to novel method for assaying human interferon-α and -β.

In the present specification, amino acids, peptides, protecting groups active groups etc. are illustrated by abbreviations and symbols defined under the provisions of IUPAC (International Union of Pure and Applied Chemistry) and of IUB (International Union of Biochemistry, or by symbols commonly used in the art. In connection with optical isomers of amino acids, l-form (levo-form) of the isomers are generally mentioned unles otherwise noticed. Examples of such abbreviations and symbols are shown as follows:

Leu: Leucine
Ile: Isoleucine
Ala: Alanine
Gln: Glutamine
Thr: Threonine
His: Histidine
Ser: Serine
Gly: Glycine
Asn: Asparagine
Met: Methionine
Phe: Phenylalanine
Tyr: Tyrosine
Glu: Glutamic acid
Lys: Lysine
Arg: Arginine
Asp: Aspartic acid
Pro: Proline
OBzl: Benzyloxy group
NHS: N-Hydroxysuccinimido group
Z: Carbobenzoxy group
Su: Succinimido group
Tos: p-Toluenesulfonyl group
Boc: tert-Butoxycarbonyl group An interferon is a glycoprotein or a protein, having antiviral activity, which is released by cell in response to viral infection, and it is believed that diseases caused by viral infections can be prevented and cured by administering interferon, for this reason interferon has the attention in recent years.

Human interferons known today are classified into three types, i.e., interferon-α (Leucocytes interferon, Lymphoblastoid interferon), interferon-β (Fibroblast interferon) and interferon-γ (Immune interferon). However, there have not been developed any technology for purifying interferon to obtain the respective ingredients in the form of a single gycoprotein or protein.

Figure 1:
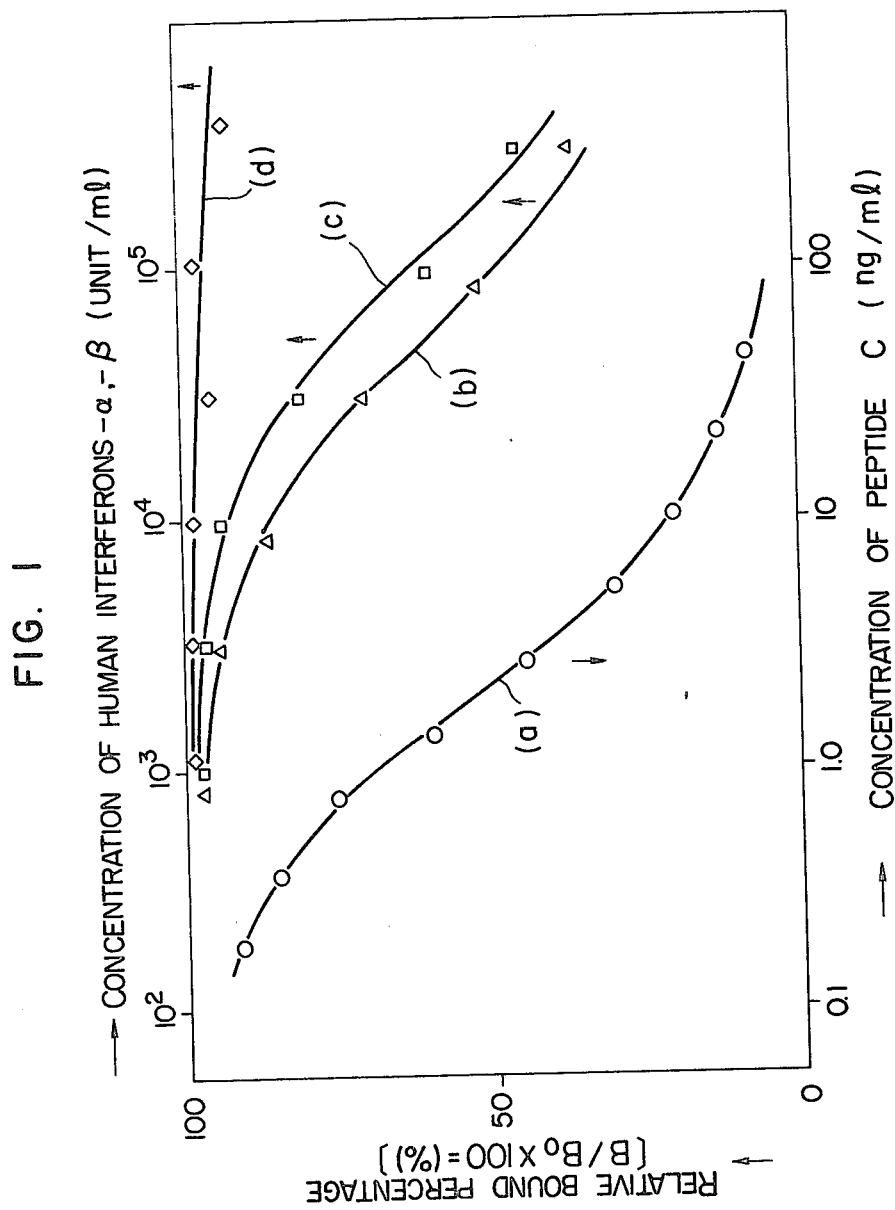
FIGS. 1 and 2 show curves indicating the specificity of the human interferon-α antibody obtained according to the present invention.

An object of the present invention is to provide novel antibodies which can be used for the technology in purifying and separating human interferon-α, especially, lymphoblastoid interferon, or human interferon-β.

Another object of the present invention is to provide antigens for preparing said antibodies.

Further object of the present invention is to provide a method for obtaining haptens suitable for preparing said antigens.

Yet, further object of the present invention is to provide a novel method for assaying human interferon-α and -β by using said antigens and antibodies.

As the results of extensive research works, the present inventors have found the facts that novel antigens of human interferon-α or -β can be prepared by using a novel N-terminal peptide or C-terminal peptide of human lymphoblastoid interferon, or by using a novel N-terminal peptide of human interferon-β, said novel N-terminal peptide and C-terminal peptide were newly synthesized by the present inventors; and novel antibodies having specificites to human interferon-α or -β can be prepared by using said antigens; further the objective human interferon-α or -β can be purified by an affinity chromatography in using said novel antibodies; and assay of human interferon-α or -β can be carried out by using said novel antigens and novel antibodies.

The present invention was completed by the above-mentioned newly found knowledges, thus according to the present invention, said antibodies having specificities to human interferon-α or -β, which are useful for purifying and for assaying the interferon can advantageously be prepared in an industrial scale by using the synthetic peptides which can easily be manufactured in large scale. Thus the present invention establishes new technologies in purification and assay system of human interferon-α and -β.

Novel synthetic peptide obtained by the present invention is a synthetic peptide selected from the group consisting of a peptide represented by the general formula (1),

$$R^1\text{-Leu-Ile-Leu-Leu-Ala-Gln-OH} \qquad (1)$$

[Wherein $R^1$ is a hydrogen atom, a group of the formula H-Thr-His-Ser-Leu-Gly-Asn-Arg-Arg-Ala-, a group of the formula H-Ser-Asp-Leu-Pro-Gln-Thr-His-Ser-Leu-Gly-Asn-Arg-Arg-Ala- or a group of the formula H-Tyr-Ser-Asp-Leu-Pro-Gln-Thr-His-Ser-Leu-Gly-Asn-Arg-Arg-Ala-]; a peptide represented by the general formula (2),

$$R^2\text{-Glu-Ser-Leu-Arg-Ser-Lys-Glu-OH} \qquad (2)$$

[wherein $R^2$ is a hydrogen atom, a group of the formula H-Thr-Asn-Leu-Gln-, a group of the formula H-Ser-Leu-Ser-Thr-Asn-Leu-Gln-, a group of the formula H-Tyr-Ser-Leu-Ser-Thr-Asn-Leu-Gln-]; and a peptide represented by the general formula (3),

$$R^3\text{-Leu-Gln-Arg-Ser-Ser-OH} \qquad (3)$$

[wherein R³ is a hydrogen atom, a group of the formula H-Phe-, a group of the formula H-Leu-Gly-Phe-, a group of the formula H-Tyr-Asn-Leu-Leu-Gly-Phe- or a group of the formula H-Met-Ser-Tyr-Asn-Leu-Leu-Gly-Phe-], thus said novel synthetic peptide is a peptide corresponding to N-terminal peptide of human lymphoblastoid interferon or derivative thereof [a peptide represented by the general formula (1)], a peptide corresponding to C-terminal peptide of human lymphoblastoid interferon or derivative thereof [a peptide represented by the general formula (2)] or a peptide corresponding to N-terminal peptide of human interferon-β or derivative thereof [a peptide represented by the general formula (3)].

Any one of the said synthetic peptides can easily be prepared by using amino acids which are commercially available and by a simple method. Said synthetic peptide has the specific amino acid arrangement, so that from a peptide represented by the general formula (1) or from a peptide represented by the general formula (2) an antigen having a clear cognition site for identifying human interferon-α, and from a peptide represented by the general formula (3) an antigen having a clear cognition site for identifying human interferon-β, as well as an antibody having high selectivity can be prepared in a large scale. Furthermore, an antibody having high specificity to human interferon-α or -β can be obtained more stably in a large scale by using the antigen prepared from the above-mentioned synthetic peptide as a hapten, than by using a natural interferon-α or interferon-β.

Novel synthetic peptide according to the present invention can be prepared by a method commonly used in synthesizing a peptide, specifically, for example, a method as described in "The Peptides", Volume 1, (1966), by Schröder and Luhke, Academic Press, New York, U.S.A., or in "PEPTIDE GOSEI" (Synthesis of peptide), by Izumiya et al., Maruzen and Co., Ltd. (1975). Such methods are exemplified as azide method, chloride method, acid anhydride method, mixed anhydride method, dicyclohexylcarbodiimide (DCC) method, active ester method (p-nitrophenyl ester method, N-hydroxysuccinimidoester method, cyanomethyl ester method and the like), a method using Woodward's reagent K, carbodiimidazole method, oxidation-reduction method, DDC/additive [N-hydroxy-5-norbornen-2,3-dicarboxyimide (HONB), 1-hydroxybenzotriazole (HOBt), N-hydroxysuccinimide (HOSu)] method and the like. In carrying out the above-mentioned methods, both solid phase synthetic method and liquid phase synthetic method can be applied, and the liquid phase synthetic method is preferred.

Novel synthetic peptide of the present invention is prepared by a conventional method for synthesizing a polypeptide as mentioned above, for example, by a so-called "stepwise", thus by condensing an amino acid step by step with the terminal amino acid in the peptide, or by coupling peptides divided into several fragments. More particularly, said peptide is prepared by condensing a starting material having reactive carboxyl group corresponding to one fragment being divided into two portions at the desired position, with another starting material having reactive amino group corresponding to another fragment by a method commonly used in peptide synthesis. When the condensed product thus obtained having protecting group, the desired peptide can be prepared by removing the protecting group by a common method. When using aspartic acid, lysine or arginine in the reaction step for preparing peptide of the present invention, said amino acid may preferably be protected by protecting group, in the final step of such case, generally the entire protecting groups are removed from the protected peptide in which at least one consitutional amino acid residual group is protected.

In reaction steps for synthesizing peptides of the present invention, any functional group which should not be related to the synthesizing reaction is generally protected with protecting group, and the protecting group is removed from the protected group after the reaction. Furthermore, a functional group participating to the reaction is generally activated. Methods for carrying out said reactions are known and reagents used for the reactions can be selected from those known in the art.

As to the protecting group for amino group, there are exemplified carbobenzoxy group, tert-butyloxycarbonyl group, tert-amyloxycarbonyl group, isobornyloxycarbonyl group, p-methoxybenzyloxycarbonyl group, 2-chlorobenzyloxycarbonyl group, adamantyloxycarbonyl group, trifluoroacetyl group, phthalyl group, formyl group, o-nitrophenylsulfenyl group, diphenylphosphinothioyl group and the like.

As to the protecting group for carboxyl group, there are exemplified an alkyl ester (such as an ester group of methyl, ethyl, propyl, butyl, tert-butyl or the like), a benzyl ester, a p-nitrobenzyl ester, a p-methoxybenzyl ester, a p-chlorobenzyl ester, a benzhydryl ester, carbobenzoxyhydrazide, tert-butyloxycarbonylhydrazide, tritylhydrazide and the like.

As to the protecting group for guanidino group of arginine, there are exemplified nitro group, tosyl group, p-methoxybenzenesulfonyl group, carbobenzoxy group, isobornyloxycarbonyl group, adamantyloxycarbonyl group and the like. Further, said guanidino group may be protected in the form of a salt, with a suitable acid, such as benzenesulfonic acid, toluenesulfonic acid, hydrochloric acid or sulfuric acid.

The hydroxy group of threonine and of serine may be protected by for example esterification or etherification, if necessary. As to the protecting group suitable for such esterification, there are exemplified a lower alkanoyl group such as acetyl group, an aroyl group such as benzoyl group, a group derived from carbonic acid such as benzoyloxycarbonyl group, ethyloxycarbonyl group and the like. As to the protecting group suitable for such etherification, there are exemplified benzyl group, tetrahydropyranyl group, tert-butyl group and the like.

Methionine may be protected in the form of sulfoxide.

As to the activated carboxyl group, a corresponding acid chloride, acid anhydride or mixed anhydride, azide, an activated ester (an ester of methyl alcohol, ethyl alcohol, benzyl alcohol, pentachlorophenol, p-nitrophenol, N-hydroxysuccinimide, N-hydroxybenzotriazole N-hydroxy-5-norbornen-2,3-dicarboxyimide and the like) and the like.

The peptide linkage formation reaction can be carried out in the presence of a condensing agent for example a carbodiimide reagent such as dicyclohexylcarbodiimide, carbodiimidazole or the like, or tetraethylpyrophosphite or the like.

Novel synthetic peptide of the present invention is prepared specifically by any one of the methods (A)-(C) as mentioned below:

Method A [Process for preparing a peptide represented by the general formula (1)]

A-(1): In case when R¹ is a hydrogen atom.

A—Ala—B    (2)
↓ H—Gln—OH    (3)

A—Ala—Gln—OH    (4)
↓
H—Ala—Gln—OH    (5)
↓ A—Leu—B    (6)

A—Leu—Ala—Gln—OH    (7)
↓
H—Leu—Ala—Gln—OH    (8)
↓ A—Leu—B    (6)

A—Leu—Leu—Ala—Gln—OH    (9)
↓
H—Leu—Leu—Ala—Gln—OH    (10)
↓ A—Ile—B    (11)

A—Ile—Leu—Leu—Ala—Gln—OH    (12)
↓
H—Ile—Leu—Leu—Ala—Gln—OH    (13)
↓ A—Leu—B    (6)

A—Leu—Ile—Leu—Leu—Ala—Gln—OH    (14)
↓
H—Leu—Ile—Leu—Leu—Ala—Gln—OH    (15)

A-(II): In case when R¹ is a group of the formula

H—Thr—His—Ser—Leu—Gln—Asn—Arg—Arg—Ala—.

Method A [Process for preparing a peptide represented by the general formula (1)]

```
         C
         |
A—Arg—B       (16)
    ↓ H—Ala—B   (17)

A—Arg—Ala—B    (18)
    ↓
    C
    |
H—Arg—Ala—B    (19)
    ↓   C
        |
      A—Arg—B   (16)

C   C
  |   |
A—Arg—Arg—Ala—B    (20)
    ↓
  C   C
  |   |
H—Arg—Arg—Ala—B    (21)
    ↓ A—Asn—B   (22)

C   C
        |   |
A—Asn—Arg—Arg—Ala—B    (23)
    ↓
A—Asn—Arg—Arg—Ala—B    (24)
    ↓ H—Leu—Ile—Leu—Leu—Ala—Gln—OH   (15)

A—Asn—Arg—Arg—Ala—Leu—Ile—Leu—Leu—Ala—Gln—OH    (25)
    ↓
H—Asn—Arg—Arg—Ala—Leu—Ile—Leu—Leu—Ala—Gln—OH    (26)
    ↓ ← (36)*

A—Thr—His—Ser—Leu—Gly—Asn—Arg—Arg—Ala—
Leu—Ile—Leu—Leu—Ala—Gln—OH    (27)
    ↓
H—Thr—His—Ser—Leu—Gly—Asn—Arg—Arg—Ala—
Leu—Ile—Leu—Leu—Ala—Gln—OH    (28)
```

[wherein (36)* is prepared by the following step,

-continued
Method A [Process for preparing a peptide represented by the general formula (1)]

A—Leu—B     (6)

↓ H—Gly—B     (29)

A—Leu—Gly—B     (30)

↓

H—Leu—Gly—B     (31)

↓ A—Ser—B     (32)

A—Ser—Leu—Gly—B     (33)

↓

H—Ser—Leu—Gly—B     (34)

↓ A—Thr—His—B     (35)

A—Thr—His—Ser—Leu—Gly—B     (36)*]

A-III: In case when R¹ is a group of the formula
H—Ser—Asp—Leu—Pro—Gln—Thr—His—Ser—Leu—Gly—Asn—Arg—Arg—Ala—.

A—Pro—B     (37)

↓ H—Gln—B     (38)

A—Pro—Gln—B     (39)

↓

H—Pro—Gln—B     (40)

↓ A—Leu—B     (6)

A—Leu—Pro—Gln—B     (41)

↓

H—Leu—Pro—Gln—B     (42)

↓ A—Asp—B     (43)

A—Asp—Leu—Pro—Gln—B     (44)

↓

D
|
A—Asp—Leu—Pro—Gln—B     (45)

↓

H—Asp—Leu—Pro—Gln—B     (46)

↓ A—Ser—B     (32)

-continued
Method A [Process for preparing a peptide represented by the general formula (1)]

A—Ser—Asp—Leu—Pro—Gln—B     (47)

↓ H—Thr—His—Ser—Leu—Gly—Asn—Arg—Arg—Ala—Leu—Ile—Leu—Leu—Ala—Gln—OH     (28)

A—Ser—Asp—Leu—Pro—Gln—Thr—His—Ser—Leu—Gln—Asn—Arg—Arg—Ala—Leu—Ile—Leu—Leu—Ala—Gln—OH     (48)

↓

H—Ser—Asp—Leu—Pro—Gln—Thr—His—Ser—Leu—Gln—Asn—Arg—Arg—Ala—Leu—Ile—Leu—Leu—Ala—Gln—OH     (49)

A-(IV): In case when R¹ is a group of the formula
H—Tyr—Ser—Asp—Leu—Pro—Gln—Thr—His—Ser—Leu—Gly—Asn—Arg—Arg—Ala—.

A—Ser—Asp—Leu—Pro—Gln—B     (47)

↓

H—Ser—Asp—Leu—Pro—Gln—B     (50)

↓ A—Tyr—B     (51)

A—Tyr—Ser—Asp—Leu—Pro—Gln—B     (52)

↓ H—Thr—His—Ser—Leu—Gly—Asn—Arg—Arg—Ala—Leu—Ile—Leu—Leu—Ala—Gln—OH     (28)

A—Tyr—Ser—Asp—Leu—Pro—Gln—Thr—His—Ser—Leu—Gly—Asn—Arg—Arg—Ala—Leu—Ile—Leu—Leu—Ala—Gln—OH     (53)

↓

H—Tyr—Ser—Asp—Leu—Pro—Gln—Thr—His—Ser—Leu—Gly—Asn—Arg—Arg—Ala—Leu—Ile—Leu—Leu—Ala—Gln—OH     (54)

[In the above-mentioned methods A-(I) to (IV), A is a protecting group for the amino group, B is a active group of the hydroxy group or of carboxyl group, C is a protecting group for the guanidino group of arginine, and D is a protecting group for aspartic acid.]

In the above-mentioned methods, as to a group of A, tert-butoxycarbonyl group (Boc), carbobenzoyl group (Z), p-methoxybenzyloxycarbonyl or the like is preferable; as to an active group of the carboxyl group represented by B, an active ester such as N-hydroxysuccinimido group, a mixed acid anhydride such as isobutyloxycarbonyl group, azide group, or the like is preferable, as to a group of C, nitro group, tosyl group or the like is preferable, as to a group of D, benzyloxy group or the like is preferably exemplified.

In the above-mentioned method A-(I), the reaction of an amino acid (2) with an amino acid (3) can be carried out in the presence of a solvent. As to the solvent, any solvent which can be used in a peptide condensation reaction can be used, for example, an hydrous or a water-containing dimethylformamide, dimethyl sulfoxide, pyridine, chloroform, dioxane, dichloromethane, tetrahydrofuran, ethyl acetate, N-methylpyrrolidone, hexamethylphosphoric triamide or a mixture of these solvents can be used.

The ratio of used amount of an amino acid (3) with an amino acid (2) is not specifically restricted and can be selected from a wide range, generally an equivalent to 5 times quantity, preferably an equivalent to 1.5 times quantity can be used.

The reaction temperature can be selected from a range used in a peptide linkage forming reaction, generally, at about −40° to about 60° C., preferably at about −20° to about 40° C. The reaction is generally carried out for several minutes to about 30 hours.

In the above-mentioned method A-(I), the reaction of a peptide (5) with an amino acid (6), the reaction of a peptide (8) with an amino acid (6), the reaction of a peptide (10) with an amino acid (11) and the reaction of a peptide (13) with an amino acid (6) can be carried out by a method similar to the reaction of an amino acid (2) with an amino acid (3).

In the above-mentioned method A-(II), the reaction of an amino acid (16) with an amino acid (17), the reaction of a peptide (19) with an amino acid (16), the reaction of a peptide (21) with an amino acid (22), the reaction of a peptide (24) with a peptide (15), the reaction of a peptide (26) with a peptide (36), the reaction of an amino acid (6) with an amino acid (29), the reaction of a peptide (31) with an amino acid (32) and the reaction of a peptide (34) with a peptide (35) may be carried out by a method similar to the reaction as mentioned above.

In the above-mentioned method A-(III), the reaction of an amino acid (37) with an amino acid (38), the reaction of a peptide (40) with an amino acid (6), the reaction of a peptide (42) with an amino acid (43), the reaction of a peptide (46) with an amino acid (32) and the reaction of a peptide (47) with a peptide (28); and in the above-mentioned method A-(IV), the reaction of a peptide (50) with an amino acid (51), and the reaction of a peptide (52) with a peptide (28) can also be carried out by a method similar to the reaction as mentioned above.

The removing reaction of the protecting group of A being captured respectively in peptides (4), (7), (9), (12), (14), (18), (20), (25), (27), (30), (33), (39), (41), (45), (47), (48) and (53) which are obtained by the above-mentioned reactions is carried out by any method commonly used in the art. As to the method of said removing reaction, there are exemplified reductive method (a hydrogenation by using palladium, palladium black or the like as a catalyst; a reduction by using sodium metal in liquid ammonia), acidolysis (acidolysis by using trifluoroacetic acid, hydrofluoric acid, methanesulfonic acid, hydrobromic acid or the like as a strong acid) and the like.

The above-mentioned hydrogenation by using a catalyst can be carried out under 1 atmospheric pressure of hydrogen, at 0° to 40° C. The catalyst is generally used in an amount of 100 mg to 1 g, and the reaction is generally completed in 1 to 48 hours.

The above-mentioned acidolysis is carried out in the absence of a solvent, at 0° to 30° C., preferably at 0° to 20° C., and the reaction is generally completed in 15 minutes to 1 hour. The acid may usually be used in 5 to 10 times quantity to the quantity of the starting material.

In the above-mentioned reduction by using sodium metal in liquid ammonia, sodium metal is used in an amount so as to keep the color of the reaction mixture in permanent blue for 30 seconds to 10 minutes. The reduction is usually carried out at −40° to −70° C.

The protecting group of C being captured in peptide (23) and the protecting group of D being captured in peptide (45) can also be removed by the above-mentioned reductive method.

Amino acids (2), (6), (11), (16), (22), (32), (37), (43) and (51) used in the above-mentioned methods A-(I) to A-(IV) may be of known commercially available products. Peptides (18), (23), (35), (36), (44), (47) and (52) used in the above-mentioned methods A-(I) to A-(IV) may also be of known commercially available products or those obtained by mixed anhydride method or by azide formation method. The mixed anhydride method is carried out in a suitable solvent in the presence of a basic compound by using an alkylhalocarboxylic acid. As to the alkylhalocarboxylic acid, there are exemplified methyl chloroformate, methyl bromoformate, ethyl chloroformate, ethyl bromoformate, isobutyl chloroformate and the like. As to the basic compound, there are exemplified organic basic compound, such as triethylamine, trimethylamine, pyridine, dimethylaniline, N-methylmorpholine, 1,5-diazabicyclo-[4,3,0]nonene-5 (DBN), 1,5-diazabicyclo[5,4,0]undecene-5 (DBU), 1,4-diazabicyclo[2,2,2]octane (DABCO) and the like; inorganic basic compounds, such as potassium carbonate, sodium carbonate, potassium hydrogencarbonate, sodium hydrogencarbonate and the like. As to the solvent used in this reaction can be selected from any solvent used in a mixed anhydride reaction, and there are exemplified halogenated hydrocarbons, such as methylene chloride, chloroform, dichloroethane and the like; aromatic hydrocarbons, such as benzene, toluene, xylene and the like; ethers, such as diethyl ether, tetrahydrofuran, dimethoxyethane and the like; esters, such as methyl acetate, ethyl acetate and the like; aprotic polor solvents, such as N,N-dimethylformamide, dimethyl sulfoxide, hexamethylphosphoric triamide and the like. The reaction is carried out at −20° to 100° C., preferably at −20° to 50° C., and is completed in generally 5 minutes to 10 hours, preferably in 5 minutes to 2 hours.

In the azide formation reaction, at first the carboxylic group is activated with an alcohol, such as methyl alcohol, ethyl alcohol, benzyl alcohol or the like, then the activated carboxyl group is reacted with hydrazine hydrate in a suitable solvent. As to the solvent, dioxane, dimethylformamide, dimethyl sulfoxide or a mixture of these solvents can be exemplified. Hydrazine hydrate may be used in generally 5 to 20 times molar quantity, preferably 5 to 10 times more quantity to the amount of the activated carboxylic group. The reaction is generally carried out at below 50° C., preferably at −20° to 30° C. Thus, a compound in which the carboxyl group of the terminal amino acid is substituted with hydrazine (hydrazine derivative) can be prepared. A compound in which the carboxyl group of the terminal amino acid is substituted with azide is prepared by reacting, in a suitable solvent, in the presence of an acid, the abovementioned hydrazine derivative with a nitrous acid compound. As to the acid, hydrochloric acid is generally used. As to the solvent, dioxane, dimethylformamide, dimethyl sulfoxide or a mixture of these solvents can be used. As to the nitrous acid compound, sodium nitrite, isoamyl nitrite, nitrosyl chloride or the like can be used. The nitrous acid compound is used in generally an equimolar to 2 times molar quantity, preferably an equimolar to 1.5 times molar quantity to the hydrozine derivative. The reaction is generally carried out at −20° to 0° C., preferably at −20° to −10° C., and is completed in about 5 to 10 minutes.

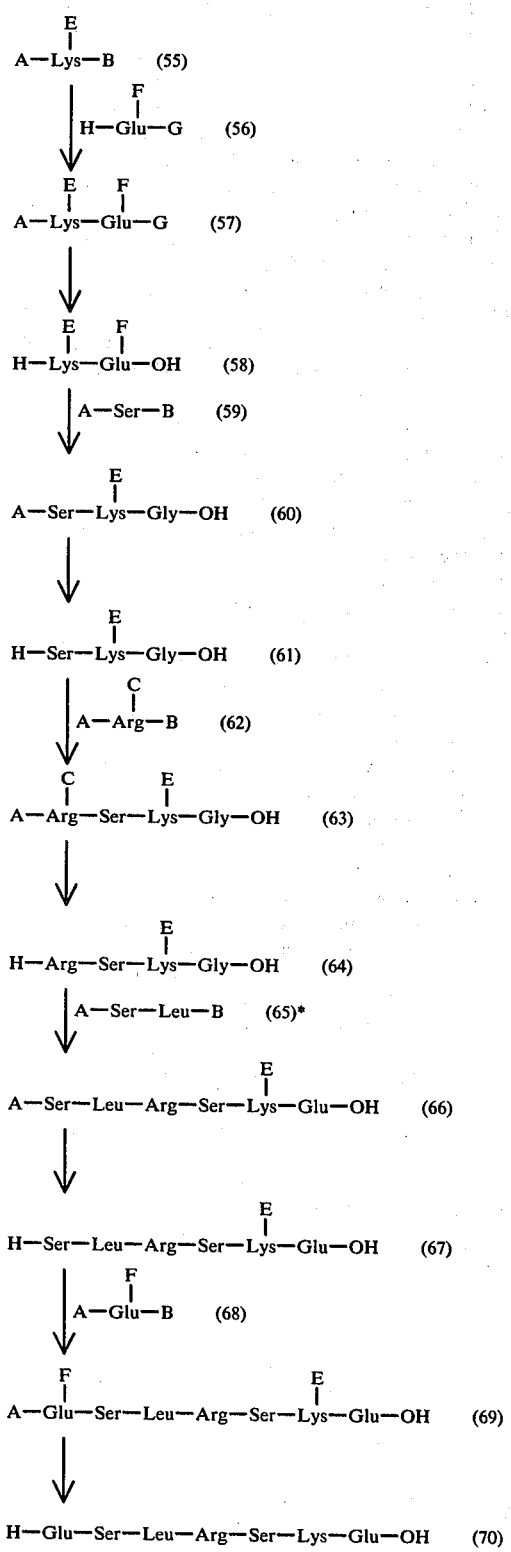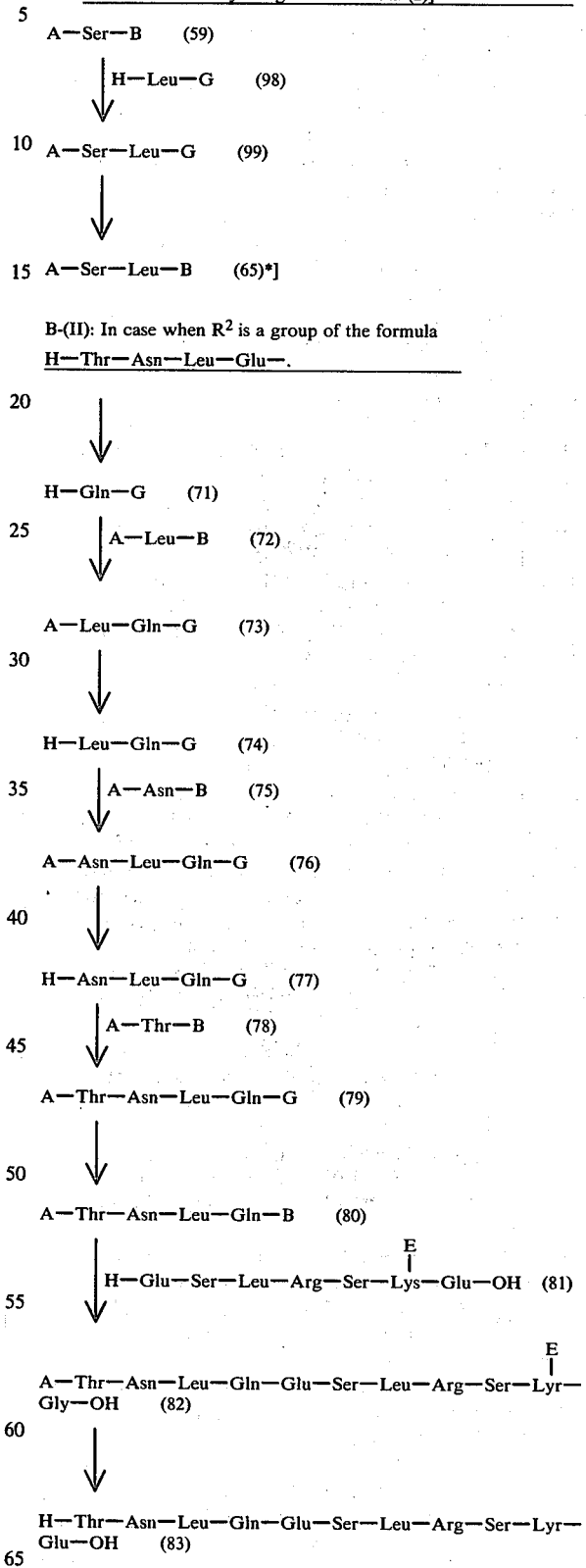

-continued
Method B [Process for preparing a peptide represented by the general formula (2)]

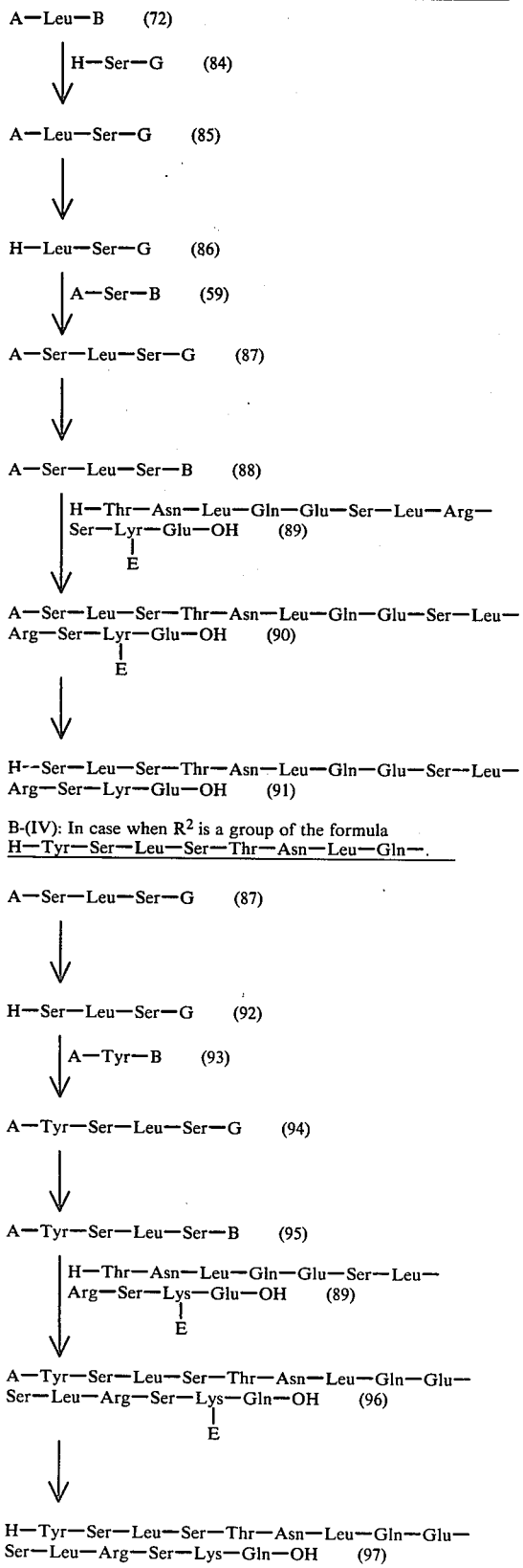

[In the above-mentioned methods B-(I) to (IV), E is a protecting group for ε-amino group of the lysine, F is a protecting group for γ-carboxyl group of the glutamic acid, and G is a protecting group for the carboxyl group, and A, B and C are the same as defined above.]

In the above-mentioned methods, as to a group of E, tosyl group or the like is preferable, as to a group of F, benzyloxy group or the like is preferable, and as to a group of G, an alkyl ester residual group, tert-butoxycarbonylhydrazide or the like is preferably exemplified.

In the above-mentioned method B-(I), the reaction of an amino acid (55) with an amino acid (56), the reaction of a peptide (58) with an amino acid (59), the reaction of a peptide (61) with an amino acid (62), the reaction of a peptide (64) with an amino acid (65), the reaction of a peptide (67) with an amino acid (68) and the reaction of an amino acid (59) with an amino acid (98); and in the above-mentioned method B-(II), the reaction of an amino acid (71) with an amino acid (72), the reaction of a peptide (74) with an amino acid (75), the reaction of a peptide (77) with an amino acid (78) and the reaction of a peptide (80) with a peptide (81); and in the above-mentioned method B-(III), the reaction of an amino acid (72) with an amino acid (84), the reaction of a peptide (86) with an amino acid (59) and the reaction of a peptide (88) with a peptide (89); and in the above-mentioned method B-(IV), the reaction of a peptide (92) with an amino acid (93) and the reaction of a peptide (95) with a peptide (89) can be carried out by a method similar to the reaction of an amino acid (2) with an amino acid (3) in the above-mention Method A.

The removing reaction of the protecting group of A or C being captured respectively in peptides among those obtained in the above-mentioned reactions can be carried out by a method similar to that explained in the above-mentioned method A. Furthermore, the removing reaction of the protecting group of E, F and G can be carried out by a method similar to the removing reaction of the protecting group of C as mentioned above.

Amino acids (55), (56), (59), (62), (68), (71), (72), (75), (78), (84), (93) and (98) used in the above-mentioned methods B-(I) to B-(IV) may be of known commercially available products. Peptide (69), (80), (88) and (95) used in the above-mentioned methods B-(I)~B-(IV) may also be of non-commercially available products or those obtained by mixed anhydride method or by azide method can also be used. Such methods have already been explained in the above-mentioned method A.

Peptide (81) used in the above-mentioned method B-(II) can be obtained by removing the protecting groups of A and F from peptide (69), and peptide (89) used in the above-mentioned method B-(III) can be obtained by removing the protecting group of A from peptide (82). The removing reaction of the protecting groups may be followed by the methods mentioned above.

Method C [Process for preparing a peptide represented by the general formula (3)]

C-(I): In case when $R^3$ is a hydrogen atom.

Method C [Process for preparing a peptide represented by the general formula (3)]

A—Leu—Gln—B   (101)*

↓ H—Arg(C)—Ser—Ser—OH   (102)

A—Leu—Gln—Arg(C)—Ser—Ser—OH   (103)

↓

H—Leu—Gln—Arg(C)—Ser—Ser—OH   (104)

[wherein the peptide (101)* is prepared by the following step,

A—Ser—B   (121)

↓ H—Ser—OR⁴   (122)

A—Ser—Ser—OR⁴   (123)

↓

H—Ser—Ser—OR⁴   (124)

↓ A—Arg(C)—B   (125)

A—Arg(C)—Ser—Ser—OR⁴   (126)

↓

A—Arg(C)—Ser—Ser—OH   (127)

↓

H—Arg(C)—Ser—Ser—OH   (101)*]

C-(II): In case when R³ is a group of the formula H—Phe—.

↓

H—Leu—Gln—Arg(C)—Ser—Ser—OH   (105)

↓ A—Phe—B   (106)

A—Phe—Leu—Gln—Arg(C)—Ser—Ser—OH   (107)

↓

H—Phe—Leu—Gln—Arg(C)—Ser—Ser—OH   (108)

C-(III): In case when R³ is a group of the formula H—Leu—Gly—Phe—.

↓

H—Phe—Leu—Gln—Arg(C)—Ser—Ser—OH   (109)

↓ A—Leu—Gly—B   (110)

A—Leu—Gly—Phe—Leu—Gln—Arg(C)—Ser—Ser—OH   (111)

↓

H—Leu—Gly—Phe—Leu—Gln—Arg(C)—Ser—Ser—OH   (112)

C-(IV): In case when R³ is a group of the formula H—Tyr—Asn—Leu—Gly—Phe—.

H—Leu—Gly—Phe—Leu—Gln—Arg(C)—Ser—Ser—OH   (113)

↓ A—Tyr—Asn—Leu—B   (114)*

A—Tyr—Asn—Leu—Gly—Phe—Leu—Gln—Arg(C)—Ser—Ser—OH   (115)

↓

H—Tyr—Asn—Leu—Leu—Gly—Phe—Leu—Gln—Arg(C)—Ser—Ser—OH   (116)

wherein the peptide (114)* is prepared by the following step,

A—Asn—B   (128)

↓ H—Leu—OR⁴   (129)

A—Asn—Leu—OR⁴   (130)

↓

H—Asn—Leu—OR⁴   (131)

↓ A—Tyr—B   (132)

A—Tyr—Asn—Leu—OR⁴   (133)

↓

A—Tyr—Asn—Leu—OH   (134)

↓

A—Tyr—Asn—Leu—B   (114)*]

C-(V): In case when R³ is a group of the formula H—Met—Ser—Tyr—Asn—Leu—Leu—Gly—Phe—.

-continued
Method C [Process for preparing a peptide represented by the general formula (3)]

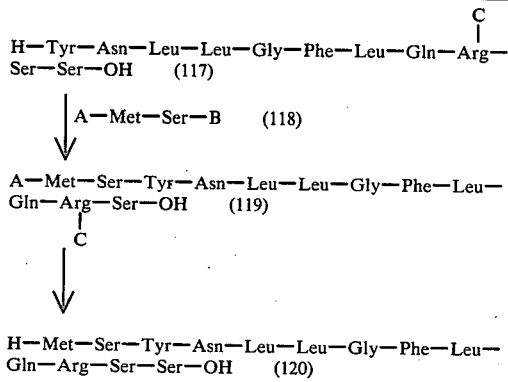

[In the above-mentioned methods C-(I) to (V), $R^4$ is a lower alkyl group; A, B and C are the same as defined above.]

In the above-mentioned, the reaction of a peptide (100) with a peptide (101), the reaction of a peptide (105) with an amino acid (106), the reaction of a peptide (109) with a peptide (110), the reaction of a peptide (113) with a peptide (114), the reaction of a peptide (117) with a peptide (118), the reaction of an amino acid (121) with an amino acid (122), the reaction of a peptide (124) with an amino acid (125), the reaction of an amino acid (128) with an amino acid (129) and the reaction of a peptide (131) with an amino acid (132) can be carried out by a method similar to the reaction of an amino acid (2) with an amino acid (3) in the above-mentioned method A.

The removal of the protecting group of A or C being captured in respective peptides among those obtained in the above-mentioned reaction can be carried out by a method similar to that explained in the above-mentioned method A.

The reaction for hydrolyzing a peptide (126) or (133) to obtain peptide (127) or (134) can be carried out in the presence of a mineral acid such as hydrochloric acid, sulfuric acid or the like, or an alkali such as sodium hydroxide, potassium hydroxide or the like, in a solvent such as methanol, ethanol, dioxane or the like. The reaction is generally carried out at 20° to 50° C., for about 30 minutes to 3 hours.

Peptide (105) used in the above-mentioned method C-(II) can be prepared by removing the protecting group of A from peptide (102). Similarly, peptide (109) used in the above-mentioned method C-(III) can be prepared by removing the protecting group of A from peptide (107), peptide (113) used in the above-mentioned method C-(IV) can be prepared by removing the protecting group of A from peptide (111), and peptide (117) used in the above-mentioned method C-(V) can be prepared by removing the protecting group of A from peptide (115). The removing reaction of the protecting groups may be carried out under a condition in the removing reaction as mentioned above.

As to preferable methods for obtaining peptide (114) from peptide (134), there are exemplified mixed acid anhydride method, azide formation method and the like as already explained in method A mentioned above.

The peptides of the present invention as prepared by the above-mentioned methods are isolated and purified from the reaction mixtures by common methods for isolating peptide, for example extraction, partition and column chromatography and the like.

As explained above, the synthetic peptides of the present invention, thus N-terminal peptide of human lymphoblastoid interferon, C-terminal peptide of human lymphoblastoid interferon, N-terminal peptide of human interferon-β and derivatives thereof are obtained.

Thus obtained synthetic peptides can be used as labelled antigens which used in radioimmunoassay (RIA) or fluorescence polarization immunoassay system, by introducing a common labelling agent for example a radioactive iodine such as $^{125}I$, $^{131}I$ or the like, a fluorochrome such as fluorescein isothiocyanate (FITC), tetramethylrhodamine isothiocyanate (TRITC), a substituted rhodamine isothiocyanate (XRITC), rhodamine B isothiocyanate, dichlorotriazinefluorescein (DTAF) or the like, or an enzyme or the like.

Introducing a radioactive iodine is carried out by treating a peptide having tyrosyl group among the synthetic peptides mentioned above by a common iodination method, for example an oxidative iodination method, using Chloramine T [cf. W. M. Hunter and F. C. Greenwood: Nature, 194, page 495 (1962); Biochem. J., 89, page 114, (1963)]. The above-mentioned iodination method is carried out in a suitable solvent for example 0.2M-phosphate buffer solution (pH=7.4), in the presence of Chloramine T at a room temperature for 10 to 30 seconds. The radioactive iodine may be used in an amount of about 1 millicurie per 1 nanomole of tyrosine molecule being contained in the peptide, together with 10 to 100 nanomoles of Chloramine T may be used, when one atom of the radioactive iodine is to be introduced into the tyrosine molucule. Similarly, when two atoms of the radioactive iodine is to be introduced into the tyrosine molecule, then 2 millicuries of the radioactive iodine may be used per 1 nanomole of tyrosine molecule being contained in the peptide, together with 10 to 100 nanomoles of Chloramine T may be used.

Thus prepared peptide being labelled with the radioactive iodine can be isolated and purified by a conventional method of isolation, for example, extraction, partition, column chromatography, dialysis or the like. If necessary, the labelled peptide can be stored in the form of lyophilized state.

The peptide being labelled with a fluorochrome is prepared by introducing the fluorochrome to the N-terminal or amino group in the molecule of the synthetic peptide, in a suitable buffer solution in an alkaline condition, preferably at pH 8 to 12. As to the buffer solution, there is not any specific restriction and can be selected from a wide range, as far as the pH value of the buffer solution is in the range as shown above. As to the buffer solutions, there are exemplified that a borate buffer solution, a bicarbonate buffer solution, a glycine buffer solution, a Barbital buffer solution, a tris buffer solution, an ammediol buffer solution, Ringer's buffer solution and the like can be used. In case that the peptide and/or fluorochrome is not soluble in the buffer solution, the labelling reaction can be carried out by adding a common solvent, for example methanol, ethanol, acetone, dimethylformamide or the like, into the reaction system.

The labelling reaction is generally proceeded at about 0° to 40° C., preferably, at 0° to 20° C., and is completed in a several minutes to about 48 hours.

There is not any restriction to the ratio of amount of fluorochrome and can be selected from a wide range, and generally 1 to 10 times molar quantity, preferably to 2 to 4 times molar quantity of the fluorochrome may be used per one amino group being contained in the peptide. Thus obtained peptide being labelled with a fluorochrome can be isolated and purified and to be stored as in the case similar to the peptide labelled with the radioactive iodine.

Hitherto, interferons are assayed indirectly by biological measuring methods on the basis of physiological activities thereof [Finter, N. B. in Interferon and Interferon Inducers (edited by Finter, N. B.), pages 135-170 (North-Holland, Amsterdam, 1973)]. Thus, the biological measuring method requires living cells and living virus which can be able to infect to said cells, and potency of the interferons are assayed by determining, directly or indirectly, the degrees of cell death caused by the virus infection. However, such biological measuring method gives unstable and scattering result because the materials used in the method are living organisms. Additionally, if any substance having antiviral activity other than the interferons to be assayed is contained in the test sample, then such biological measuring method for assaying interferons becomes meaningless. Further, selective assay of human interferon-α or human interferon-β cannot be made by such biological measuring method. Yet, further such biological measuring method requires several days to obtain the results with too complicated operations, therefore such method can not meet the requirements of the medical world.

Different form such biological measuring method, novel method for assaying human interferons of the present invention, according to radioimmunoassay method (RIA method) or fluorescence polarization immunoassay system by using the labelled antigens (labelled peptides) can be able to assay human interferon-α or human interferon-β selectively, simply, quickly and with high accuracy.

Hitherto, a fluorescence polarization immunoassay method is well known, however, there have not been known that this method have been applied for qualitative determination of interferons. This is because that a purified interferon labelled with fluorochrome was hardly be prepared, and even if said purified interferon labelled with fluorochrome could be obtained, such labelled substance having large molecular weight can only show less changes in polarizing degree (P value), thus an adequate sensitivity in qualitative determination could not be obtained.

On the contrary to the above, the peptides labelled with fluorochrome of the present invention can show a large changes in polarizing degree (P value) and are useful labelled substances for assaying human interferon-α or human interferon-β with an adequate accuracy in qualitative determination. According to the developments of such peptides labelled with fluorochrome, qualitative determination of human interferon-α or human interferon-β by applying the above-mentioned fluorescence polarization immunoassay system can actually be made.

Method for assaying interferons by fluorescence polarization immunoassay is explained in detail as follows.

Sequence of measuring procedures and operations are not basically different from those used in a common method of fluorescence polarization immunoassay system.

The method for assaying interferons according to the present invention can be carried out by using the standard antigen, and the antibody thereagainst as well as the peptide labellled with fluorochrome. As to the standard antigen, a native human interferon-α itself or a native human interferon-β itself, or a peptide represented by the general formula (1) to (3), having antigenicity equivalent to the human interferon-α or -β, can be used. In case of using said peptide, potency of interferon of unknown sample can easily be calculated by knowing the cross-reactivity of human interferon-α or -β and the peptide against the antibody, before the test. Considering that, efforts, costs and operations for obtaining a purified product of the standard antigen, the use of the peptide is quite advantage.

As to the antibody of interferon used in the assay method according to the present invention, any antibody against human interferon-α or -β or a peptide represented by the general formulas (1) to (3) can be used, and preferably, as explained later, an antibody having high specificity against human interferon-α or -β which is prepared by using the peptide represented by general formulas (1) to (3) as the hapten.

As to the sequence of measuring procedures, at first a series of diluted samples of the standard antigen is prepared by diluting the antigen with a suitable diluting solution. As to the diluting solution, there is not any restriction thereto and any type of diluting solution suitable for this type of method can be used. Specifically, a buffer solution having pH value of 5 to 10, preferably, pH value of 7 to 8 for example, a borate buffer solution, a tris-HCl buffer solution, a phosphate buffer solution, an acetic acid buffer solution, a citric acid-phosphoric acid buffer solution, a glycine buffer solution or the like can be used. Additionally, for inhibiting adsorption, such as bovine serum albumin (BSA), sodium azide, as a preservitive, and a common aditive such as EDTA, sodium chloride or the like can be added into the diluting solution.

Next, predetermined amount of the antibody and predetermined amount of the peptide labelled with a fluorochrome were added to the respective samples of the series of diluted standard antigen to prepare samples, then said samples are allowed to stand at 0° to 37° C. for 30 minutes to 48 hours, and the strength of vertical polarized fluorescence ($I_{VS}$) and the strength of horizontal polarized fluorescence ($I_{HS}$) are measured by a common method. Measurements of said polarized fluorescene can easily be conducted by using a common apparatus for measuring strength of polarized light, for example a commercially available "FS-501" (manufactured by Union-Giken-Sha, Co., Ltd.).

By a procedure similar to that explained above in preparing the series of diluted standard antigen samples, a series of reference samples without containing the peptide labelled with a fluorochrome are prepared, and the strength of vertical polarized fluorescence ($I_{VR}$) and the strength of horizontal polarized fluorescence ($I_{HR}$) are measured.

Then, a standard curve of the polarizing degree (P value) versus the concentration of samples in the series of diluted standard antigen is obtained. The polarizing degree (P value) is calculated by the following formula, $$P = \frac{(I_{VS} - I_{HS}) - (I_{HS} - I_{HR})}{(I_{VS} - I_{VR}) + (I_{HS} - I_{HR})} \times 100\ (\%)$$

In place of the standard antigen samples, by using samples containing human interferon-α or -β of unknown concentration, human interferon-α or -β contained in the samples can be assayed from the standard curve by calculating the P value obtained similarly.

In case that a native human interferon-α or -β is used as the standard antigen, the potency of the interferon in the sample can be obtained from the standard curve.

In case that a peptide represented by the general formulas (1) to (3) is used as the standard antigen, the cross-reactivity of human interferon-α or -β and the peptide against the antibody is obtained before the test, then converting into the potency of the interferon.

The synthetic peptides of the present invention can be applied as haptens for preparing human interferon-α or -β antigen.

Method for preparing human interferon-α or -β antigen is now explained as follows.

Thus, the human interferon-α or -β antigen is prepared by reacting at least a synthetic peptide used as the hapten with a carrier in the presence of a hapten-carrier bonding reagent.

As to the carrier to be bonded to the hapten used in the above-mentioned method, a natural or synthetic protein having high molecular weight commonly used in preparation of a common antigen may be used, for example animal serum albumins such as equine serum albumin, bovine serum albumin, rabbit serum albumin, human serum albumin, ovine serum albumin and the like; animal serum globulins such as equine serum globulin, bovin serum globulin, rabbit serum globulin, human serum globulin, ovine serum globulin and the like; animal thyroglobulins such as equine thyroglobulin, bovine thyroglobulin, rabbit thyroglobulin, human thyroglobulin, ovine thyroglobulin and the like; animal hemoglobulin sach as equine hemoglobulin, bovine hemoglobulin, rabbit hemoglobulin, human hemoglobulin, ovine hemoglobulin and the like; animal hemocyanins; proteins extracted from ascaris [ascaris extracts themselves as disclosed in Japanese Patent Kokai (Laid-open) No. Sho-16414/1981, J. Immun., 111, 260-268 (1973); J. Immun., 122, 302-308 (1979); J. Immun., 98, 893-900 (1967) and Am. J. Physiol., 199, 575-578 (1960), or products obtained therefrom by further purification]; a polylysine, a polyglutaminic acid, a lysine-glutaminic acid co-polymer, a copolymer containing lysine or ornitine and the like.

As to the hapten-carrier bonding reagent, those of conventionally used in preparing common antigen can be selected from wide range, specifically, aliphtic dialdehydes such as glyoxal, malondialdeyde, glutaraldehyde, succinaldehyde, adipoaldehyde and the like those of which can make crosslinked bond between two amino groups; dimaleimide compounds such as N,N'-o-phenylenedimaleimide, N,N'-m-phenylenedimaleimide and the like, those of which can make crosslinked bond between two thiol groups; maleimidocarboxyl-N-hydroxysuccinimidoester compounds such as metamaleimidobenzoyl-N-hydroxysuccinimidoester, 4-(maleimidomethyl)-cyclohexane-1-carboxyl-N'-hydroxysuccinimidoester and the like, those of which can make crosslinked bond between amino group and thiol group; dehydrocondensing agents such as N,N-dicyclohexylcarbodiimide (DCC), N-ethyl-N'-dimethylaminocarbodiimide, 1-ethyl-3-diisopropylaminocarbodiimide, 1-cyclohexyl-3-(2-morpholinyl-4-ethyl)carbodiimide and the like, those of which used for a common peptide bonding formation reaction, such as for combining amino group with carboxyl group; further diazonium aryl-carboxylic acids such as p-diazonium phenylacetic acid and the like may be used in combination with a common peptide bonding formation reagent for example the above-mentioned dehydrocondensing agent.

Reaction for preparing antigens of the present invention is carried out for example in an aqueous solution or a common buffer solution having a pH value of 7 to 10, preferably, pH value of 8 to 9, at 0° to 40° C., preferably, at a room temperature, generally 1-24 hours, preferably 3-5 hours. As to the typical buffer solutions used in the reaction, there are exemplified as follows:

0.2N-sodium hyroxide—0.2M-boric acid—0.2M-potassium chloride buffer solution, 0.2M-sodium carbonate—0.2M-boric acid—0.2M-potassium chloride buffer solution, 0.05M-sodium tetraborate—0.2M-boric acid—0.05 M-sodium chloride buffer solution, 0.1M-potassium dihydrophosphate—0.05M-sodium tetraborate buffer solution In the above-mentioned reaction, the ratio of amounts of a hapten, a hapten-carrier bonding agent and a carrier may properly determined, and generally, 2 to 6 times the quantity by weight, preferably 3 to 5 times the quantity by weight of the carrier is used to the hapten, and 5 to 10 times molar quantity of the hapten-carrier bonding agent is used to the hapten. According to the above-mentioned reaction, a human interferon-α or -β antigen consisting of a carrier and a hapten both of which are combined through a hapten-carrier bonding agent can be obtained.

After the reaction is completed, the antigen thus obtained can be isolated and purified easily by a common dialysis method, gel filtration method, fractional precipitation method and the like. Further, the antigen may be stored in a conventional lyophilized form.

Thus, the human interferon-α or -β antigen composition consisting of one of the present synthetic peptide and the carrier is obtained. Said antigen is a composition in which generally an average 5 to 20 moles of the peptides are combined with one mole of the protein, from said antigen an antibody having high specificity to human interferon-α or -β can be prepared with good repeatability. Especially, among the antigen compositions, one having the bonding ratio of protein:peptide=1:8 to 1:15 shows higher specificity and is most preferable, since from which an antibody having high potency with high sensitivity can be prepared.

Preparation of the antibody by using the antigen obtained as above is carried out as follows. Thus the said antigen is administered to a mammal and an antibody being produced in the mammal body is collected.

There is not any specific restriction in selecting the mammal to be used in preparing the antibody, and generally, rabbit or guinea pig is used preferably. In producing the antibody, the predetermined amount of the antigen obtained as above is diluted with a physiological saline solution into a suitable concentration, and this diluted solution is further diluted by mixing with a complete Freund's adjuvant to prepare a suspension, then the suspension is administered to a mammal. For example, said suspension is administered intracutaneously to a rabbit in an amount of 0.5 to 5 mg of the antigen in every administration, and the administrations are continued every other weeks for 2 to 10 months, preferably for 4 to 6 month to make immunization. For collecting the antibody, the blood is taken out from the immunized animal at the time when a large amount of the antibody is produced in the animal body after the administration of the suspension, generally 1 to 2 weeks after the last administration of the suspension. The blood taken out from the animal is treated by centrifugal separation to separate the serum to obtain the antibody. According to a method of the present invention, on the basis of the specific properties of the antigen, an antibody having excellent specificity to human interferon-α or -β with high potency and high sensitivity can be obtained.

Thus obtained antibody of the present invention has an excellent specificity to human interferon-α or -β and is useful since it can be able to assay human interferon-α or -β in RIA method with high accuracy. Further, the antibody can be used in an enzyme immunoassay (EIA) method, a fluorescence immunoassay (FIA) or the like by labelling the antibody with an enzyme or with a fluorochrome. Yet further, the antibody can be used as the starting material for preparing an adsorbent to be used in an affinity chromatography by immobillizing the antibody on a suitable insoluble carrier.

By using the adsorbent for said affinity chromatography, human interferon-α or -β can be isolated and purified from a crude product of interferons by the selection of type of the antibody to be used. Thus, when the adsorbent in which human interferon-α antibody is immobillized is used, then human interferon-α is selectively adsorbed thereon, similarly to the above, when the adsorbent in which human interferon-β antibody is immobillized is used, then human interferon-β is selectively adsorbed thereon. Next, from the adsorbent containing the human interferon-α or -β being adsorbed thereon, desorption of the human interferon-α or -β can be carried out under a mild condition by simple operation, therefore high purity of human interferon-α or -β can be obtained qualitatively without losing the activity thereof.

The adsorbent for an affinity chromatography can be prepared by a method mentioned below.

In immobillizing the human interferon antibody on an insoluble carrier, any conventional method for immobillizing a bio-material can be applied, among of such conventional methods, the use of cyanogen bromide-activated-polysaccharide method is preferable. The cyanogen bromide-activated-polysaccharide method is first treating an insoluble carrier with cyanogen bromide, then thus obtained activated carrier is coupling with a bio-substrate under a mild condition to immbobillize the bio-substance. In treating the insoluble carrier with cyanogen bromide, the treatment may be carried out at pH 11-12 by using a basic compound for example sodium hydroxide, sodium hydrogen-carbonate or the like, at a room temperature in a solvent for example water, acetonitrile or the like, for about 1 to 12 minutes. Ratio of the amount of cyanogen bromide to the amount of the insoluble carrier may be generally an equivalent quantity by weight. As to the insoluble carrier, any known insoluble carrier having low non-specific adsorpability to general bio-substance, having high porosity, having functional groups which can be able to immobillize bio-substance under a mild condition, as well as sufficiently stable chemically and physically, may be used. For example, cellulose type carrier such as aminoethyl cellulose, carboxymethylcellulose, bromoacetylcellulose, p-anilinocellulose and the like; crosslinked dextran type carrier such as Sephadex, CM-Sephadex (manufactured by Pharmacia Fine Chemicals, Inc.) and the like; agarose type carrier such as Sepharose 2B, Sepharose 4B, Sepharose 6B (manufactured by Pharmacia Fine Chemicals, Inc.) and the like may be used.

In coupling thus obtained cyanogen bromide-activated carrier with the human interferon antibody, 30 to 80 times the quantity by weight of a cyanogen bromide-activated carrier may be reacted with a human interferon antibody in a suitable solvent such as 0.1M-sodium hydrogencarbonate aqueous solution (containing 0.5M- of sodium chloride, pH=8.4), at generally 0° to 40° C., preferably at 2° to 8° C., for about 10 to 20 hours. An adsorbent for an affinity chromatography of the present invention thus prepared. Said adsorbent may be stored in a suitable solvent, for example in a physiological saline solution.

For the purpose of to explain the present invention in detail, examples of preparations for peptides of the present invention, antigens and antibodies obtained therefrom, however, are described the present invention is not restricted only to these examples.

In the following examples of preparation, the Rf value is determined by using the following mixed solvents to a thin-layer-chromatography on a silica gel, $Rf^I$ ... 1-butanol-acetic acid-water (4:1:5)
$Rf^{II}$ ... 1-butanol-pyridine-acetic acid-water (15:10:3:12)

[Synthesis of peptides]

PREPARATIVE EXAMPLE A-1

1. Preparation of Z-Ala-Gln-OH

To a solution of 4.80 g of Z-Ala-OSu in 60 ml of tetrahydrofuran was added a solution of 2.19 g of H-Gln-OH in 40 ml of water and 2.10 ml of triethylamine and the mixture was stirred at a room temperature for 20 hours. Tetrahydrofuran and water were removed by distillation and the residue thus obtained was extracted with n-butanol. The n-butanol extract was washed with a 2%-acetic acid and butanol was removed by distillation. The precipitated substance thus obtained was collected by filtration and reprecipitated with methanol-ethyl acetate to obtain 3.87 g of Z-Ala-Gln-OH.

$Rf^I$: 0.41
$Rf^{II}$: 0.56

Elemental analysis (for $C_{16}H_{21}N_3O_6$): Calculated (%): C 54.69, H 6.02, N 11.96. Found (%): C 54.50, H 6.31, N 11.62.

2(a). Preparation of H-Ala-Gln-OH 3.50 Grams of Z-Ala-Gln-OH was dissolved in 50 ml of water and 30 ml of methanol, and the mixture was catalytically reduced by using palladium as a catalyst to obtain H-Ala-Gln-OH.

$Rf^I$: 0.04

2(b). Preparation of Z-Leu-Ala-Gln-OH 3.97 Grams of Z-Leu-OSu, the H-Ala-Gln-OH obtained in the above-mentioned 2(a) and 1.39 ml of triethylamine were dissolved in 50 ml of dimethylformamide and the mixture was stirred at a room temperature for 20 hours. Dimethylformamide was removed by distillation, the residue thus obtained was extracted with ethyl acetate. The extract was washed with 1N-citric acid three times and with water 5 times. Ethyl acetate was removed by distillation, and to the reside was added ether, the precipitate formed was collected by filtration and dried, then reprecipitated with methanol-ethyl acetate to obtain 2.15 g of Z-Leu-Ala-Gln-OH.

$Rf^I$: 0.49

Rf$^{II}$: 0.62

Elemental analysis (for $C_{22}H_{32}N_4O_7$): Calculated (%): C 56.88, H 6.94, N 12.06. Found (%): C 56.41, H 6.80, N 12.18.

3(a). Preparation of H-Leu-Ala-Gln-OH

To 2.10 g of Z-Leu-Ala-Gln-OH was added 20 ml of acetic acid solution containing 25% of hydrogen bromide, then the mixture was allowed to stand at a room temperature for 1 hour. After the completion of the reaction, dried ether was added to the reaction mixture to obtain H-Leu-Ala-Gln-OH.

Rf$^I$: 0.10

3(b). Preparation of H-Leu-Leu-Ala-Gln-OH 1.96 Grms of Z-Leu-OSu, 0.63 ml of triethylamine and H-Leu-Ala-Gln-OH obtained above step of 3(a) were dissolved in 50 ml of dimethylformamide, and stirred at a room temperature for 20 hours. After removal of dimethylformamide by distillation, 1M-citric acid was added to the residue, and crystals being precipitated were collected by filtration. The crystals were washed with water until the filtrate become neutral, then dried. The dried crystals were washed with methanol-ethyl acetate to obtain 1.63 g of Z-Leu-Leu-Ala-Gln-OH.

Rf$^I$: 0.58
Rf$^{II}$: 0.64

Elemental analysis (for $C_{28}H_{43}N_5O_8$): Calculated (%): C 58.22, H 7.50, N 12.12. Found (%): C 57.85, H 7.90, N 11.96.

4(a). Preparation of H-Leu-Leu-Ala-Gln-OH

To 1.50 g of Z-Leu-Leu-Ala-Gln-OH was added 20 ml of acetic acid containing 25% of hydrogen bromide, then the mixture was stirred at a room temperature for 1 hour. To the reaction mixture was added dried ether, and solid material precipitated was collected by filtration to obtain H-Leu-Leu-Ala-Gln-OH.

Rf$^I$: 0.19

4(b). Preparation of Z-Ile-Leu-Leu-Ala-Gln-OH 1.41 Grams of Z-Ile-OSu, the above-obtained H-Leu-Leu-Ala-Gln-OH and 0.36 ml of triethylamine were dissolved in 50 ml of dimethylformamide, then the mixture was stirred at a room temperature for 20 hours. After removal of dimethylformamide by distillation, 1N-citric acid was added to the residue, and crystals being precipitated were collected by filtration and washed with hot methanol to obtain 1.17 g of Z-Ile-Leu-Leu-Ala-Gln-OH.

Rf$^I$: 0.61
Rf$^{II}$: 0.71

Elemental analysis (for $C_{34}H_{54}N_6O_9$): Calculated (%): C 59.11, H 7.87, N 12.16. Found (%): C 59.23, H 7.80, N 12.02.

5(a). Preparation of H-Ile-Leu-Leu-Ala-Gln-OH

To 1.10 g of Z-Ile-Leu-Leu-Ala-Gln-OH was added 15 ml of acetic acid solution containing 25% of hydrogen bromide, then the mixture was stirred at a room temperature for 1 hour. After completion of the reaction, dried ether was added to the reaction mixture to obtain H-Ile-Leu-Leu-Ala-Gln-OH.

Rf$^I$: 0.25

5(b). Preparation of Z-Leu-Ile-Leu-Leu-Ala-Gln-OH 0.69 Gram of Z-Leu-OSu, the above-obtained H-Ile-Leu-Leu-Ala-Gln-OH and 0.22 ml of triethylamine were dissolved in 50 ml of dimethylformamide, and the mixture was stirred at a room temperature for 20 hours. After removal of dimethylformamide by distillation, 1N-succinic acid was added to the residue, the precipitated material was collected by filtration and washed with water until the filtrate become neutral and then dried. The dried material was washed with hot methanol to obtain 1.10 g of Z-Leu-Ile-Leu-Leu-Ala-Gln-OH.

Rf$^I$: 0.58
Rf$^{II}$: 0.71

Elemental analysis (for $C_{40}H_{65}N_7O_{10}$): Calculated (%): C 59.75, H 8.15, N 12.19. Found (%): C 59.60, H 8.02, N 11.92.

6. Preparation of H-Leu-Ile-Leu-Leu-Ala-Gln-OH 0.50 Gram of Z-Leu-Ile-Leu-Leu-Ala-Gln-OH was dissolved in 50 ml of methanol and 10 ml of 10%-acetic acid, and the mixture was catalytically reduced by using palladium as a catalyst to obtain H-Leu-Ile-Leu-Leu-Ala-Gln-OH. Hereinafter, this product is referred to as [Peptide A].

Rf$^I$: 0.23
Rf$^{II}$: 0.61

Elemental analysis (for $C_{32}H_{59}N_7O_8 \cdot 2H_2O$): Calculated (%): C 54.45, H 8.99, N 13.89. Found (%): C 54.30, H 8.81, N 13.98.

PREPARATIVE EXAMPLE A-2

1. Preparation of Boc-Ala-NHNHZ 4.99 Grams of Boc-Ala-OH, 4.36 g of $NH_2$-NH-Z and 5.44 g of dicyclohexylcarbodiimide were dissolved in 150 ml of tetrahydrofuran, and the mixture was stirred at 4° C. for 20 hours. The solid material formed in the reaction mixture was removed by filtration, and remaining filtrate was allowed to distillation, to the residue thus obtained was added ether to obtain precipitate. Said precipitate was collected by filtration and reprecipitated from ether and petroleum ether to obtain 7.03 g of Boc-Ala-NHNHZ.

Rf$^I$: 0.79
Rf$^{II}$: 0.81

Elemental analysis (for $C_{16}H_{23}N_3O_5$): Calculated (%): C 56.96, H 6.87, N 12.45. Found (%): C 56.81, H 6.49, N 12.34.

2(a). Preparation of H-Ala-NHNHZ 3.00 Grams of Boc-Ala-NHNHZ was dissolved in 10 ml of trifluoroacetic acid, and allowed to stand at a room temperature for 15 minutes, then trifluoroacetic acid was removed by distillation and dried to obtain H-Ala-NHNHZ.

Rf$^{II}$: 0.51

2(b). Preparation of Boc-Arg(NO$_2$)-Ala-NHNHZ 2.84 Grams of Boc-Arg(NO$_2$)-OH was dissolved in 40 ml of a tetrahydrofuran solution containing 0.91 ml of N-methylmorpholine, and the mixture was cooled to −15° C., then 1.17 ml of isobutyl chloroformate and was stirred vigorously for 30 seconds. To the reaction mixture were added a solution of H-Ala-NHNHZ in 20 ml of a dimethylformamide and 1.24 ml of triethylamine and stirred for 1 minute. The reaction mixture was allowed to stand at 0° C. for 5 minutes, then warmed at 40° C. for 2 minutes, then stirred at a room temperature for 15 minutes. After removal of tetrahydrofuran and dimethylformamide by distillation, the residue thus obtained was extracted with ethyl acetate. The extract was washed with 1N-citric acid, then with a saturated sodium hydrogencarbonate solution, next with a saturated sodium chloride solution. After removal of ethyl acetate by distillation, reprecipitated from ethyl acetate-ether to obtain 3.70 g of BOC-Arg(NO$_2$)-Ala-NHNHZ.

Rf$^I$: 0.68
Rf$^{II}$: 0.79

Elemental analysis (for C$_{22}$H$_{34}$N$_8$O$_8$): Calculated (%): C 49.06, H 6.36, N 20.80. Found (%): C 49.40, H 6.72, N 20.43.

3(a). Preparation of H-Arg(NO$_2$)-Ala-NHNHZ 3.67 Grams of Boc-Arg(NO$_2$)-Ala-NHNHZ was dissolved in 15 ml of trifluoroacetic acid, and allowed to stand at a room temperature for 15 minutes, then crystallized by adding dried ether and the crystals were collected by filtration to obtain H-Arg(NO$_2$)-Ala-NHNHZ.

Rf$^I$: 0.20

3(b). Preparation of Boc-Arg(NO$_2$)-Arg(NO$_2$)-Ala-NHNHZ 2.17 Grams of Boc-Arg(NO$_2$)-OH was dissolved in a solution of 50 ml of tetrahydrofuran containing 0.69 ml of N-methylmorpholine, and the mixture was cooled to −15° C., then 0.89 ml of isobutyl chloroformate was added and the mixture was stirred vigorously for 30 minutes. To this mixture was added a solution of the above-obtained H-Arg(NO$_2$)-Ala-NHNHZ in 30 ml of dimethylformamide and 0.95 ml of triethylamine, and stirred for 1 minute. The reaction mixture was warmed to 0° C. for 5 minutes, then to 40° C. for 2 minutes, and stirred at a room temperature for 15 minutes. After removal of tetrahydrofuran and dimethylformamide by distillation, the residue was extracted with ethyl acetate. The extract was washed with 1N-citric acid and a saturated aqueous solution of sodium hydrogencarbonate in this order, then acetate was removed by distillation. Reprecipitated from ethyl acetate-ether to obtain 3.70 g of Boc-Arg(NO$_2$)-Ala-NHNHZ.

Rf$^I$: 0.58
Rf$^{II}$: 0.75

Elemental analysis (for C$_{28}$H$_{45}$N$_{13}$O$_{11}$): Calculated (%): C 45.46, H 6.13, N 24.61. Found (%): C 45.13, H 5.71, N 24.51.

4(a). Preparation of H-Arg(NO$_2$)-Arg(NO$_2$)-Ala-NHNHZ 3.00 Grams of Boc-Arg(NO$_2$)-Arg(NO$_2$)-Ala-NHNHZ was dissolved in 20 ml of trifluoroacetic acid, and the solution was allowed to stand at a room temperature for 15 minutes, then crystallized from dried ether. The crystals were collected by filtration to obtain H-Arg(NO$_2$)-Arg(NO$_2$)-Ala-NHNHZ.

Rf$^I$: 0.11

4(b). Preparation of Boc-Asn-Arg(NO$_2$)-Arg(NO$_2$)-Ala-NHNHZ

H-Arg(NO$_2$)-Arg(NO$_2$)-Ala-NHNHZ was dissolved in 50 ml of dimethylformamide, to this solution 0.56 ml of triethylamine and 2.17 g of Boc-Asn-ONHS were added and the mixture was allowed to stand at a room temperature for 20 hours. Dimethylformamide was removed by distillation, the residue thus obtained was extracted with butanol. The extract was washed with 2% of acetic acid twice, then reprecipitated from ether and the crystals were collected by filtration, reprecipitated from methanol-acetic acid to obtain 2.64 g of Boc-Asn-Arg(NO$_2$)-Arg(NO$_2$)-Arg-NHNHZ.

Rf$^I$: 0.40
Rf$^{II}$: 0.72

Elemental analysis (for C$_{32}$H$_{51}$N$_{15}$O$_{13}$): Calculated (%): C 54.01, H 6.02, N 24.60. Found (%): C 44.80, H 5.85, N 24.12.

4(c). Preparation of Boc-Asn-Arg-Arg-Ala-NHNH$_2$ 2.50 Grams of Boc-Asn-Arg(NO$_2$)-Arg(NO$_2$)-Ala-NHNHZ was dissolved in a mixture of 30 ml of methanol with 30% of acetic acid, and the solution was catalytically reduced by using palladium as the catalyst to obtain 2.20 g of Boc-Asn-Arg-Arg-Ala-NHNH$_2$.

Rf$^I$: 0.06
Rf$^{II}$: 0.40

Elemental analysis (for C$_{24}$H$_{47}$N$_{13}$O$_7$·2CH$_3$CO$_2$H·H$_2$O): Calculated (%): C 43.80, H 7.48, N 23.71. Found: (%): C 43.51, H 7.62, N 23.45.

5. Preparation of Z-Leu-Gly-OC$_2$H$_5$ 1.86 Milliliters of N-methylmorpholine was dissolved in 60 ml of tetrahydrofuran and to this solution 4.85 g of Z-Leu-OH was added. The mixture was cooled to −15° C. and 2.41 ml of isobutyl chloroformate was added and then vigorously stirred for 30 seconds. To this reaction mixture, 40 ml of a dimethylformamide solution containing 2.54 g of H-Gly-OC$_2$H$_5$, and 2.56 ml of triethylamine were added and stirred for 1 minute. After the reaction mixture was warmed at 0° C. for 5 minutes, then at 40° C. for 2 minutes and was stirred at a room temperature for 15 minutes. Tetrahydrofuran and dimethylformamide were removed by distillation to obtain the residue, then 1M-citric acid was added to this residue and the crystals thus formed were collected by filtration. The crystals were washed with water until the filtrate become neutral, and the crystals were dried, reprecipitated from ethyl acetate-ether to obtain 4.68 g of Z-Leu-Gly-OC$_2$H$_5$.

Rf$^I$: 0.80
Rf$^{II}$: 0.77

Elemental analysis (for C$_{18}$H$_{26}$N$_2$O$_5$): Calculated (%): C 61.70, H 7.48, N 7.99. Found (%): C 61.51, H 7.32, N 7.80.

6(a). Preparation of H-Leu-Gly-OC$_2$H$_5$ 3.12 Grams of Z-Leu-Gly-OC$_2$H$_5$ was dissolved in 50 ml of methanol and 8.90 ml of 1N hydrochloric acid and the solution was catalytically reduced by using palladium as the catalyst to obtain H-Leu-Gly-OC$_2$H$_5$.

Rf$^I$: 0.41

6(b). Preparation of Z-Ser-Leu-Gly-OC$_2$H$_5$ 2.48 Grams of Z-Ser-NHNH$_2$ was dissolved in 20 ml of dimethylformamide and 4.89 ml of N-hydrochloric acid/dioxane, after cooled the reaction mixture to −15° C., then 1.31 ml of isoamyl nitrite was added thereto and stirred for 5 minutes. Then 4.11 ml of triethylamine was added to the reaction mixture to neutralize the mixture. This reaction mixture was added into 10 ml of a dimethylformamide solution containing the above-mentioned H-Leu-Gly-OC$_2$H$_5$ and 1.24 ml of triethylamine and stirred at 4° C. for 20 hours. After removal of dimethylformamide by distillation, the residue thus obtained was extracted with ethyl acetate, and the extract was washed with 1N-citric acid and a saturated aqueous solution of sodium chloride in this order, then the extract was dried with anhydrous magnesium sulfate. After removal of ethyl acetate, reprecipitated from ethyl acetate to obtain 2.64 g of Z-Ser-Leu-Gly-OC$_2$H$_5$.
Rf$^I$: 0.78
Rf$^{II}$: 0.85

Elemental analysis (for C$_{21}$H$_{31}$N$_3$O$_7$): Calculated (%): C 57.65, H 7.14, N 9.60. Found (%): C 57.60, H 6.88, N 9.63.

7(a). Preparation of H-Ser-Leu-Gly-OC$_2$H$_5$ 2.50 Grams of Z-Ser-Leu-Gly-OC$_2$H$_5$ was dissolved in 10 ml of 10% acetic acid and 50 ml of methanol and the mixture was catalytically reduced by using palladium as the catalyst to obtain H-Ser-Leu-Gly OC$_2$H$_5$.
Rf$^I$: 0.31

7(b). Preparation of Z-Thr-His-Ser-Leu-Gly-OC$_2$H$_5$ 2.54 Grams of Z-Thr-His-NHNH$_2$ was dissolved in 20 ml of dimethylformamide and 4.19 ml of 6N-hydrochloric acid/dioxane, after cooled the mixture to −15° C., then 0.84 ml of isoamyl nitrate was added thereto and stirred for 5 minutes. Then 3.51 ml of triethylamine was added to neutralize the reaction mixture. This reaction mixture was added into 20 ml of a dimethylformamide solution containing the above obtained H-Ser-Leu-Gly-OC$_2$H$_5$ and 0.79 ml of triethylamine, and stirred at 4° C. for 20 hours. After removal of dimethylformamide by distillation, the residue thus obtained was extracted with butanol, the extract was washed with water. The solvent was removed by distillation, and recrystallized from methanol-ethyl acetate to obtain 4.31 g of Z-Thr-His-Ser-Leu-Gly-OC$_2$H$_5$.
Rf$^I$: 0.35
Rf$^{II}$: 0.71

Elemental analysis (for C$_{31}$H$_{45}$N$_7$O$_3$.H$_2$O): Calculated (%): C 64.00, H 8.11, N 16.85. Found (%): C 64.48, H 8.10, N 16.54.

8(a). Preparation of Z-Thr-His-Ser-Leu-Gly-NHNH$_2$ 4.30 Grams of Z-Thr-His-Ser-Leu-Gly-CO$_2$H$_5$ was dissolved in 20 ml of methanol, to this solution was added 3.18 ml of hydrazine monohydrate, then this mixture was allowed to stand at a room temperature for 20 hours. After the reaction was completed, ether was added to the reaction mixture and the crystals thus precipitated were collected by filtration and dried. The crystals were washed with hot methanol to obtain 2.55 g of Z-Thr-His-Ser-Leu-Gly-NHNH$_2$.
Rf$^I$: 0.17
Rf$^{II}$: 0.57

Elemental analysis (for C$_{29}$H$_{43}$N$_9$O$_9$): Calculated (%): C 52.64, H 6.55, N·19.05. Found (%): C 52.55, H 6.44, N 19.09.

8(b). Preparation of H-Asn-Arg-Arg-Ala-Leu-Ile-Leu-Leu-Ala-Gln-OH 0.78 Grams of Boc-Asn-Arg-Arg-Ala-NHNH$_2$ was dissolved in 8 ml of dimethylformamide and 1.03 ml of 6N-hydrochloric acid/dioxane, after the solution was cooled to −15° C. 0.16 ml of isoamyl nitrate was added thereinto and stirred for 5 minutes. Next 0.87 ml of triethylamine was added to neutralize the reaction mixture. This reaction mixture was added to a mixture consisting of Peptide A, i.e., H-Leu-Ile-Leu-Leu-Ala-Gln-OH, 0.87 ml of triethylamine, 20 ml of dimethylformamide and 10 ml of hexamethylphosphoric triamide, and the obtaining mixture was stirred at 4° C. for 24 hours. Further a product being converted 0.39 g of Boc-Asn-Arg-Arg-Ala-NHNH$_2$ into azide was added to said mixture and stirred for 48 hours. Dimethylformamide was removed by distillation, the residue thus obtained was extracted with butanol. The extract was washed with water and butanol was removed by distillation. The residue thus obtained was recrystallized from ether, and the crystals precipitated were collected by filtration, washed with water and dried on phosphorus pentoxide. Boc-Asn-Arg-Arg-Ala-Leu-Ile-Leu-Leu-Ala-Gln-OH thus obtained was dissolved in 3 ml of trifluoroacetic acid and was allowed to stand at a room temperature for 15 minutes, then dried ether was added thereto to precipitate the crystals and the crystals were collected by filtration. After the crystals were dried, they were purified by using Sephadex G-25 (eluting solvent: 50% acetic acid) to obtain 120 mg of H-Asn-Arg-Arg-Ala-Leu-Ile-Leu-Leu-Ala-Gln-OH.
Rf$^I$: 0.01
Rf$^{II}$: 0.35

Elemental analysis (for C$_{51}$H$_{94}$N$_{18}$O$_{13}$.2CH$_3$COOH.5H$_2$O): Calculated (%): C 47.95, H 8.19, N 18.30. Found (%): C 47.66, H 8.41, N 18.62.
[α]$_D^{25}$: −185.44 (C=0.57, 1M-acetic acid).

9. Preparation of H-Thr-His-Ser-Leu-Gly-Asn-Arg-Arg-Ala-Leu-Ile-Leu-Ala-Gln-OH 125 Milligrams of Z-Thr-His-Ser-Leu-Gly-NHNH$_2$ was dissolved in 10 ml of dimethylformamide and 0.125 ml of 6N-hydrochloric acid/dioxane, then after cooled to −15° C. 0.025 ml of isoamyl nitrite was added and stirred for 5 minutes. Next, 0.105 ml of triethylamine was added to neutralized the reaction mixture. This mixture was then added to a mixture consisting of 10 ml of a dimethylformamide solution containing 110 mg of H-Asn-Arg-Arg-Ala-Leu-Ile-Leu-Leu-Ala-Gln-OH with 0.013 ml of triethylamine; and 6 ml of hexamethylphosphoric triamide, then the whole mixture was stirred at 4° C. for 24 hours. Further, an azide product of 125 mg of Z-Thr-His-Ser-Leu-Gly-NHNH$_2$ was added to the reaction mixture, and stirred for 48 hours. Dimethylformamide was removed by distillation, thus obtained residue was extracted with butanol. The extract was washed with water and butanol was removed by distillation, and the residue thus obtained was reprecipitated from methanol-ethyl acetate. Then, thus obtained Z-Thr-His-Ser-Leu-Gly-Asn-Arg-Arg-Ala-Leu-Ile-Leu-Leu-Ala-Gln-OH was dissolved in 50 ml of methanol and 10 ml of 10%-acetic acid and catalytically reduced by using palladium as the catalyst. The catalyst was removed by filtration then methanol was removed by distillation, and the residue thus obtained was purified by using Sephadex G-25 (eluting solvent: 50%-acetic acid) to obtain 125 mg of H-Thr-His-Ser-Leu-Gly-Asn-Arg-Arg-Ala-Leu-Ile-Leu-Leu-Ala-Gln-OH. Hereinafter this product is referred to as [Peptide B].
Rf$^I$: 0.01
Rf$^{II}$: 0.38

Elemental analysis (for C$_{72}$H$_{127}$N$_{25}$O$_{20}$.2CH$_3$COOH.4H$_2$O): Calculated (%): C 49.21, H 7.77, N 18.87. Found (%): C 49.60, H 7.92, N 18.54.
[α]$_D^{25}$: −66.76 (C=0.42, 1M-acetic acid).

PREPARATIVE EXAMPLE A-3

1(a). Preparation of H-Gln-NHNHBoc 7.00 Grams of Z-Gln-NHNHBoc was dissolved in 50 ml of methanol and was catalytically reduced by using palladium as the catalyst to obtain H-Gln-NHNHBoc.
$Rf^I$: 0.37

1(b). Preparation of Z-Pro-Gln-NHNHBoc 4.41 Grams of Z-Pro-OH was dissolved in 50 ml of tetrahydrofuran and 1.80 ml of N-methylmorpholine, and the solution was cooled to $-15°$ C., then 2.34 ml of isobutyl chloroformate was added thereinto and stirred vigorously for 30 seconds. Then 30 ml of a dimethylformamide solution of H-Gln-NHNHBoc obtained in the step 1(a) above was added to the reaction mixture and stirred for 1 minute. Then the whole reaction mixture was warmed at 0° C. for 5 minutes, and further warmed at 40° C. for 2 minutes and stirred at room temperature for 15 minutes. Tetrahydrofuran and dimethylformamide were removed by distillation, the residue thus obtained was extracted with ethyl acetate containing a small amount of butanol. The extract was washed with 1N-citric acid, a saturated aqueous solution of sodium hydrogencarbonate and a saturated aqueous solution of sodium chloride in this order, then further washed with a hot ethyl acetate to obtain 5.67 g of Z-Pro-Gln-NHNHBoc.
$Rf^I$: 0.60
$Rf^{II}$: 0.76
Elemental analysis (for $C_{23}H_{33}N_5O_7$): Calculated (%): C 56.20, H 6.77, N 14.25. Found (%): C 55.97, H 6.68, N 14.15.

2(a). Preparation of H-Pro-Gln-NHNHBoc 5.50 Grams of Z-Pro-Gln-NHNHBoc was dissolved in 50 ml of methanol and was catalytically reduced by using palladium as the catalyst to obtain H-Pro-Gln-NHNHBoc.
$Rf^I$: 0.09

2(b). Preparation of Z-Leu-Pro-Gln-NHNHBoc 4.05 Grams of Z-Leu-ONHS was added to 100 ml of a dimethylformamide solution of H-Pro-Gln-NHNHBoc obtained in the above-mentioned step 2(a), and 1.56 ml of trithylamine, then the mixture was allowed to stand at a room temperature for 20 hours. Dimethylformamide was removed by distillation, and the residue thus obtained was extracted with ethyl acetate. The extract was washed with 1N-citric acid and a saturated aqueous solution of sodium chloride in this order, and reprecipitated from ethyl acetate-ether to obtain 3.72 g of Z-Leu-Pro-Gln-NHNHBoc.
$Rf^I$: 0.68
$Rf^{II}$: 0.80
Elemental analysis (for $C_{29}H_{44}N_6O_8$): Calculated (%): C 57.60, H 7.33, N 13.90. Found (%): C 57.21, H 7.08, N 13.58.

3(a). Preparation of H-Leu-Pro-Gln-NHNHBoc 3.50 Grams of Z-Leu-Pro-Gln-NHNHBoc was dissolved in 50 ml of methanol and was catalytically reduced by using palladium as the catalyst to obtain H-Leu-Pro-Gln-NHNHBoc.
$Rf^I$: 0.14

3(b). Preparation of Z-Asp(OCH$_2$-C$_6$H$_5$)-Leu-Pro-Gln-NHNHBoc 2.27 Grams of Z-Asp(OCH$_2$-C$_6$H$_5$)-OH was dissolved in 30 ml of tetrahydrofuran with 0.65 ml of N-methylmorpholine and after the solution was cooled to $-15°$ C., 0.84 ml of isobutyl chloroformate was added and stirred vigorously for 30 seconds. To this reaction mixture was added 20 ml of a dimethylformamide solution of H-Leu-Pro-Gln-NHNHBoc obtained in the above-mentioned step 3(a), with 0.81 ml of triethylamine and the whole mixture was stirred for 1 minute. Next this reaction mixture was warmed at 0° C. for 5 minutes, then at 40° C. for 2 minutes and stirred at a room temperature for 15 minutes. Tetrahydrofuran and dimethylformamide were removed by distillation and the residue thus obtained was extracted with ethyl acetate. The extract was washed with 1N-citric acid, a saturated aqueous solution of sodium hydrogencarbonate and a saturated aqueous solution of sodium chloride in this order and the solvent was removed by distillation. Reprecipitated form ethyl acetate-petroleum ether to obtain 4.00 g of Z-Asp-(OCH$_2$-C$_6$H$_5$)-Leu-Pro-Gln-NHNHBoc.
$Rf^I$: 0.68
$Rf^{II}$: 0.77
Elemental analysis (for $C_{40}H_{55}N_7O_{11}$): Calculated (%): C 59.32, H 6.84, N 12.11. Found (%): C 58.88, H 6.65, N 11.72.

4(a). Preparation of H-Asp-Leu-Pro-Gln-NHNHBoc 2.00 Grams of Z-Asp-(OCH$_2$-C$_6$H$_5$)-Leu-Pro-Gln-NHNHBoc was dissolved in 50 ml of methanol with 10 ml of 10%-acetic acid and was catalytically reduced by using palladium as the catalyst to obtain H-Asp-Leu-Pro-Gln-NHNHBoc.
$Rf^I$: 0.08

4(b). Preparation of Z-Ser-Asp-Leu-Pro-Gln-NHNHBoc 0.75 Grams of Z-Ser-NHNH$_2$ was disolved in 15 ml of dimethylformamide with 1.48 ml of 6N-hydrochloric acid/dioxane, after the solution was cooled to $-15°$ C., 0.39 ml of isoamyl nitrite was added thereto and stirred for 5 minutes, and 1.24 ml of triethylamine was added to neutralize the reaction mixture. This reaction mixture was added to a mixture consisting of 10 ml of a dimethylformamide solution of H-Asp-Leu-Pro-Gln-NHNHBoc obtained in the above-mentioned step 4(a) and 0.34 ml of trimethylamine, and the whole mixture was stirred at 4° C. for 20 hours. Dimethylformamide was removed by distillation and the residue thus obtained was extracted with butanol. The extract was washed with water, then butanol was removed by distillation. Recrystallized from methanol-ethyl acetate to obtain 1.52 g of Z-Ser-Asp-Leu-Pro-Gln-NHNHBoc.
$Rf^I$: 0.45
$Rf^{II}$: 0.67

5. Preparation of H-Ser-Asp-Leu-Pro-Gln-Thr-His-Ser-Leu-Gln-Asn-Arg-Arg-Ala-Leu-Ile-Leu-Leu-Ala-Gln-OH 116 Milligrams of Z-Ser-Asp-Leu-Pro-Gln-NHNHBoc was de-tert-butoxycarbonylated with 2 ml of TFA, and anhydrous ether was added to the reaction mixture to obtain the precipitate. Then the precipitate was collected by filtration, and dried, and dissolved in 5 ml of dimethylformamide with 0.072 ml of 6N-hydrochloric acid/dioxane. After the reaction mixture was cooled to −15° C., 0.019 ml of isoamyl nitrite was added to the mixture and stirred for 5 minutes, and then 0.081 ml of triethylamine was added to neutralize the reaction mixture.

This reaction mixture was added to a mixture consisting of 80 mg of Peptide B, i.e., H-Thr-His-Ser-Leu-Gly-Asn-Arg-Arg-Ala-Leu-Ile-Leu-Leu-Ala-Gln-OH, 5 ml of dimethylformamide and 6 ml of hexamethylphosphoric triamide, and stirred at 4° C. for 20 hours. Further, to the reaction mixture was added 116 mg of azide product of Z-Ser-Asp-Leu-Pro-Gln-NHNHBoc, then stirred for 28 hours. Dimethylformamide was removed by distillation and the residue thus obtained was extracted with butanol. The extract was washed with water and butanol was removed by distillation. Then the residue was crystallized from petroleum ether and the crystals precipitated were collected by filtration, then reprecipitated from methanol-ethyl acetate. Thus obtained Z-Ser-Asp-Leu-Pro-Gln-Thr-His-Ser-Leu-Gly-Asn-Arg-Arg-Ala-Leu-Ile-Leu-Leu-Ala-Gln-OH was dissolved in 30 ml of methanol with 30 ml of 10%-acetic acid and was catalytically reduced by using palladium as the catalyst. The catalyst was removed by filtration and the solvent was also removed by distillation. The residue thus obtained was purified by using Sephdex G-25 followed by LH-20 (eluting solvent: 1/1000N-hydrochloric acid was used respectively) to obtain 58 mg of H-Ser-Asp-Leu-Pro-Gln-Thr-His-Ser-Leu-Gly-Asn-Arg-Arg-Ala-Leu-Ile-Leu-Leu-Ala-Gln-OH. Hereinafter, this product is referred to as [Peptide C].

$Rf^I$: 0.01

$Rf^{II}$: 0.37

Elemental analysis (for $C_{95}H_{163}N_{31}O_{29} \cdot 2CH_3COOH \cdot 7H_2O$): Calculated (%): C 48.54, H 7.61, N 17.72. Found (%): C 48.14, H 7.50, N 17.48.

$[\alpha]_D^{25}$: −85.70 (C=0.23, 1M-acetic acid).

PREPARATIVE EXAMPLE A-4

1(a). Preparation of
H-Ser-Asp-Leu-Pro-Gln-NHNHBoc 1.03 Grams of Z-Ser-Asp-Leu-Pro-Gln-NHNHBoc was dissolved in 50 ml of methanol and was catalytically reduced by using palladium as the catalyst to obtain H-Ser-Asp-Leu-Pro-Gln-NHNHBoc.

$Rf^I$: 0.06

1(b). Preparation of
Z-Tyr-Ser-Asp-Leu-Pro-Gln-NHNHBoc 0.79 Gram of Z-Tyr-ONHS was added to 20 ml of a dimethylformamide solution of H-Ser-Asp-Leu-Pro-Gln-NHNHBoc obtained in the above-mentioned step 1(a), and the mixture was allowed to stand for 20 hours at room temperature. After dimethylformamide was removed by distillation, the residue thus obtained was extracted with ethyl acetate. The extract was washed with 1N-citric acid then with a saturated aqueous solution of sodium chloride in this order, then ethyl acetate was removed by distillation. Reprecipitated from methanol-ethyl acetate to obtain 588 mg of Z-Tyr-Ser-Asp-Leu-Pro-Gln-NHNHBoc.

$Rf^I$: 0.51

$Rf^{II}$: 0.69

Elemental analysis (for $C_{52}H_{69}N_9O_{15}$): Calculated (%): C 58.91, H 6.56, N 11.89. Found (%): C 58.53, H 6.22, N 12.28.

2. Preparation of
H-Tyr-Ser-Asp-Leu-Pro-Gln-Thr-His-Ser-Leu-Gly-Asn-Arg-Arg-Ala-Leu-Ile-Leu-Leu-Ala-Gln-OH 44 Milligrams of Z-Tyr-Ser-Asp-Leu-Pro-Gln-NHNHBoc was dissolved in 3 ml of dimethylformamide with 0.0225 ml of 6N-hydrochloric acid/dioxane, after the mixture was cooled to −15° C., 0.0060 ml of isoamyl nitrite was added and stirred for 5 minutes, then 0.0252 ml of triethylamine was added to neutralize the mixture.

This reaction mixture was added to a solution consisting of 5 ml of a dimethylformamide solution containing 25 mg of Peptide B, i.e., H-Thr-His-Ser-Leu-Gly-Asn-Arg-Arg-Ala-Leu-Ile-Leu-Leu-Ala-Gln-OH, and 2 ml of hexamethylphosphoric triamide then the whole mixture was stirred at 4° C. for 20 hours. Further, an azide product of 44 mg of Z-Tyr-Ser-Asp-Leu-Pro-Gln-NHNHBoc was added to the reaction mixture and was stirred for 24 hours. The solvent was removed by distillation and the residue thus obtained was extracted with a mixture of butanol-water then crystallized from ether and the crystals were collected by filtration. Thus obtained Z-Tyr-Ser-Asp-Leu-Pro-Gln-Thr-His-Ser-Leu-Gly-Asn-Arg-Arg-Ala-Leu-Ile-Leu-Leu-Ala-Gln-OH was dissolved in 30 ml of methanol and was catalytically reduced by using palladium as the catalyst. The catalyst was removed by filtration and methanol was also removed by distillation, then the residue was purified by using Sephdex G-25 (eluting solvent: 50%-acetic acid) and by using LH-20 (eluting solvent: 1/1000N-hydrochloric acid) to obtain 18 mg of H-Tyr-Ser-Asp-Leu-Pro-Gln-Thr-His-Ser-Leu-Gly-Asn-Arg-Arg-Ala-Leu-Ile-Leu-Leu-Ala-Gln-OH. Hereinafter this product is referred to as [Peptide D].

$Rf^I$: 0.01

$Rf^{II}$: 0.38

Elemental analysis (for $C_{104}H_{169}N_{32}O_{31} \cdot 2CH_3COOH \cdot 5H_2$): Calculated (%): C 50.40, H 7.32, N 17.41. Found (%): C 50.72, H 7.67, N 17.03.

$[\alpha]_D^{25}$: −77.88 (C=0.22, 1M-acetic acid).

PREPARATIVE EXAMPLE B

1. Preparation of Z-Lys(Tos)-Glu(OBzl)-OBzl 4.18 Grams of H-Glu(OBzl)-OBzl.Tos was dissolved in 30 ml of dimethylformamide (DMF), then 1.21 ml of triethylamine (TEA) was added and the mixture was stirred under cooling. On the other hand, 4.35 g of Z-Lys(Tos)-OH was dissolved in 30 ml of tetrahydrofuran (THF), and 0.98 ml of N-methylmorpholine was added thereto, then this mixture was cooled to −15° C. and under stirring condition 1.27 ml of isobutyl chloroformate was added dropwise. 30 Seconds after the addition, then the cooled DMF solution mentioned above was added thereto and this mixture was stirred at 0° C. for 5 minutes, then at 40° C. in a water bath for 1 minute, further at 15° C. for 30 minutes. THF and DMF were removed from the reaction mixture under a reduced pressure, the residue thus obtained was extracted with ethyl acetate. The extract was washed with 1N-citric acid, a saturated aqueous solution of sodium chloride, a saturated aqueous solution of sodium hydrogencarbonate then a saturated aqueous solution of sodium chloride in this order, then was dried with anhydrous sodium sulfate, and ethyl acetate was removed distillation. The oily residue obtained was solidified by adding ethyl ether and reprecipitated from ethyl acetate-ether to obtain 5.37 g of the desired product.

Rf$^I$: 0.96
Rf$^{II}$: 0.90

Elemental analysis (for $C_{40}H_{45}N_3O_9S$): Calculated (%): C 64.59, H 6.10, N 5.65. Found (%): C 64.13, H 5.95, N 5.63.

2(a). Preparation of H-Lys(Tos)-Glu-OH 5.21 Grams of Z-Lys(Tos)-Glu(OBzl)-OBzl was dissolved in a mixture of 80 ml of methanol with 20 ml of 10% acetic acid, and a small amount of palladium black was added thereto and stirred overnight under introducing hydrogen gas. After the reaction was completed, the catalyst was removed by vacuum filtration, and the filtrate was distilled under a reduced pressure to obtain the rresidue. To the residue was poured water and was lyophilized to obtain the desired product.

Rf$^I$: 0.29
Rf$^{II}$: 0.52

2(b). Preparation of Z-Ser-Lys(Tos)-Glu-OH 2.13 Grams of Z-Ser-NHNH$_2$ was dissolved in 20 ml of DMF and 4.20 ml of 6N-hydrochloric acid/dioxane was further added, then the mixture was cooled to $-15°$ C., 1.13 ml of isoamyl nitrite was added under stirring. After the reaction mixture shows negative reaction in hydrazid test, then a cold solution of 3.53 ml of triethylamine with 1.20 ml of DMF was added dropwise to neutralize the reaction mixture. This mixture containing the azide was added to a cold DMF solution of H-Lys(Tos)-Glu-OH obtained in above-mentioned step 2(a) with 1.96 ml of triethylamine, then this mixture was stirred at $-10°$ to $-15°$ C. for 2 hours and at 4° C. for 20 hours. Dimethylformamide was removed by distillation, the residue thus obtained was extracted with ethyl acetate, then the ethyl acetate layer was washed with 1N-citric acid and a saturated aqueous solution of sodium chloride, then dried with anhydrous sodium sulfate, and ethyl acetate was removed by distillation under a reduced pressure. The residue thus obtained was solidified by adding ethyl ether and reprecipitated from ethyl acetate-ether to obtain 4.14 g of the desired product.

Rf$^I$: 0.65
Rf$^{II}$: 0.65

Elemental analysis (for $C_{29}H_{38}N_4O_{11}S \cdot \frac{1}{2}H_2O$): Calculated (%): C 52.80, H 5.96, N 8.49. Found (%): C 52.87, H 5.69, N 8.46.

3(a) Preparation of H-Ser-Lys(Tos)-Glu-OH 4.03 Grams of Z-Ser-Lys(Tos)-Glu-OH was dissolved in a mixture of 60 ml of methanol with 40 ml of 10%-acetic acid and a small amount of palladium black was added and stirred overnight under introducing hydrogen gas. After completion of the reaction, the catalyst was removed by vacuum filtration, and the filtrate was distilled under a reduced pressure, then the residue was poured into water and was lyophilized to obtain the desired product.

Rf$^I$: 0.23
Rf$^{II}$: 0.48

3(b). Preparation of Z-Arg(NO$_2$)-Ser-Lys(Tos)-Glu-OH

H-Ser-Lys(Tos)-Glu-OH obtained in the above-mentione step 3(a) was dissolved in 20 ml of dimethylformamide, and 1.74 ml of triethylamine was added then stirred under cooling. On the other hand, 2.41 g of Z-Arg(NO$_2$)-OH was dissolved in 20 ml of tetrahydrofuran, and 0.70 ml of N-methylmorpholine was added thereto, the mixture was cooled to $-15°$ C. and under stirring condition 0.86 ml of isobutyl chloroformate was added dropwise. 30 Seconds after the addition the above-mentioned cold dimethylformamide solution was added, then the whole mixture was stirred at 0° C. for 5 minutes, then at 15° C. for 30 minutes. Tetrahydrofuran and dimethylformamide were removed by distillation under a reduced pressure and the residue thus obtained was extracted with a butanol being saturated with 2%-acetic acid. The extract was washed 5 times with 2%-acetic acid being saturated with n-butanol, and distilled under a reduced pressure to remove acetic acid by replacing with water, further to remove water by replacing methanol. The oily residue thus obtained was solidified by adding ethyl ether and reprecipitated from ethyl acetate-methanol to obtain 4.09 g of the desired product.

Rf$^I$: 0.42
Rf$^{II}$: 0.65

Elemental analysis (for $C_{35}H_{49}N_9O_{14}S \cdot \frac{1}{2}H_2O$): Calculated (%): C 48.83, H 5.85, N 14.64. Found (%): C 49.22, H 6.05, N 14.11.

4. Preparation of Z-Ser-Leu-NHNH$_2$ 2.54 Grams of Z-Ser-NHNH$_2$ was dissolved in 20 ml of dimethylformamide, and 5.00 ml of 6N-hydrochloric acid/dioxane was added thereto and the mixture was cooled to $-15°$ C., then 1.34 ml of isoamyl nitrite was added under stirring condition. After the reaction mixture shows a negative reaction in hydrazine test, then a cold solution of 1.40 ml of dimethylformamide with 4.20 ml of triethylamine was added drop by drop in small amounts to neutralize the reaction mixture. This reaction mixture containing the azide was added to a 15 ml of a cold dimethylformamide solution containing 1.96 g of H-Leu-OC$_2$H$_5$·HCl and 1.40 ml of triethylamine, then whole mixture was stirred at $-10°$ to $-15°$ C. for 2 hours and at 4° C. for 20 hours. Dimethylformamide was removed by distillation under a reduced pressure and the residue thus obtained was extracted with ethyl acetate, then the ethyl acetate layer was washed with 1N-citric acid, a saturated aqueous solution of sodium chloride, a saturated aqueous solution of sodium hydrogencarbonate and a saturated aqueous solution of sodium chloride in this order and dried with anhydrous sodium sulfate then ethyl acetate was removed by distillation under a reduced pressure. To the residue thus obtained was added petroleum ether and washed by decantation. The oily substance obtained was dried under a reduced pressure in a desiccator, and the dried product was dissolved in 50 ml of methanol and 2.50 ml of 100% hydrazine monohydrate was added under ice-cooled condition, then the reaction product was allowed to stand at a room temperature for 20 hours, then methanol was removed by distillation under a reduced pressure. The residue thus obtained was solidified by adding ethyl ether and was dried in a desiccator. The dried product was washed with water to remove an excess of hydrazine monohydrate and reprecipitated from methanol-ethyl acetate to obtain 2.68 g of the desired product.

Rf$^I$: 0.73
Rf$^{II}$: 0.76

Elemental analysis (for $C_{17}H_{26}N_4O_5$): Calculated (%): C 55.73, H 7.15, N 15.29. Found (%): C 55.72, H 7.01, N 15.42.

5(a). Preparation of H-Arg-Ser-Lys(Tos)-Glu-OH 2.00 Grams of Z-Arg(NO$_2$)-Ser-Lys(Tos)-Glu-OH was suspended in a mixture of 30 ml of methanol with 30 ml of 50%-acetic acid and a small amount of palladium black was added thereto and the mixture was stirred for 36 hours under introducing hydrogen gas. After the reaction was completed, the catalyst was removed by filtration in vacuo, and the filtrate was distilled under a reduced pressure to obtain residue, then the residue was poured into water and was lyophilized. In 18 hours after the lyophilization, the lyophilized product was dissolved in water, then again the solution was lyophilized to obtain the desired product.

Rf$^I$: 0.05
Rf$^{II}$: 0.41

5(b). Preparation of Z-Ser-Leu-Arg-Ser-Lys(Tos)-Glu-OH 1.03 Grams of Z-Ser-Leu-NHNH$_2$ was dissolved in 15 ml of dimethylformamide, then 1.41 ml of 6N-hydrochloric acid/dioxane was further added thereto, and the mixture was cooled to $-15°$ C., then 0.38 ml of isoamyl nitrite was added under a stirring condition. After the reaction mixture shows a negative reaction in hydrazide test, then a cold solution of 0.40 ml of dimethylformamide with 1.18 ml of triethylamine was added drop by drop in small amounts to neutralize the reaction mixture. This reaction mixture containing the azide was added to 10 ml of a cold dimethylformamide solution containing H-Arg-Ser-Lys(Tos)-Glu-OH obtained in the above-mentioned step 5(a) and 0.66 ml of triethylamine, then whole mixture was stirred at $-10°$ to $-15°$ C. for 2 hours, and at 4° C. for 20 hours. Dimethylformamide was removed by distillation under a reduced pressure and the residue thus obtained was extracted with n-butanol saturated with water and the butanol layer was wahsed 5 times with water being saturated with n-butanol and the solvent was removed by distillation. The residue was solidified by adding ethyl ether, and reprecipitated from methanol-ethyl acetate to obtain 1.92 g of the desired product.

Rf$^I$: 0.33
Rf$^{II}$: 0.69

Elemental analysis (for $C_{44}H_{66}N_{10}O_{15}S.2H_2O$): Calculated (%): C 50.66, H 6.76, N 13.43. Found (%): C 50.57, H 6.51, N 13.34.

6(a). Preparation of H-Ser-Leu-Arg-Ser-Lys(Tos)-Glu-OH 1.84 Grams of Z-Ser-Leu-Arg-Ser-Lys(Tos)-Glu-OH was suspended in a mixture of 30 ml of methanol with 30 ml of 10%-acetic acid, and a small amount of palladium black was added to the suspension and stirred for 13 hours under introducing hydrogen gas. After the reaction was completed, the catalyst was removed by suction filtration to obtain the filtrate. Then filtrate was distilled under a reduced pressure and the thus obtained residue was pured into water and then lyophilized to obtain the desired product.

Rf$^I$: 0.09
Rf$^{II}$: 0.53

6(b). Preparation of Boc-Glu(OBzl)-Ser-Leu-Arg-Ser-Lys(Tos)-Glu-OH

H-Ser-Leu-Arg-Ser-Lys(Tos)-Glu-OH obtained in the above-mentioned step 6(a) was dissolved in 20 ml of dimethylformamide, then 0.51 ml of triethylamine was added thereto under ice-cooling condition, further 0.95 g of Boc-Glu(OBzl)-ONHS was added thereto and the whole mixture was stirred at a room temperature for 24 hours. Dimethylformamide was removed by distillation under a reduced pressure, the residue thus obtained was extracted with n-butanol being saturated with water, then the butanol layer was washed 5 times with water being saturated with n-butanol. The butanol layer was subjected to distillation under a reduced pressure, the residue thus obtained was solidified by adding ethyl ether, then reprecipitated from methanol-ethyl acetate to obtain 1.70 g of the desired product.

Rf$^I$: 0.42
Rf$^{II}$: 0.60

Elemental analysis (for $C_{53}H_{81}N_{11}O_{18}S.2H_2O$): Calculated (%): C 51.82, H 6.97, N 12.55. Found (%): C 51.27, H 6.58, N 12.47.

7(a). Preparation of Boc-Glu-Ser-Leu-Arg-Ser-Lys(Tos)-Glu-OH

150 Milligrams of Boc-Glu(OBzl)-Ser-Leu-Arg-Ser-Lys(Tos)-Glu-OH was dissolved in a mixture of 30 ml of methanol with 30 ml of 10%-acetic acid, to this solution was added a small amount of palladium black and stirred for 18 hours under the conditions of introducing hydrogen gas. After completion of the reaction, the catalyst was removed by suction filtration, the filtrate was subjected to distillation under a reduced pressure, the residue thus obtained was added water and was lyophilized to obtain the desired product.

7(b). Preparation of H-Glu-Ser-Leu-Arg-Ser-Lys(Tos)-Glu-OH

Boc-Glu-Ser-Leu-Arg-Ser-Lys(Tos)-Glu-OH obtained in the above-mentioned step 7(a) was dissolved in tetrahydrofuran, and the solution was allowed to stand at a room temperature for 15 minutes. 30 Milliliters of anhydrous ether was added to the solution, the precipitate thus formed was collected by filtration, washed with anhydrous ether, then the precipitate was dried under a reduced pressure in a desiccator containing potassium hydroxide-phosphorus petoxide as the desiccant, to obtain the desired product.

7(c). Preparation of H-Glu-Ser-Leu-Arg-Ser-Lys-Glu-OH

H-Glu-Ser-Leu-Arg-Ser-Lys(Tos)-Glu-OH obtained in the above-mentioned step 7(b) was dissolved in liquid ammonia being dried with metallic sodium previously, then small pieces of metallic sodium were added to the solution under stirring condition until the color of the reaction mixture is changed to blue and kept it for 30 seconds to 1 minute. Further crystals of NH$_4$Cl were added to the reaction mixture, an excess metallic sodium was neutralized, after ammonia was removed completely by distillation at a room temperature, the reaction product was subjected to gel-filtration on Sephadex G-25 gel by using 50%-acetic acid as the eluting solvent to obtain 58 mg of the desired product. Hereinafter, this product is referred to as [Peptide E].

Rf$^I$: 0.04
Rf$^{II}$: 0.34

Elemental analysis (for $C_{34}H_{61}N_{11}O_{14} \cdot C_2H_4O_2 \cdot 3H_2O$): Calculated (%): C 44.95, H 7.44, N 16.02. Found (%): C 45.05, H 7.11, N 15.84.

8(a). Preparation of H-Gln-NHNHBoc 16.00 Grams of Z-Gln-NHNHBoc was suspended in 100 ml of methanol, a small amount of palladium black was added thereto and stirred for 18 hours under the condition of introducing hydrogen gas. After completion of the reaction, the catalyst was removed by suction filtration, the filtrate was subjected to distillation under a reduced pressure, the residue thus obtained was dried under a reduced pressure in a desiccator to obtain the desired product.

$Rf^I$: 0.37
$Rf^{II}$: 0.58

8(b). Preparation of Z-Leu-Gln-NHNHBoc

H-Gln-NHNHBoc obtained in the above-mentioned step 8(a) was dissolved in 50 ml of tetrahydrofuran, and 5.51 g of Z-Leu-ONHS was added thereto under ice-cooling condition, then the reaction mixture was stirred at a room temperature for 18 hours. Tetrahydrofuran was removed by distillation under a reduced pressure, the residue obtained was extracted with ethyl acetate, then the ethyl acetate layer was washed with 1N-citric acid, a saturated aqueous solution of sodium chloride, a saturated aqueous solution of sodium hydrogencarbonate and a saturated aqueous solution of sodium chloride in this order, and the washed ethyl acetate layer was dried with anhydrous sodium sulfate, then ethyl acetate was removed by distillation. The oily residue obtained was solidified by adding ethyl ether, and the solid substance was reprecipitated from methanol-ethyl ether to obtain 6.04 g of the desired product.

$Rf^I$: 0.81
$Rf^{II}$: 0.86

Elemental analysis (for $C_{24}H_{37}N_5O_7$): Calculated (%): C 56.79, H 7.35, N 13.80. Found (%): C 56.67, H 7.15, N 13.75.

9(a). Preparation of H-Leu-Gln-NHNHBoc 2.79 Grams of Z-Leu-Gln-NHNHBoc was suspended in 80 ml of methanol, a small amount of palladium black was added to this suspension and the suspension was stirred for 32 hours under the condition of introducing hydrogen gas. After completion of the reaction, the catalyst was removed by suction filtration, the filtrate was subjected to distillation under a reduced pressure, the residue obtained was dried under a reduced pressure in a desiccator to obtain the desired product.

$Rf^I$: 0.33
$Rf^{II}$: 0.66

9(b). Preparation of Z-Asn-Leu-Gln-NHNHBoc

H-Leu-Gln-NHNHBoc obtained in the above-mentioned step 9(a) was dissolved in 30 ml of dimethylformamide, the solution was cooled under stirring condition. On the other hand, 1.61 g of Z-Asn-OH was dissolved in 30 ml of tetrahydrofuran, to this solution 0.62 ml of N-methylmorpholine was added and was cooled to $-15°$ C., then 0.80 ml of isobutyl chloroformate was added dropwise thereto under stirring condition. 30 Seconds after the addition of isobutyl chloroformate, the dimethylformamide solution of H-Leu-Gln-NHNHBoc as prepared previously was added thereto, the whole mixture was stirred at 0° C. for 5 minutes, next at 40° C. for 1 minute in water bath, further at 15° C. for 30 minutes. From the reaction mixture tetrahydrofuran and dimethylformamide were removed by distillation under a reduced pressure, the residue thus obtained was extracted with ethyl acetate. The extract was washed with 1N-citric acid, a saturated aqueous solution of sodium chloride, a saturated aqueous solution of sodium hydrogencarbonate and a saturated aqueous solution of sodium chloride in this order, then was dried with anhydrous sodium sulfate, and ethyl acetate was removed by distillation. The oily residue obtained was solidified by adding ethyl ehter, reprecipitated from methanol-ethyl acetate to obtain 2.55 g of the desired product.

$Rf^I$: 0.63
$Rf^{II}$: 0.77

Elemental analysis (for $C_{28}H_{43}N_7O_9$): Calculated (%): C 53.10, H 6.97, N 15.77. Found (%): C 53.67, H 6.63, N 15.68.

10(a). Preparation of Z-Thr-ONHS 1.28 Grams of Z-Thr-OH was dissolved in 30 ml of tetrahydrofuran, to this solution was added 0.58 g of N-hydroxysuccinimide (NHS), ice-cooled the mixture, then 1.05 g of N,N-dicyclohexylcarbodiimide (DCC) was added to the mixture. The whole mixture was stirred at 4° C. for 24 hours, the precipitate formed was removed by filtration, the filtrate was subjected to distillation under a reduced pressure, to the residue obtained was added ethyl ether, and washed by decantation. The oily substance obtained was dried under a reduced pressure in a desiccator to obtain the desired product.

10(b). Preparation of H-Asn-Leu-Gln-NHNHBoc 2.43 Grams of Z-Asn-Leu-Gln-NHNHBoc was suspended in 80 ml of methanol, a small amount of palladium black was added to the suspension, and the suspension was stirred for 18 hours under the condition of introducing hydrogen gas. After completion of the reaction, the catalyst was removed by suction filtration, the filtrate was subjected to distillation under a reduced pressure to remove the solvent, the residue obtained was dried under a reduced pressure in a desiccator to obtain the desired product.

$Rf^I$: 0.31
$Rf^{II}$: 0.64

10(c). Preparation of Z-Thr-Asn-Leu-Gln-NHNHBoc

H-Asn-Leu-Gln-NHNHBoc obtained in the above-mentioned step 19(b) was dissolved in 30 ml of dimethylformamide, to this solution was added 20 ml of the dimethylformamide solution of Z-Thr-ONHS obtained in the above-mentioned step 10(a) under a ice-cooled condition, the whole mixture was stirred at a room temperature for 18 hours. Dimethylformamide was removed by distillation under a reduced pressure, the residue obtained was solidified by adding 1N-citric acid, and reprecipitated from methanol-ethyl acetate to obtain 2.12 of the desired product.

$Rf^I$: 0.82
$Rf^{II}$: 0.79

Elemental analysis (for $C_{32}H_{50}N_8O_{11}$): Calculated (%): C 53.18, H 6.97, N 15.50. Found (%): C 52.85, H 6.95, N 15.28.

11(a). Preparation of Z-Thr-Asn-Leu-Gln-NHNH$_2$ 0.91 Gram of Z-Thr-Asn-Leu-Gln-NHNHBoc was dissolved in 8 ml of TFA, and was allowed to stand at a room temperature for 15 minutes. 80 Milliliters of anhydrous ether was added to this solution and the precipitate formed was collected quickly by filtration, washed with anhydrous ether, then was dried under a reduced pressure in a desiccator containing potassium hydroxide-phosphorus pentoxide as the desiccant, to obtain the desired product.

Rf$^I$: 0.34

11(b). Preparation of H-Glu(OBzl)-Ser-Leu-Arg-Ser-Lys-Lys(Tos)-Glu-OH 1.00 Gram of Boc-Glu(OBzl)-Ser-Leu-Arg-Ser-Lys(-Tos)-Glu-OH was dissolved in 8 ml of TFA, and was allowed to stand at a room temperature for 15 minutes. 80 Milliliters of anhydrous ether was added to this solution and the precipitate formed was collected quickly by filtration, washed with anhydrous ether, then dried under a reduced pressure in a desiccator containing potassium hydroxide-phosphorus pentoxide as the desiccant, to obtain the desired product.

Rf$^I$: 0.24
Rf$^{II}$: 0.44

11(c). Preparation of Z-Thr-Asn-Leu-Gln-Glu(OBzl)-Ser-Leu-Arg-Ser-Lys(Tos)-Glu-OH Z-Thr-Asn-Leu-Gln-NHNH$_2$ obtained in the above-mentioned step 11(a) was dissolved in 10 ml of dimethylformamide, further 0.63 ml of 6N-hydrochloric acid/-dioxane was added thereto, then the mixture was cooled to $-15°$ C., and 0.17 ml of isoamyl nitrite was added to the mixture under stirring condition. After the reaction mixture shows a negative reaction in hydrazine-test, 0.53 ml of triethylamine with 0.40 ml of cold dimethylformamide solution was added drop by drop in small amount to neutralize the reaction mixture. This solution containing azide compound was added to 10 ml of a cold dimethylformamide solution containing H-Glu-(OBzl)-Ser-Leu-Arg-Ser-Lys(Tos)-Glu-OH obtained in the above-mentioned step 11(b) and 0.24 ml of triethylamine, the whole mixture was reacted at $-10°$ to $-15°$ C. for 2 hours, next at 4° C. for 18 hours under stirring condition. Further, as similar to the procedure in the above-mentioned step 11(a), the product obtained by treating 1.16 g of Z-Thr-Asn-Leu-Gln-NHNHBoc with TFA was added to the above-mentioned reaction product and reacted at the same temperature for 24 hours with stirring condition. Dimethylformamide was removed by distillation under a reduced pressure, the residue obtained was extracted with n-butanol being saturated with water, washed with water being saturated with n-butanol 5 times, then the extract was subjected to distillation under a reduced pressure. The residue obtained was solidified by adding ethyl ether, reprecipitated from methanol-ethyl acetate, further the precipitate was washed with a hot methanol to obtain the desired product.

11(d). Preparation of H-Thr-Asn-Leu-Gln-Glu-Ser-Leu-Arg-Ser-Lys(Tos)-Glu-OH

Z-Thr-Asn-Leu-Gln-Glu(OBzl)-Ser-Leu-Arg-Ser-Lys(Tos)-Glu-OH obtained in the above-mentioned step 11(c) was suspended in a mixture of 50 ml of methanol with 50 ml of 30%-acetic acid, and small amount of palladium black was added to the suspension, and was stirred for 18 hours under the condition of introducing hydrogen gas. After completion of the reaction, the catalyst was removed by suction filtration, the filtrate was subjected to distillation under a reduce pressure, after methanol was removed completely by distillation, the concentrated liquor obtained was subjected to gel-filtration by Sephadex G-25 using 50%-acetic acid as the eluting solvent, for collecting the desired franction to obtain 740 mg of the objective product.

Rf$^I$: 0.17
Rf$^{II}$: 0.35

Elemental analysis (for $C_{66}H_{99}N_{17}O_{23} \cdot C_2H_4O_2 \cdot 2H_2O$): Calculated (%): C 48.91, H 7.08, N 15.64. Found (%): C 48.82, H 6.63, N 15.74.

12. Preparation of H-Thr-Asn-Leu-Gln-Glu-Ser-Leu-Arg-Ser-Lys-Glu-OH 51.0 Milligrams of H-Thr-Asn-Leu-Gln-Glu-Ser-Leu-Arg-Ser-Lys(Tos)-Glu-OH was dissolved in liquid ammonia being dried with metallic sodium previously, then small pieces of metallic sodium were added to the solution under stirring condition until the color of the reaction mixture is changed to blue and kept it for 30 seconds to 1 minute. Further crystals of NH$_4$Cl were added to the reaction mixture, an excess metallic sodium was neutralized, after ammonia was completely removed by distillation at a room temperature, the reaction product was subjected to gel-filtration with Sephadex G-25 gel by using 50%-acetic acid as the eluting solvent, for collecting the desired fraction, and the lyophilizing the raction by adding water after concentration, to obtain 32 mg of the desired product (peptide of the present invention). Hereinafter, this product is referred to as [Peptide F].

Rf$^I$: 0.01
Rf$^{II}$: 0.37

Elemental analysis (for $C_{53}H_{93}N_{17}O_{21} \cdot C_2H_4O \cdot 3H_2O$): Calculated (%): C 46.57, H 7.32, N 16.79. Found (%): C 46.10, H 6.98, N 16.82.

13. Preparation of Z-Leu-Ser-OCH$_3$ 1.81 Grams of H-Ser-OCH$_3$.HCl was dissolved in 25 ml of dimethylformamide, the 1.62 ml of triethylamine was added to the solution and the mixture was ice-cooled to $-10°$ C. To this mixture was added 4.21 g of Z-Leu-ONHS with stirring condition, and the reaction was continued for 18 hours under stirring. Dimethylformamide was removed by distillation, the residue obtained was extracted with ethyl acetate, the ethyl acetate layer was washed with water, dried with anhydrous sodium sulfate, then ethyl acetate was removed by distillation under a reduced pressure. The residue obtained was solidified by adding ethyl ether, reprecipitated from ethyl acetate-ether to obtain 2.68 g of the desired product.

Rf$^I$: 0.81
Rf$^{II}$: 0.82

Elemental analysis (for $C_{18}H_{26}N_2O_6$): Calculated (%): C 59.00, H 7.15, N 7.65. Found (%): C 58.62, H 7.03, N 7.65.

14(a). Preparation of H-Leu-Ser-OCH$_3$.HCl 4.20 Grams of Z-Leu-Ser-OCH$_3$ was suspended in a mixture of 40 ml of methan-1 with 11.46 ml of 1N- hydrochloric acid, then a small amount of palladium black was added to the suspension, stirred for 18 hours under the condition of introducing hydrogen gas. After completion of the reaction the catalyst was removed by suction filtration, the filtrate was subjected to distillation under a reduced pressure, further to the residue obtained was added water and distillation under a reduced pressure were repeated 3 times. The residue thus obtained was dried under a reduced pressure in a desiccator containing phosphorus pentoxide as the desiccant to obtain the desired product.

$Rf^I$: 0.38

14(b). Preparation of Z-Ser-Leu-Ser-OCH$_3$ 3.19 Grams of Z-Ser-NHNH$_2$ was dissolved in 25 ml of dimethylformamide, and 6.30 ml of 6N-hydrochloric acid/dioxane was added to the solution, cooled to $-15°$ C., then 1.69 ml of isoamyl nitrite was added thereto. After the reaction mixture shows a negative reaction in hydrazine-test, 1.76 ml of a cold dimethylformamide solution with 5.29 ml of triethylamine was added drop by drop in small amount to neutralize the reaction mixture. This reaction mixture containing an azide product was added to 20 ml of a cold dimethylformamide solution containing H-Leu-Ser-OCH$_3$.HCl obtained in the above-mentioned step 14(a) and 1.60 ml of triethylamine, and the whole mixture was stirred at $-10°$ to $-15°$ C. for 2 hours, next at 4° C. for 18 hours. Dimethylformamide was removed by distillation under a reduced pressure, the residue obtained was solidified by adding water, reprecipitated from methanol-ethyl acetate to obtain 4.11 g of the desired product.

$Rf^I$: 0.76
$Rf^{II}$: 0.79

Elemental analysis (for C$_{21}$H$_{31}$N$_3$O$_8$): Calculated (%): C 55.62, H 6.89, N 9.27. Found (%): C 55.48, H 6.92, N 9.18.

15. Preparation of Z-Ser-Leu-Ser-NHNH$_2$ 2.00 Grams of Z-Ser-Leu-Ser-OCH$_3$ was dissolved in 40 ml of methanol, then 1.10 ml of 100%-NH$_2$NH$_2$.H$_2$O was added to the solution under ice-cooled condition, and the reaction mixture was allowed to stand at a room temperature for 18 hours. After completion of the reaction, the solvent was removed by distillation under a reduced pressure, and the residue obtained was solidified by adding ether, then an excess of NH$_2$NH$_2$.H$_2$O was removed by adding water, then reprecipitated from methanol-ethyl acetate to obtain 1.91 g of the desired product.

$Rf^I$: 0.43
$Rf^{II}$: 0.73

Elemental analysis (for C$_{20}$H$_{31}$N$_5$O$_7$): Calculated (%): C 52.97, H 6.89, N 15.44. Found (%): C 52.85, H 6.70, N 15.44.

16(a). Preparation of Z-Ser-Leu-Ser-Thr-Asn-Leu-Gln-Glu-Ser-Leu-Arg-Ser-Lys(Tos)-Glu-OH 70.42 Milligrams of Z-Ser-Leu-Ser-NHNH$_2$ was dissolved in 5 ml of dimethylformamide, to this solution was added 0.78 ml of 10 times diluted-dimethylformamide solution of 6N-hydrochloric acid/dioxane, then the mixture was cooled to $-15°$ C., and 0.20 ml of a 10-fold diluted-dimethylformamide solution of isoamyl nitrite under stirring. After the reaction mixture shows a negative reaction in hydrazide-test, 0.65 ml of 10-fold diluted-dimethylformamide solution of triethylamine was added drop by drop in a small amount to neutralize the reaction mixture. This reaction mixture containing azide product was added to 5 ml of a cold dimethylformamide solution containing 151 mg of H-Thr-Asn-Leu-Gln-Glu-Ser-Leu-Arg-Ser-Lys(Tos)-Glu-OH and 0.29 ml of 10 times-diluted dimethylformamide solution of triethylamine, then the whole mixture was stirred at $-10°$ to $-15°$ C. for 2 hours, next at 4° C. for 18 hours. Further 117.36 mg of Z-Ser-Leu-Ser-NHNH$_2$ was added thereto and was reacted for 24 hours.

Dimethylformamide was removed by distillation under a reduced pressure, the residue obtained was extracted with n-butanol being saturated with water, then the extract was washed 10 times with water being saturated with n-butanol, further washed 5 times with 2%-acetic acid being saturated with n-butanol, the extract was subjected to distillation under a reduced pressure, to the residue obtained was added water and subjected to distillation under a reduced pressure, after n-butanol was removed by distillation completely, the product was lyophilized, then the lyophilized product was reprecipitated from ethyl acetate-ether to obtain the desired product.

16(b). Preparation of H-Ser-Leu-Ser-Thr-Asn-Leu-Gln-Glu-Ser-Leu-Arg-Ser-Lys-Glu-OH 150 Milligrams of Z-Ser-Leu-Ser-Thr-Asn-Leu-Gln-Glu-Ser-Leu-Arg-Ser-Lys(Tos)-Glu-OH was dissolved in liquid ammonia previously dried with metallic sodium, then small pieces of metallic sodium were added to the solution under stirring condition until the color of the reaction mixture is changed to blue and kept it for 30 seconds to 1 minute. Further crystals of NH$_4$Cl were added to the reaction mixture, an excess metallic sodium was neutralized, after ammonia was removed completely by distillation at a room temperature, the reaction product was subjected to gel-filtration with Sephadex G-25 gel by using 50%-acetic acid as the eluting solvent, collecting the desired fraction and lyophilizing the desired fraction by adding water after concentration, to obtain 94 mg of the desired product (peptide of the present invention). Hereinafter, this product is referred to as [Peptide G].

$Rf^I$: 0.02
$Rf^{II}$: 0.39

Elemental analysis (for C$_{65}$H$_{120}$N$_{20}$O$_{26}$.C$_2$H$_4$O$_2$.H$_2$O): Calculated (%): C 48.19, H 7.24, N 16.78. Found (%): C 47.93, H 6.93, N 16.49.

17(a). Preparation of Z-Tyr-OSu 1.04 Grams of Z-Tyr-OH was dissolved in 30 ml of tetrahydrofuran, to this solution 0.38 g of N-hydroxysuccinimide was added, then the reaction mixture was ice-cooled, 0.68 g of dicyclohexylcarbodiimide was added under ice-cooled condition, and the whole mixture was stirred at 4° C. for 18 hours. The precipitate formed was removed by suction filtration, the filtrate was subjected to distillation under a reduced pressure, to the residue obtained was added ethyl ether and petroleum ether and was decanted, then dried to obtain the desired product.

17(b). Preparation of H-Ser-Leu-Ser-OCH$_3$ 1.00 Gram of Z-Ser-Leu-Ser-OCH$_3$ obtained in the above-mentioned step 14(b) was suspended in 20 ml of methanol with 20 ml of 10%-acetic acid, then a small amount of palladium black was added to the suspension, and the suspension was stirred for 14 hours under the condition of introducing hydrogen gas. After completion of the reaction, the catalyst was removed by suction filtration, the filtrate was subjected to distillation under a reduced pressure, then water was added to the residue and lyophilized to obtain the desired product.

$Rf^I$: 0.35
$Rf^{II}$: 0.65

17(c). Preparation of Z-Tyr-Ser-Leu-Ser-OCH₃

H-Ser-Leu-Ser-OCH₃ obtained in the above-mentioned step 17(b) was dissolved in 10 ml of diemthylformamide, and 0.31 ml of triethylamine was added thereto under ice-cooled condition, to this mixture was added a cold dimethylformamide solution of Z-Tyr-OSu obtained in the above-mentioned step 17(a) under stirring condition. The whole mixture was stirred at a room temperature for 18 hours, then dimethylformamide was removed by distillation under a reduced pressure, the residue was solidified by adding water, reprecipitated from methanol-ether, then from methanol-ethyl acetate to obtain 1.08 g of the desired product.

$Rf^I$: 0.78
$Rf^{II}$: 0.82

Elemental analysis (for $C_{30}H_{40}N_4O_{10}$): Calculated (%): C 58.43, H 6.54, N 9.09. Found (%): C 58.14, H 6.58, N 9.16.

17(d). Preparation of Z-Tyr-Ser-Leu-Ser-NHNH₂

1.00 Gram of Z-Tyr-Ser-Leu-Ser-OCH₃ was dissolved in methanol, then under ice-cooled condition, 0.82 ml of 100%-NH₂NH₂.H₂O was added thereto and the mixture was allowed to stand at a room temperature for 18 hours. Methanol was removed by distillation under a reduced pressure, the residue was solidified by adding ethyl ether, then washed with water to remove an excess of NH₂NH₂.H₂O, reprecipitated from methanol-ether, washed with a hot methanol to obtain 0.81 g of the desired product.

$Rf^I$: 0.45
$Rf^{II}$: 0.76

Elemental analysis (for $C_{29}H_{40}N_6O_9$): Calculated (%): C 56.48, H 6.54, N 13.63. Found (%): C 56.12, H 6.57, N 13.58.

18(a). Preparation of Z-Tyr-Ser-Leu-Ser-Thr-Asn-Leu-Gln-Glu-Ser-Leu-Arg-Ser-Lys(Tos)-Glu-OH 42.3 Milligrams of Z-Tyr-Ser-Leu-Ser-NHNH₂ was dissolved in 4 ml of dimethylformamide, further 0.34 ml of 10-hold diluted-dimethylformamide solution of 6 NOhydrochloric acid/dioxane was added thereto, and the mixture was cooled to −15° C., then 0.091 ml of 10-hold diluted-dimethylformamide solution of isoamyl nitrite was added with stirring. After the reaction mixture shows a negative reaction in hydrazine-test, 0.29 ml of 10-hold diluted-dimethylformamide solution of triethylamine was added drop by drop in small amounts to neutralize the reaction mixture. This reaction mixture containing azide product was added to 4 ml of a cold dimethylformamide solution containing 50.0 mg of H-Thr-Asn-Leu-Gln-Glu-Ser-Leu-Arg-Ser-Lys(Tos)-Glu-OH and 0.1 ml of 10-fold diluted-dimethylformamide solution of triethylamine, then the whole mixture was stirred at −10° to −15° C. for 2 hours, next at 4° C. for 18 hours. Further, a product being converted 42.3 mg of Z-Tyr-Ser-Leu-Ser-NHNH₂ into an azide was added thereto and was reacted for 24 hours. Dimethylformamide was removed by distillation under a reduced pressure, the residue obtained was extracted with 30 ml of n-butanol being saturated with water, the extract was washed 10 times with water being saturated with n-butanol, next washed 5 times with 2%-acetic acid being saturated with n-butanol. The organic layers were collected and subjected to distillation under a reduced pressure to remove n-butanol, then the residue was lyophilized, reprecipitated from ethyl acetate-ether to obtain the desired product.

18(b). Preparation of H-Tyr-Ser-Leu-Ser-Thr-Asn-Leu-Gln-Glu-Ser-Leu-Arg-Ser-Lys-Glu-OH Z-Tyr-Ser-Leu-Ser-Thr-Asn-Leu-Gln-Glu-Ser-Leu-Arg-Ser-Lys(Tos)-Glu-OH was dissolved in liquid ammonia previously dried with metallic sodium, then small pieces of metallic sodium were added to the solution with stirring until the color of the reaction mixture is changed to blue and kept it for 30 seconds to 1 minute. Further, crystals of NH₄Cl were added to the reaction mixture to neutralize an excess metallic sodium, after ammonia was completely removed by distillation at a room temperature, the reaction product was subjected to gel-filtration with Sephadex G-25 gel by using 50%-acetic acid as the eluting solvent to obtain 33 mg of the desired product. Hereinafter, this product is referred to as [Peptide H].

$Rf^I$: 0.02
$Rf^{II}$: 0.35

Elemental analysis (for $C_{74}H_{123}N_{21}O_{28}.C_2H_4O_2.4-H_2O$): Calculated (%): C 47.71, H 7.30, N 15.79. Found (%): C 47.32, H 7.24, N 15.82.

PREPARATIVE EXAMPLE C

REFERENCE EXAMPLE 1

Preparation of Z-Ser-Ser-OMe 5.06 Grams of Z-Ser-NHNH₂ was dissolved in 50 ml of dimethylformamide with 6.66 ml of 6N-hydrochloric acid/dioxane, the solution was cooled to −15° C. then 2.68 ml of isoamyl nitrite was added thereto, and the mixture was stirred for 5 minutes. Next, 5.60 ml of triethylamine was added to neutralize the reaction mixture. This reaction mixture was added to 30 ml of dimethylformamide solution containing 3.11 g of H-Ser-OMe.HCl and 2.80 ml of triethylamine, then this mixture was stirred at 4° C. for 20 hours. Dimethylformamide was removed by distillation, the residue obtained was extracted with ethyl acetate, the extract was washed with water and was dried with anhydrous sodium sulfate. After removal of ethyl acetate by distillation, the residue was crystallized by adding ether, reprecipitated from ethyl acetate-ether to obtain 3.75 g of Z-Ser-Ser-OMe.

$Rf^I$: 0.64
$Rf^{II}$: 0.77

Elemental analysis (for $C_{15}H_{20}N_2O_7$): Calculated (%): C 52.94, H 5.92, N 8.23. Found (%): C 52.67, H 5.89, N 8.35.

REFERENCE EXAMPLE 2

Preparation of Z-Arg(Tos)-Ser-Ser-OMe 2.5 Grams of Z-Ser-Ser-OMe was dissolved in 50 ml of methanol with 7.34 ml of 1N-hydrochloric acid, then in the presence of 500 mg of palladium black, catalytic reduction was carried out at 20° C., under 1 atmospheric pressure of hydrogen gas, to obtain H-Ser-Ser-OMe.HCl.

$Rf^I$: 0.08

3.39 Grams of Z-Arg(Tos)-OH was dissolved in 40 ml of tetrahydrofuran and 0.75 ml of N-methylmorpholine, then the mixture was cooled to −15° C. and 0.96 ml of isobutyl chloroformate was added thereto and stirred vigorously for 30 seconds.

H-Ser-Ser-OMe.HCl obtained as above, 20 ml of dimethylformamide and 1.03 ml of triethylamine were added and stirred for 1 minute, then stirred at 0° C. for 5 minutes, further at 40° C. for 2 minute, and at a room temperature for 15 minutes respectively. After removal of tetrahydrofuran and dimethylformamide by distillation, the residue was extracted with ethyl acetate, the extract was washed 3 times with 1N-citric acid, next washed 5 times with water, and dried with anhydrous sodium sulfate. The solvent was remove by distillation, the residue was reprecipitated from methanol-ethyl acetate to obtain 3.65 g of Z-Arg(Tos)-Ser-Ser-OMe.

$Rf^I$: 0.51
$Rf^{II}$: 0.73

Elemental analysis (for $C_{28}H_{38}N_6O_{10}S$): Calculated (%): C 51.68, H 5.88, N 12.91. Found (%): C 51.62, H 5.82, N 12.73.

REFERENCE EXAMPLE 3

Preparation of Z-Arg(Tos)-Ser-Ser-OH 3.5 Grams of Z-Arg(Tos)-Ser-Ser-OMe was dissolved in 50 ml of methanol and 10 ml of water, and 8.06 ml of 1N-sodium hydroxide was added thereto, the mixture was stirred at a room temperature for 45 minutes, next 7.24 ml of 1N-HCl was added to neutralize the reaction mixture, then methanol was removed by distillation, and the residue was extracted with n-butanol. The extract was washed with water, and n-butanol and water were removed by distillation, the residue was crystallized by adding ether, reprecipitated from methanol-ethyl acetate to obtain 2.60 g of Z-Arg(Tos)-Ser-Ser-OH.

$Rf^I$: 0.28
$Rf^{II}$: 0.57

Elemental analysis (for $C_{27}H_{36}N_6O_{10}S \cdot \frac{1}{2}H_2O$): Calculated (%): C 50.22, H 5.77, N 13.02. Found (%): C50.24, H 5.62, N 13.20.

REFERENCE EXAMPLE 4

Preparation of H-Arg(Tos)-Ser-Ser-OH 1.35 Grams of Z-Arg(Tos)-Ser-Ser-OH was dissolved in 50 ml of methanol and 10 ml of 10%-acetic acid, and the solution was subjected to catalytical reduction in the presence of 500 mg of palladium at 20° C. under an atmospheric pressure to obtain H-Arg(Tos)-Ser-Ser-OH.

$Rf^I$: 0.034

REFERENCE EXAMPLE 5

Preparation of Z-Asn-Leu-OEt 5.32 Grams of Z-Asn-OH was dissolved in 60 ml of tetrahydrofuran, 10 ml of dimethylformamide and 2.04 ml of N-methylmorpholine, to this mixture was added 40 ml of a dimethylformamide solution containing 2.64 ml of isobutyl chloroformate, 3.91 g of H-Leu-OEt.HCl and 2.80 ml of triethylamine and the reaction was carried out by a procedure similar to that described in Reference example 2. After removal of the solvent by distillation, to the residue obtained was added 1M-citric acid, the precipitate formed was collected by filtration, washed with water, dried under a reduced pressure, then was recrystallized from ethyl acetate to obtain 6.1 g of Z-Asn-Leu-OEt.

$Rf^I$: 0.71
$Rf^{II}$: 0.80

Elemental analysis (for $C_{20}H_{29}N_3O_6$): Calculated (%): C 58.95, H 7.17, N 10.31. Found (%): C 58.99, H 7.23, N 10.26.

REFERENCE EXAMPLE 6

Preparation of Z-Tyr-Asn-Leu-OEt 3.01 Grams of Z-Asn-Leu-OEt was dissolved in 50 ml of methanol and 7.4 ml of 1N-HCl, the solution was subjected to catalytical reduction in the presence of 500 mg of palladium black at a room temperature, under an atmospheric pressure to obtain H-Asn-Leu-OEt.HCl.

$Rf^I$: 0.26

H-Asn-Leu-OEt.HCl thus obtained was dissolved in 50 ml of dimethylformamide and 1.03 ml of triethylamine, then 3.35 g of Z-Tyr-ONHS was added thereto, and the mixture was allowed to stand at a room temperature for 20 hours. After removal of dimethylformamide by distillation, to the residue thus obtained was added 1M-citric acid aqueous solution, the precipitate was collected by filtration, washed with water, and reprecipitated from methanol-ethyl acetate to obtain 3.58 g of Z-Tyr-Asn-Leu-OEt.

$Rf^I$: 0.73
$Rf^{II}$: 0.82

Elemental analysis (for $C_{29}H_{38}N_4O_8$): Calculated (%): C 61.04, H 6.71, N 9.82. Found (%): C 60.84, H 6.70, N 9.39.

REFERENCE EXAMPLE 7

Preparation of Z-Tyr-Asn-Leu-NHNH$_2$ 2.78 Grams of Z-Tyr-Asn-Leu-OEt was dissolved in 30 ml of methanol, further 1.21 ml of hydrazine hydrate was added to the solution and the mixture was allowed to stand overnight, the crystals formed were collected by filtration, then washed with a small amount of methanol to obtain 3.10 g of Z-Tyr-Asn-Leu-NHNH$_2$.

$Rf^I$: 0.56
$Rf^{II}$: 0.75

Elemental analysis (for $C_{27}H_{36}N_6O_7$): Calculated (%): C 58.26, H 6.52, N 15.10. Found (%): C 57.91, H 6.56, N 15.12.

EXAMPLE 1

(a) Preparation of Boc-Leu-Gln-Arg(Tos)-Ser-Ser-OH 0.84 Grams of Boc-Leu-Gln-OH was dissolved in 30 ml of tetrahydrofuran and 0.24 ml of N-methylmorpholine, to this solution was added 0.31 ml of isobutyl chloroformate and H-Arg(Tos)-Ser-Ser-OH which was obtained in Reference example 4, and the reaction was carried out by a method similar to that described in Reference example 2. After removal of tetrahydrofuran and dimethylformamide by distillation, the residue obtained was extracted with butanol. The butanol layer was washed with 20%-acetic acid, then butanol was removed by distillation, reprecipitated from methanol-ethyl acetate to obtain 1.54 g of Boc-Leu-Gln-Arg(Tos)-Ser-Ser-OH.

$Rf^I$: 0.18
$Rf^{II}$: 0.57

Elemental analysis (for $C_{35}H_{57}N_9O_{13}S.H_2O$): Calculated (%): C 48.77, H 6.90, N 14.62. Found (%): C 48.76, H 6.61, N 14.78.

(b) Preparation of H-Leu-Gln-Arg-Ser-Ser-OH 1.50 Grams of Boc-Leu-Gln-Arg(Tos)-Ser-Ser-OH was treated with 10 ml of trifluoroacetic acid at a room temperature to remove the tert-butoxycarbonyl group therefrom, dried ether was added to the reaction mixture to crystallize the desired product to obtain H-Leu-Gln-Arg(Tos)-Ser-Ser-OH.
Rf: 0.04

H-Leu-Gln-Arg(Tos)-Ser-Ser-OH obtained as above was dissolved in 25 ml of liquid ammonia, and small pieces of metallic sodium were added to the solution. When the reaction mixture changes the color in blue, 1 g of dried ammonium chloride was added to the mixture, next ammonia was removed by distillation. The residue obtained was dissolved in 50%-acetic acid, then this solution was subjected to gel-filtration with Sephdex G-10 (2.2×85 cm, eluting solvent: 50%-acetic acid), further with LH-20 (2.2×80 cm, eluting solvent: 0.001N-HCl) to obtain a purified product of H-Leu-Gln-Arg-Ser-Ser-OH.

Hereinafter, this product is referred to as [Peptide I].
$Rf^I$: 0.01
$Rf^{II}$: 0.34
$[\alpha]_D^{20}$: −42.5° (C=0.230, 0.001N-HCl).
Elemental analysis (for $C_{23}H_{43}N_9O_9.4H_2O.CH_3COOH$): Calculated (%): C 41.60, H 7.68, N 17.46. Found (%): C 41.20, H 7.93, N 17.91.

EXAMPLE 2

(a) Preparation of
Z-Phe-Leu-Gln-Arg(Tos)-Ser-Ser-OH

H-Leu-Gln-Arg(Tos)-Ser-Ser-OH obtained in Example 1 (b) was dissolved in 30 ml of dimethylformamide and 0.24 ml of triethylamine, then 0.77 g of Z-Phe-ONHS was added thereto, and the mixture was allowed to stand at a room temperature for 20 hours. After removal of dimethylformamide by distillation, the residue was extracted with butanol, and the extract was washed with 2%-acetic acid. The butanol layer was concentrated, and the concentrate obtained was crystallized by adding ether, the crystals were collected by filtration and washed with a hot ethanol to obtain 1.40 g of Z-Phe-Leu-Gln-Arg(Tos)-Ser-Ser-OH.
$Rf^I$: 0.22
$Rf^{II}$: 0.59
Elemental analysis (for $C_{47}H_{64}N_{10}O_{14}S.H_2O$): Calculated (%): C 54.12, H 6.28, N 13.43. Found (%): C 54.42, H 6.38, N 13.84.

(b) Preparation for H-Phe-Leu-Gln-Arg-Ser-Ser-OH

20 Milligrams of Z-Phe-Leu-Gln-Arg(Tos)-Ser-Ser-OH was treated with metallic sodium in liquid ammonia to remove a group of the formula Z, and a group of the formula Tos, by a method similar to that described in Example 1 (b), then the reaction mixture was subjected to a gel-filtration by using Sephadex G-10 (2.2×85 cm, eluting solvent: 10%-acetic acid), then by using LH-20 (2.2×80 cm, eluting solvent: 0.001N-HCl) to obtaine 12 mg of a purified product of H-Phe-Leu-Gln-Arg-Ser-Ser-OH. Hereinafter, this product is referred to as [Peptide J].
$Rf^I$: 0.01
$Rf^{II}$: 0.35

$[\alpha]_D^{20}$: −37.3° (C=0.249, 0.001N-HCl)
Elemental analysis (for $C_{32}H_{52}N_{10}O_{10}.7H_2O.CH_3COOH$): Calculated (%): C 44.24, H 7.64, N 15.17. Found (%): C 44.27, H 7.10, N 15.60.

EXAMPLE 3

(a) Preparation of
Z-Leu-Gly-Phe-Leu-Gln-Arg(Tos)-Ser-Ser-OH 0.39 Gram of Z-Leu-Gly-NHNH$_2$ was dissolved in 5 ml of dimethylformamide and 0.58 ml of 6N HCl/dioxane, then a reaction similar to that described in Reference example 1 was carried out by using 10 ml of a dimethylformamide solution containing 0.15 ml of isoamyl nitrite, 0.49 ml of triethylamine and 1.00 g of H-Phe-Leu-Gln-Arg(Tos)-Ser-Ser-OH, further an equivalent amount of Z-Leu-Gly-N$_3$ was added to the reaction mixture and reacted at 4° C. for 20 hours. The reaction mixture was extracted with butanol, the extract was washed with 2%-acetic acid, then butanol and acetic acid were removed by sistillation, the residue was crystallized from ether. The crystals were collected by filtration and washed with a hot methanol to obtain 0.65 g of Z-Leu-Gly-Phe-Leu-Gln-Arg(Tos)-Ser-Ser-OH.
$Rf^I$: 0.19
$Rf^{II}$: 0.60
Elemental analysis (for $C_{55}H_{78}N_{12}O_{16}S.H_2O$): Calculated (%): C 54.44, H 6.64, N 13.85. Found (%): C 54.74, H 6.66, N 13.98.

(b) Preparation of
H-Leu-Gly-Phe-Leu-Gln-Arg-Ser-Ser-OH

20 Milligrams of Z-Leu-Gly-Phe-Leu-Gln-Arg(Tos)-Ser-Ser-OH was treated by a method similar to that described in Example 1 (b) to remove a group of the formula Z and to remove a group of the formula Tos, then the reaction mixture was subjected to a gel-filtration by using Sephadex G-10 (2.2×85 cm, eluting solvent: 10%-acetic acid), and by using LH-20 (2.2.×80 cm, eluting solvent: 0.001N-HCl), to obtain 11 mg of H-Leu-Gly-Phe-Leu-Gln-Arg-Ser-Ser-OH. Hereinafter, this product is referred to as [Peptide K].
$Rf^I$: 0.01
$Rf^{II}$: 0.40
$[\alpha]_D^{20}$: −27.6° (C=0.228, 0.001N-HCl)
Elemental analysis (for $C_{40}H_{66}N_{12}O_{12}.6H_2O.CH_3COOH$): Calculated (%): C 46.92, H 7.68, N 15.63. Found (%): C 46.89, H 7.25, N 15.51.

EXAMPLE 4

(a) Preparation of
H-Tyr-Asn-Leu-Leu-Gly-Phe-Leu-gln-Arg(Tos)-Ser-Ser-OH

600 Milligrams of Z-Leu-Gly-Phe-Leu-Gln-Arg(Tos)-Ser-Ser-OH was dissolved in 50 ml of methanol and 10 ml of 10%-acetic acid, then the mixture was subjected to catalytic reduction in the presence of 500 mg of palladium at a room temperature under an atmospheric pressure to obtain H-Leu-Gly-Phe-Leu-Gln-Arg(Tos)-Ser-Ser-OH.
$Rf^I$: 0.18

420 Milligrams of Z-Tyr-Asn-Leu-NHNH$_2$ was dissolved in 5 ml of dimethylformamide and 0.37 ml of 6N-HCl/dioxane, then by using 0.10 ml of isoamyl nitrite and 0.31 ml of triethylamine, an azide product was prepared by a method similar to that described in Reference example 1, the reaction mixture was added to a mixture of 10 ml of hexamethylphosphoric triamide of H-Leu-Gly-Phe-Leu-Gln-Arg(Tos)-Ser-Ser-OH with 10 ml of dimethylformamide, then the whole mixture was stirred at 4° C. for 20 hours. Dimethylformamide was removed by distillation, the residue obtained was extracted with butanol, the extract was washed with 2%-acetic acid, butanol was removed by distillation, the residue was crystallized by adding ether. Thus obtained Z-Tyr-Asn-Leu-Leu-Gly-Phe-Leu-Gln-Arg(Tos)-Ser-Ser-OH was dissolved in 30 ml of methanol and 10 ml of 10%-acetic acid, and the solution was subjected to catalytic reduction in the presence of palladium at a room temperature, under an atmospheric pressure, the reaction mixture was subjected to a gel-filtration by using Sephdex G-25 (3×120 cm, eluting solvent: 50%-acetic acid) to obtain 650 mg of H-Tyr-Asn-Leu-Leu-gly-Phe-Ley-Gln-Arg(Tos)-Ser-Ser-OH.

$Rf^I$: 0.05
$Rf^{II}$: 0.53

Elemental analysis (for $C_{66}H_{98}N_{16}O_{19}S \cdot 2H_2O$): Calculated (%): C 53.28, H 6.91, N 15.06. Found (%): C 53.10, H 6.43, N 14.84.

(b) Preparation of
H-Tyr-Asn-Leu-Gly-Phe-Leu-Gln-Arg-Ser-Ser-OH

H-Tyr-Asn-Leu-Leu-Gly-Phe-Leu-Gln-Arg(Tos)-Ser-Ser-OH obtained in Example 4 (a) as above was treated by a method similar to that described in Example 1 (b) to remove a group of the formula Tos, then the reaction mixture was subjected to gel-filtration by using Sephadex G-10 (2.2.×85 cm, eluting solvent: 10%-acetic acid), further using LH-20 (2.2×80 cm, eluting solvent: 0.001N-HCl), to obtain 9 mg of a purified product of H-Tyr-Asn-Leu-Leu-Gly-Phe-Leu-Gln-Arg-Ser-Ser-OH. Hereinafter, this product is referred to as [Peptide L].

$Rf^I$: 0.01
$Rf^{II}$: 0.42
$[\alpha]_D^{20}$: −24.3° (C=0.078, 0.001N-HCl)

Elemental analysis (for $C_{59}H_{92}N_{10}O_{17} \cdot 15H_2O \cdot CH_3COOH$): Calculated (%): C 45.01, H 7.80, N 13.77. Found (%): C 45.21, H 7.31, N 14.22.

EXAMPLE 5

(a) Preparation of
Z-Met-Ser-Tyr-Asn-Leu-Leu-Gly-Phe-Leu-Gln-Arg(Tos)-Ser-Ser-OH 159 Milligrams of Z-Met-Ser-NHNH$_2$ was dissolved in 5 ml of dimethylformamide and 0.21 ml of 6N-HCl/dioxane, then by using 0.055 ml of isoamyl nitrite and 0.17 ml of triethylamine, an azide product was prepared by a method similar to that described in Reference example 1, this reaction mixture was added to a mixture of 300 mg of H-Tyr-Asn-Leu-Leu-Gly-Phe-Leu-Gln-Arg(Tos)-Ser-Ser-OH, 5 ml of dimethylformamide and 5 ml of hexamethylphosphoric triamide, then the whole mixture was stirred at 4° C. for 24 hours. Further, 318 mg of Z-Met-Ser-NHNH$_2$ was added thereto and stirred at 4° C. for 72 hours. By a method similar to that described in Example 4 (a), purification was conducted to obtain Z-Met-Ser-Tyr-Asn-Leu-Leu-Gly-Phe-Leu-Gln-Arg(Tos)-Ser-Ser-OH.

(b) Preparation of
H-Met-Ser-Tyr-Asn-Leu-Leu-Gly-Phe-Leu-Gln-Arg-Ser-Ser-OH

Z-Met-Ser-Tyr-Asn-Leu-Leu-Gly-Phe-Leu-Gln-Arg Arg(Tos)-Ser-Ser-OH was treated by a method similar to that described in Example 1 (b) to remove a group of the formula Z, and to remove a group of the formula Tos, then the reaction mixture was subjected to purification by using Sephadex G-25 (3×120 cm, eluting solvent: 50% -acetic acid), further using LH-20 (2×85 cm, eluting solvent: 0.001N-HCl), to obtain 119 mg of H-Met-Ser-Tyr-Asn-Leu-Leu-Gly-Phe-Leu-Gln-Arg-Ser-Ser-OH. Hereinafter, this product is referred to as [Peptide M].

$Rf^I$: 0.01
$Rf^{II}$: 0.45
$[\alpha]_D^{20}$: −15.7° (C=0.254, 0.001N-HCl)

Elemental analysis (for $C_{67}H_{106}N_{18}O_{20}S \cdot 5H_2O \cdot CH_3COOH$): Calculated (%): C 49.75, H 7.26, N 15.13. Found (%): C 49.80, H 6.92, N 14.91.

Amino acid analysis: Asp: 0.93, Ser: 3.15, Gln: 1.03, Met: 0.92, Gly: 1.05, Leu: 3.08, Tyr: 1.00, Phe: 0.98, Arg: 0.96.

[Preparation of labelled peptides]

Preparative example of labelled peptide-1

H-Tyr-Ser-Asp-Leu-Pro-Gln-Thr-His-Ser Leu-Asn-Arg-Arg-Ala-Leu-Ile-Leu-Leu-Ala-Gln-OH, i.e., Peptide D was labelled by a method using Chloramine-T as follows.

To 20 microliters of 0.5M-phosphate buffer solution (pH 7.0) containing 5 micrograms of the above-mentioned peptide [Peptide D] was added 0.5M-phosphate buffer solution containing 1 microcurie of Na[$^{125}$I] [carrier free, New England Nuclear (N.E.N.)], then 20 microliters of 0.5M-phosphate buffer solution containing 70 mg/ml of Chloramine-T was added. The mixture was stirred at a room temperature for 30 seconds, the reaction was terminated by adding 50 microliters of 0.5M-phosphate buffer solution containing 60 mg/ml of sodium metabisulphite (Na$_2$S$_2$O$_5$). Then, to this reaction mixture was added 100 microliters of cold 1%-sodium iodide aqueous solution, this reaction mixture was treated by a Sephdex G-25 column (1.0×30 cm) (eluting solvent: 0.05M-phosphate buffer, pH 7.4, containing 0.25% of BSA, 10 mM of EDTA and 0.02% of NaN$_3$). There is obtained the labelled peptide D wherein the 13th and the 14th fractions were labelled with $^{125}$I. Hereinafter, this product is referred to as [$^{125}$I labelled-Peptide D].

Preparative example of labelled peptide-2-

H-Tyr-Ser-Leu-Ser-Thr-Asn-Leu-Gln-Glu-Ser-Leu-Arg-Ser-Lys-Glu-OH, i.e., Peptide H was labelled by a method using Chloramine-T as follows.

To 20 microliters of 0.5M-phosphate buffer solution (pH 7.0) containing 5 micrograms of the above-mentioned peptide [Peptide H] was added 0.5M-phosphate buffer solution containing 1 microcurie of Na[$^{125}$I] (carrier free N.E.N.), then 20 microliters of 0.5M-phosphate buffer solution containing 70 mg/ml of Chloramine-T was added. The mixture was stirred at a room temperature for 30 seconds, the reaction was terminated by adding 50 microliters of 0.5M-phosphate buffer solution containing 60 mg/ml of sodium metabisulphite (Na$_2$S$_2$O$_5$). Then, to this reaction mixture was added 100 microliters of cold 1%-sodium iodide aqueous solution, the reaction mixture was treated by using Sephadex G-25 column (1.0×30 cm) (eluting liquor: 0.05M-phosphate buffer solution, pH 7.4, containing 0.25% of BSA, 10 mM of EDTA and 0.02% of NaN$_3$). There is obtained peptide H being labelled with $^{125}$I. Hereinafter, this product is referred to as [$^{125}$I labelled-Peptide H].

Preparative example of labelled peptide-2-2

To 20 microliters of 0.5M-phosphate buffer solution (pH 7.0) containing 5 micrograms of Peptide H was added 0.5M-phosphate buffer solution containing 1 millicurie of Na[$^{125}$I] (carrier free N.E.N.), then 20 microliters of 0.5M-phosphate buffer solution containing 70 mg/ml of Chloramine-T was added. The mixture was stirred at a room temperature for 30 seconds, the reaction was terminated by adding 50 microliters of 0.5M-phosphate buffer solution containing 60 mg/ml of sodium metabisulphite ($Na_2S_2O_5$). Then, to this reaction mixture was added 100 microliters of cold 1%-sodium iodide aqueous solution, and was treated by using Sephadex G-25 column (1.0×30 cm) (eluting solvent: 0.05M-phosphate buffer solution, pH 7.4, containing 0.25% of BSA, 10 mM of EDTA and 0.02% of $NaN_3$). There is obtained $^{125}$I labelled-Peptide H.

Preparative example of labelled peptide-3

(1)

H-Met-Ser-Tyr-Asn-Leu-Leu-Gly-Phe-Leu-Gln-Arg-Ser-Ser-Oh, i.e., Peptide M was labelled by a method using Chloramine-T as follows To 20 microliters of 0.2M-phosphate buffer solution (pH 7.4) containing 5 micrograms of the above-mentioned peptide [Peptide M] was added 0.2M-phosphate buffer solution containing 1 microcurie of Na[$^{125}$I] (N.E.N.), then 20 microliters of 0.2M-phosphate buffer solution containing 3.5 mg/ml of Chloramine-T was added. This mixture was allowed to stand at a room temperature for 20 seconds, then the reaction was terminated by adding 50 microliters of 0.2M-phosphate buffer solution containing 2.4 mg/ml of sodium metabisulphite. The reaction mixture was treated by using DEAE-Sephadex A-25 column (1.0×30 cm) (eluting solvent: 0.1M-trishydrochloric acid buffer solution, pH 8.6, containing 0.1% of BSA and 0.01% of $NaN_3$). The first fraction of the peptide was purified by an ion-exchange chromatography to obtain $^{125}$I labelled peptide. Hereinafter, this product is referred to as [$^{125}$I labelled Peptide M].

(2)

H-Met-Ser-Tyr-Asn-Leu-Leu-Gly-Phe-Leu-Gln-Arg-Ser-Ser-OH, i.e., Peptide M was labelled by a method using Chloramine-T as follows To 20 microliters of 0.2M-phosphate buffer solution (pH 7.4) containing 5 micrograms of the above-mentioned peptide [Peptide M] was added 0.2M-phosphate buffer solution containing 1 microcurie of Na[$^{125}$I] (N.E.N.), then 20 microliters of 0.2M-phosphate buffer solution containing 3.5 mg/ml of Chloramine-T was added, This mixture was allowed to stand at a room temperature for 20 seconds, then the reaction was terminated by adding 50 microliters of 0.2M-phosphate buffer solution containing 2.4 mg/ml of sodium metadisulphite. The reaction mixture was treated by using SP-Sephadex C-25 column (1.0×30 cm) (eluting solvent: 50 mM-phosphate buffer solution). There is obtained the above-mentioned Peptide M wherein the 4th fraction was labelled with $^{125}$I. Hereinafter, this product is also referred to as [$^{125}$I labelled-Peptide M].

Preparative Example of Labelled Peptide-4

(1) 1 Milligram of peptide C and 1 milligram of fluorescene isothiocyanate (FITC) were dissolved in 0.2M-sodium borate buffer solution (pH 9.5). After the reaction being carried out for 1 hour at a room temperature, the reaction mixture was treated by silica gel-thin layer chromatography (TLC) (eluting solvent=butanol:acetic acid:water=4:1:5). Isolated spots obtained from the TLC were collected, and were washed with methanol, then with ethanol, and eluted with above-mentioned buffer solution (pH 7.8) to obtain 0.3 mg of FITC labelled peptide. Hereinafter, this product is referred to as [FITC labelled Peptide C].

$Rf^I$: 0.11
$Rf^{II}$: 0.50

Elemental analysis (for $C_{116}H_{174}N_{32}O_{34}S \cdot 2CH_3COOH \cdot 7H_2O$): Calculated (%): C 50.77, H 6.96, N 15.79. Found (%): C 49.99, H 6.85, N 15.50.

(2) 1 Milligram of Peptide C was dissolved in 1 ml of 0.2M-sodium bicarbonate buffer solution (pH 9.5). Then, 1 mg of tetramethylrhodamine isothiocyanate (TRITC) was dissolved in the above-mentioned buffer solution, and was combined with the above-mentioned peptide solution at 0° C. After completion of the reaction being held at a room temperature for 1 hour, the reaction mixture was subjected to a silica gel-TLC (eluting solvent=butanol:acetic acid:water=4:1:5). Isolated spots obtained from the TLC were collected, and were washed with the above-mentioned buffer solution to obtain 0.2 mg of TRITC labelled-peptide. Hereinafter, this product is referred to as [TRITC labelled-Peptide C].

$Rf^I$: 0.08

Elemental analysis: (for $C_{120}H_{184}N_{34}O_{33}S \cdot 2CH_3COOH \cdot 7H_2O$): Calculated (%): C 51.19, H 7.14, N 16.37. Found (%): C 50.08, H 7.02, N 16.19.

Preparative Exampel of Labelled Peptide-5

(1) 1 Milligram of Peptide G was dissolved in 1 ml of 0.2M-sodium bicarbonate buffer solution (pH=9.5). Then 1 mg of FITC was added thereto and reacted at 25° C. for 1 hour. After completion of the reaction, the reaction mixture was subjected to a silica gel-TLC (eluting solvent=butanol:acetic acid:water=4:1:5) to purify the product and 0.1 mg of FITC labelled-peptide was obtained. Hereinafter, this product is referred to as [FITC labelled-Peptide G].

$Rf^I$: 0.13
$Rf^{II}$: 0.49

(2) 1 Milligram of Peptide G was dissolved in 1 ml of 0.2M-sodium bicarbonate buffer solution (pH-9.5). Then 1 mg of dichlorotriazinefluorescein was added there thereto, and the reaction was carried out at 25° C. for 1 hour. Then the reaction mixture was treated by a silica gel-TLC (eluting solvent=butanol:acetic acid:water=4:1:5). There is obtained 0.1 mg of a purified product of DTAF labelled peptide. Hereinafter, this product is referred to as [DTAF labelled-Peptide-G].

$Rf^I$: 0.12

Preparative Example of Labelled Peptide-6

(1) 1 Milligram of Peptide M and 1 mg of FITC were dissolved in 0.2M-sodium bicarbonate buffer 50% v/v methanol solution (pH-9.5). The reaction was carried out at a room temperature for 2 hours, then the reaction mixture was subjected to a silica gel-TLC (eluting solvent=butanol:acetic acid:water=4:1:5). Isolated spots obtained from the TLC were collected, eluted with methanol to obtain 0.3 mg of FITC labelled peptide. Hereinafter, this product is referred to as [FITC labelled-Peptide M].

Rf$^I$: 0.16
Rf$^{II}$: 0.52
Elemental analysis (for $C_{88}H_{117}N_{19}O_{25}S_2.5H_2O$ $CH_3COOH$): Calculated (%): C 52.60, H 6.42, N 12.95. Found (%); C 52.65, H 6.22, N 12.74.

(2) 1 Milligram of Peptide M was dissolved in 0.05 ml of 0.001N-hydrochloric acid, this solution was mixed with 0.2M-sodium bicarbonate buffer 50% v/v methanol solution (pH=9.5). On the other hand, 1 mg of TRITC was dissolved in 0.2M-sodium bicarbonate buffer solution (pH 9.5), then this solution was mixed with the peptide solution. The reaction was carried out at a room temperature for 2 hours, then the reaction mixture was treated by a silica gel-TLC (eluting solvent=butanol:acetic acid:water=4:1:5). Isolated spots were collected and eluted with methanol to obtain 0.1 mg of TRITC labelled peptide. Hereinafter, this produce is referred to as [TRITC labelled-Peptide M].
Rf$^I$: 0.12
Rf$^{II}$: 0.42
Elemental analysis (for $C_{92}H_{127}N_{21}O_{24}S_2 \cdot 5H_2O$. $CH_3COOH$): Calculated (5): C 53.12, H 6.69, N 13.84. Found (%): C 53.20, H 6.51, N 18.80.

[Preparation of antigen]

PREPARATIVE EXAMPLE 1

5 Milligrams of Peptide-A which was prepared in Preparative Exampel A-1 of Synthesis of peptide, and 15 mg of bovine serum albumin (hereinafter referred to as [BSA]) were dissolved in 2 ml of 0.1M-ammonium acetate buffer solution (pH 7.0). To this solution was added 0.11 ml of 0.1N-glutaraldehyde solution, and the mixture was stirred at a room temperature for 5 hours. Then this reaction mixture was dialyzed with 1 liter of water at 4° C. for 48 hours. During the dialysis water was changed 5 times. The dialyzed solution containing peptideprotein composition was lyophilized to obtain 18 mg of human interferon-α antigen (hereinafter, this product is referred to as [Antigen α-N-I]).

This Antigen α-N-I is an antigen in which an average 12 moles of the Peptide-A is combined with 1 mole of BSA.

PREPARATIVE EXAMPLE 2

5 Milligrams of Peptide-β which was prepared in Preparative Example A-2 of Synthesis of peptide, and 20 mg of BSA were dissolved in 2 ml of 0.1M-ammonium acetate buffer solution (pH 7.0). To this solution was added 0.11 ml of 0.1M-glutaraldehyde solution, and the mixture was stirred at a room temperature for 5 hours. Then this reaction mixture was dialyzed with 1 liter of water at 4° C. for 48 hours. During the dialysis water was changed 5 times. The dialyzed solution containing peptide-protein composition was lyophilized to obtain 23 mg of human interferon-α antigen (hereinafter, this product is referred to as [Antigen α-N-II]).

This Antigen α-N-II is an antigen in which an average 9 moles of the Peptide-B is combined with 1 mole of BSA.

PREPARATIVE EXAMPLE 3

4.5 Milligrams of Peptide-C which was prepared in Preparative example A-3 of Synthesis of peptide, and 25 mg of BSA were dissolved in 2 ml of 0.1M-ammonium acetate buffer solution (pH 7.0). To this solution was added 1.0 ml of 0.1M-glutaraldehyde solution, and the mixture was stirred at a room temperature for 5 hours. Then this reaction mixture was dialyzed with 1 liter of water at 4° C. for 48 hours. During the dialysis water was chaned 5 times. The dialyzed solution containing peptide-protein composition was lyophilized to obtain 27 mg of human interferon-α antigen (hereinafter, this produce is referred to as [Antigen α-N-III]).

This Antigen α-N-III as an antigen in which an average 10 moles of the Peptide-C is combined with 1 mole of BSA.

PREPARATIVE EXAMPLE 4

5 Milligrams of Peptide-D which was prepared in Preparative Example A-4 of Synthesis of peptide, and 25 mg of BSA were dissolved in 2 ml of 0.1M-ammonium acetate buffer solution (pH 7.0). To this solution was added 0.11 ml of 0.1M-glutaraldehyde solution, and the mixture was stirred at a room temperature for 5 hours. Then this reaction mixture was dialyzed with 1 liter of water at 4° C. for 48 hours. During the dialysis water was changed 5 times. The dialysed solution containing peptide-protein composition was lyophilized to obtain 28 mg of human interferon-α antigen (hereinafter, this pr product is referred to as [Antigen α-N-IV]).

This Antigen α-N-IV is an antigen in which an average 9 moles of the Peptide-D is combined with 1 mole of BSA.

PREPARATIVE EXAMPLE 5

4.5 Milligrams of Peptide-C which was prepared in Preparative Example A-3 of Synthesis of peptide, and 25 mg of BSA were dissolved in 4 ml of water. To this solution was added 200 mg of dicyclohexylcarbodiimide (DCC), and the mixture was stirred at a room temperature for 5 hours. Then this reaction mixture was dialyzed with 2 liters of water at 4° C. for 48 hours. During the dialysis water was changed 5 times. The dialysed solution containing peptide-protein composition was lyophilized to obtain 27.5 mg of human interferonantigen (hereinafter, this product is referred to as [Antigen α-N-V]).

This Antigen α-N-V is an antigen in which an average 12 moles of the Peptide-C is combined with 1 mole of BSA.

PREPARATIVE EXAMPLE 6

4.5 Milligrams of Peptide-D which was prepared in Preparative Example A-4 of Synthesis of peptide, and 25 mg of BSA were dissolved in 4 ml of water. To this solution was added 200 mg of dicyclohexylcarbodiimide (DCC)), and the mixture was stirred at a room temperature for 5 hours. Then this reaction mixture was dialyzed with 2 liters of water at 4° C. for 48 hours. During the dialysis water was changed 5 times. The dialysed solution containing peptide-protein composition was lyophilized to obtain 29 mg of human interferon-α antigen (hereinafter, this product is referred to as [Antigen α-N-VI]).

Thus obtained Antigen α-N-VI is an antigen in which an average 9 moles of the Peptide-D is combined with 1 mole of BSA.

PREPARATIVE EXAMPLE 7

5 Milligrams of Peptide-E which was prepared in Preparative Example B-7 (c) of Synthesis of peptide, and 15 mg of BSA were dissolved in 2 ml of 0.1 M-ammonium acetate buffer solution (pH 7.0). To this solution was added 0.11 ml of 0.1M-glutaraldehyde solution, and the mixture was stirred at a room temperature for 5 hours. Then this reaction mixture was dialyzed with 1 liter of water at 4° C. for 48 hours. During the dialysis, water was changed 5 times. The dialyzed solution containing peptide-protein composition was lyophilized to obtain 15 mg of human interferon-α antigen (hereinafter, this product is referred to as [Antigen α-C-I]).

This Antigen-α-C-I is an antigen in which an average 10 moles of the Peptide-E is combined with 1 mole of BSA.

The combination ratio of Peptide-E to BSA in the Antigen α-C-I was calculated as follows, in that, after confirming the absence of either unreacted BSA or unreacted Peptide-E in the Antigen α-C-I by subjecting to additional ge-filtration using Sephadex G-50 (eluting solvent: phsiological saline solution; determination: OD 280 nm; eluting velocity: 3 ml/hour; separating amount: 1 milliliter each), then separating and determining the amount of a fraction of Peptide-E being combined with BSA (a peptide-protein composition), and a fraction of other product (a dimer of Peptide-E) respectively, preparing a calibration curve of the standard concentration of said dimer of Peptide-E for the purpose of determining the amount of the dimer, substrating the amount of the dimer from the amount of the Peptide-E which was used as the starting material, the substracted value of the amount of the Peptide-E is considered as all the amount of the Peptide-E being combined with BSA.

The combination ratio of a synthetic peptide to BSA in each of antigens obtained in the respective preparative examples in the present invention is calculated similarly.

PREPARATIVE EXAMPLE 8

5 Milligrams of Peptide-F which was prepared in Preparative Example B-12 of Synthesis of peptide, and 5 mg of BSA were dissolved in 2 ml of 0.1M-ammonium acetate buffer solution (pH 7.0). To this solution was added 0.11 ml of 0.1M-glutaraldehyde solution, and the mixture was stirred at a room temperature for 5 hours. Then this reaction mixture was dialyzed with 1 liter of water at 4° C. for 48 hours. During the dialysis, water was changed 5 times. The dialyzed solution containing peptide-protein composition was lyophilized to obtain 9 mg of human interferon-α antigen (hereinafter, this product is referred to as [antigen α-C-II]).

This Antigen α-C-II is an antigen in which an average 9 moles of the Peptide-F is combined with 1 mole of BSA.

PREPARATIVE EXAMPLE 9

5 Milligrams of Peptide-G which was prepared in Preparative Example B-16 (b) of Synthesis of peptide, and 25 mg of BSA were dissolved in 4 ml of water. To this solution was added 200 mg of dicyclohexylcarbodiimide (DCC), and the mixture was stirred at a room temperature for 5 hours. Then this reaction mixture was dialyzed with 2 liters of water at 4° C. for 48 hours. During the dialysis, water was changed 5 times. The dialyzed solution containing peptide-protein composition was lyophilized to obtain 28 mg of human interferon-α antigen (hereinafter, this product is referred to as [Antigen α-C-III]).

The Antigen α-C-III obtained is an antigen in which an average 12 moles of the Peptide-G is combined with 1 mole of BSA.

PREPARATIVE EXAMPLE 10

4 Milligrams of Peptide-H which was prepared in Preparative Example B-18 (b) of Synthesis of peptide, and 20 ml of BSA were dissolved in 0.1M-ammonium acetate buffer solution (pH 7.0). To this solution was added 0.11 ml of 0.1M-glutaraladehyde solution, and the mixture was stirred at a room temperature for 5 hours. This reaction mixture was dialyzed with 1 liter of water at 4° C. for 48 hours. During the dialysis, water was changed 5 times. The dialyzed solution containing peptide-protein composition was lyophilized to obtain 22 mg of human interferon-α antigen (hereinafter, this product is referred to as [Antigen α-C-IV]).

The Antigen α-C-IV is an antigen in which an average 9 moles of Peptide-H is combined with 1 mole of BSA.

PREPARATIVE EXAMPLE 11

4 Milligrams of Peptide-G which was prepared in Preparative Example B-16 (b) of Synthesis of peptide, and 20 mg of BSA were dissolved in 0.1M-ammonium acetate buffer solution (pH 7.0). To this solution was added 0.11 ml of 0.1M-glutaraldehyde solution, and stirred at a room temperature for 5 hours. Then this reaction mixture was dialyzed with 1 liter of water at 4° C. for 48 hours. During the dialysis water was changed 5 times. The dialyzed solution containing peptide-protein composition was lyophilized to obtain 21 mg of human interferon-α antigen (hereinafter, this product is referred to as [Antigen α-C-V]).

The Antigen α-C-V obtained is an antigen in which an average 8 moles of the Peptide-G is combined with 1 mole of BSA.

PREPARATIVE EXAMPLE 12

10 Milligrams of Peptide-I which was prepared in Preparative Example C-1 (b) of Synthesis of peptide, and 50 mg of BSA were dissolved in 2 ml of 0.1M-ammonium acetate buffer solution (pH 7.0). To this solution was added 0.11 ml of 0.1M-glutaraldehyde solution, and stirred at a room temperature for 5 hours. Then this reaction mixture was dialyzed with 1 liter of water. During the dialysis, water was changed 5 times. The dialyzed solution containing peptide-protein composition was lyophilized to obtain 45 mg of human interferon-β antigen (hereinafter, this product is referred to as [Antigen β-I]).

PREPARATIVE EXAMPLE 13

5 Milligrams of Peptide-J which was prepared in Preparative Example C-2 (b) of Synthesis of peptide, and 20 mg of BSA were dissolved in 2 ml of 0.1M-ammonium acetate buffer solution (pH 7.0). To this solution was added 0.11 ml of 0.1M-glutaraldehyde solution, and the mixture was stirred at a room temperature for 5 hours. This reaction mixture was dialyzed with 1 liter of water at 4° C. for 48 hours. During the dialysis, water was changed 5 times. The dialyzed solution containing peptide-protein composition was lyophilized to obtain 23 mg of human interferon-β antigen (hereinafter, this product is referred to as [Antigen β-II]).

PREPARATIVE EXAMPLE 14

4 Milligrams of Peptide-K which was prepared in Preparative Example C-3 (b) of Synthesis of peptide, and 15 mg of BSA were dissolved in 2 ml of 0.1M- ammonium acetate buffer solution (pH 7.0). To this solution was added 0.11 ml of 0.1M-glutaraldehyde solution, and the mixture was stirred at a room temperature for 5 hours. Then, this reaction mixture was dialyzed with 1 liter of water at 4° C. for 48 hours. During the dialysis, water was changed 5 times. The dialyzed solution containing peptide-protein composition was lyophilized to obtain 17 mg of human interferon-$\beta$ antigen (hereinafter, this product is referred to as [Antigen $\beta$-III]).

PREPARATIVE EXAMPLE 15

4 Milligrams of Peptide-L which was prepared in Preparative Example C-4 (b) of Synthesis of peptide, and 12 mg of BSA were dissolved in 2 ml of 0.1M-ammonium acetate buffer solution (pH 7.0). To this solution was added 0.11 ml of 0.1M-glutaraldehyde solution, and the mixture was stirred at a room temperature for 5 hours. This reaction mixture was dialyzed at 4° C. for 48 hours. During the dialysis, water was changed 5 times. The dialyzed solution containing peptide-protein composition was lyophilized to obtain 14 mg of human interferon-$\beta$ antigen (hereinafter, this product is referred to as [Antigen $\beta$-IV]).

PREPARATIVE EXAMPLE 16

8 Milligrams of Peptide-M which was prepared in Preparative Example C-5 (b) of Synthesis of peptide, and 25 mg of BSA were dissolved in 2 ml of 0.1M-ammonium acetate buffer solution (pH 7.0). To this solution was added 0.11 ml of 0.1M-glutaraldehyde solution, and the mixture was stirred at a room temperature for 5 hours. Then this reaction was dialyzed with 1 liter of water at 4° C. for 48 hours. During the dialysis, water was changed 5 times. The dialyzed solution containing peptide-protein composition was lyophilized to obtain 31 mg of human interferon-$\beta$ antigen (hereinafter, this product is referred to as [Antigen $\beta$-V]).

PREPARATIVE EXAMPLE 17

8 Milligrams of Peptide-M which was prepared in Preparative Example C-5 (b) of Synthesis of peptide, and 25 mg of BSA were dissolved in 4 ml of water. To this solution was added dicyclohexylcarbodiimide (DCC), and the mixture was stirred at a room temperature for 5 hours. Then this reaction mixture was dialyzed with 2 liters of water at 4° C. for 48 hours. During the dialysis, water was changed 5 times. The dialyzed solution containing peptide-protein composition was lyophilized to obtain 29 mg of human interferon-$\beta$ antigen (hereinafter, this product is referred to as [Antigen $\beta$-VI]).

[Preparative of antibody]

PREPARATIVE EXAMPLE 1

100 Micrograms of Antigen $\alpha$-N-1 which was obtained in Preparative Example 1 of Preparation of antigen was dissolved in 1.5 ml of physiological saline solution, then to this solution was added 1.5 ml of a complete Freund's adjuvant to prepare a suspension. This suspension was administered subcutaneously to three rabbits (each of which having 2.5 to 3.0 kg of body weight) respectively, and the same amount of the suspension was administered to the same rabbit in every other weeks in 6 times. Further, the same amount of the suspension was additionally administered to the same rabbit in every month in 3 times. 7 Days after the last administration of the suspension, the blood was taken out from the test animal. The blood was subjected to a centrifugal separation to obtain the serum which contains human interferon-$\alpha$ antibody (hereinafter, this product is referred to as [Antibody $\alpha$-N-I]).

PREPARATIVE EXAMPLE 2

20 Micrograms of Antigen $\alpha$-N-II which was obtained in Preparative Example 2 of Preparation of antigen was dissolved in 1.5 ml of physiological saline solution, then to this solution was added 1.5 ml of a complete Freund's adjuvant to prepare a suspension. This suspension was administered subcutaneously to seven rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the test animal. The blood was subjected to a centrifugal separation to obtain the serum which contains human interferon-$\alpha$ antibody (hereinafter, this product is referred to as [Antibody $\alpha$-N-II]).

PREPARATIVE EXAMPLE 3

20 Micrograms of Antigen $\alpha$-N-III which was obtained in Preparative Example 3 of Preparation of antigen was dissolved in 1.5 ml of physiological saline solution, then to this solution was added 1.5 ml of a complete Freund's adjuvant to prepare a suspension. This suspension was administered subcutaneously to seven rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the test animal. The blood was subjected to a centrifugal separation to obtain the serum which contains human interferon-$\alpha$ antibody (hereinafter, this product is referred to as [Antibody $\alpha$-N-III]).

PREPARATIVE EXAMPLE 4

100 Micrograms of Antigen $\alpha$-N-III which was obtained in Preparative Example 3 of Preparation of antigen was dissolved in 1.5 ml of physiological saline solution, then to this solution was added 1.5 ml of a complete Freund's adjuvant to prepare a suspension. This suspension was administered subcutaneously to three rabbits (each of which having 2.5 to 3.0 kg of body weight) respectively, and the same amount of the suspension was administered to the same rabbits in every other weeks in 6 times. Further, the same amount of the suspension was: additionally administered to the same rabbits in every month in 3 times. 7 Days after the last administration of the suspension, the blood was taken out from the test animal. The blood was subjected to a centrifugal separation to obtain the serum which contains human interferon-$\alpha$ antibody (hereinafter, this product is referred to as [Antibody $\alpha$-N-IV]).

PREPARATIVE EXAMPLE 5

20 Micrograms of Antigen $\alpha$-N-IV which was obtained in Preparative Example 4 of Preparation of antigen was dissolved in 1.5 ml of physiological saline solution, then to this solution was added 1.5 ml of a complete Freund's adjuvant to prepare a suspension. This suspension was administered subcutaneously to seven rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the test animal. The blood was subjected to a centrifugal separation to obtain the serum which contains human interferon-α antibody (hereinafter, this product is referred to as [Antibody α-N-V]).

PREPARATIVE EXAMPLE 6

100 Micrograms of Antigen α-N-IV which was obtained in Preparative Example 4 of Preparation of antigen was dissolved in 1.5 ml of physiological saline solution, then to this solution was added 1.5 ml of a complete Freund's adjuvant to prepare a suspension. This suspension was administered subcutaneously to three rabbit (each of which having 2.5 to 3.0 kg of body weight) respectively, and the same amount of the suspension was administered to the same rabbit in every other weeks in 6 times. Further, the same amount of the suspension was additionally administered to the same rabbits in every month in 3 times. 7 Days after the last administration of the suspension, the blood was taken out from the test animal. The blood was subjected to centrifugal separation to obtain the serum which contains human interferon-α antibody (hereinafter, this product is referred to as [Antibody α-N-VI]).

PREPARATIVE EXAMPLE 7

Using 20 micrograms of Antigen α-N-V which was obtained in Preparative Example 5 of Preparation of antigen, and by a procedure similar to that described in the above-mentioned Preparative Example 5, there is obtained the serum which contains human interferon-α antibody (hereinafter, this product is referred to as [Antibody α-N-VII]).

PREPARATIVE EXAMPLE 8

Using 100 micrograms of Antigen α-B-V which was obtained in Preparative Example 5 of Preparation of antigen, and by a procedure similar to that described in the above-mentioned Preparative Example 4, there is obtained the serum which contains human interferon-α antibody (hereinafter, this product is referred to as [Antibody α-N-VIII]).

PREPARATIVE EXAMPLE 9

Using 20 micrograms of Antigen α-N-VI which was obtained in Preparative Example 6 of Preparation of antigen, and by a procedure similar to that described in the above-mentioned Preparative Example 3, there is obtained the serum which contains human interferon-α antibody (hereinafter, this product is referred to as [Antibody α-N-IX]).

PREPARATIVE EXAMPLE 10

Using 100 micrograms of Antigen α-N-VI which was obtained in Preparative Example 6 of Preparation of antigen, and by a procedure similar to that described in the above-mentioned Preparative Example 5, three rabbits were immunized and the blood was taken out from the rabbits, then the blood was subjected to a centfigural separation to obtain the serum which contains human interferon-α antibody (hereinafter, this product is referred to as [Antibody α-N-X]).

PREPARATIVE EXAMPLE 11

100 Micrograms of Antigen α-C-III which was obtained in Preparative Example 9 of Preparation of antigen was dissolved in 1.5 ml of physiological saline solution, then to this solution was added 1.5 ml of a complete Freund's adjuvant to prepare a suspension. This suspension was administered subcutaneously to seven rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the rabbits. The blood was subjected to a centrifugal separation to obtain the serum which contains human interferon-α antibody (hereinafter, this product is referred to as [Antibody α-C-III]).

PREPARATIVE EXAMPLES 12–14

Using Antigen α-C-I, Antigen α-C-II and Antigen α-C-IV each of which were obtained in Preparative Examples 7, 8 and 10 of Preparation of antigen respectively, and by a method similar to that described in the above-mentioned Preparative Example 11, of Preparation of antibody, there were obtained the serums, each of which contain the respective human interferon-α antibody (hereinafter, these products are referred to as [Antibody α-C-I], [Antibody α-C-II] and [Antibody α-C-IV] respectively.

PREPARATIVE EXAMPLE 15

30 Micrograms of Antigen α-C-II which was obtained in Preparative Example 9 of Preparation of antigen was dissolved in 1.5 ml of physiological saline solution, then to this solution was added 1.5 ml of a complete Freund's adjuvant to prepare a suspension. This suspension was administered subcutaneously to a rabbit (having 2.7 kg of body weight), and the same amount of the suspension was administered to the rabbit in every other weeks in 5 times. Further, the same amount of the suspension was additionally administered to the same rabbit in every three week intervals in 5 times. 7 Days after the last administration of the suspension, the blood was taken out from the rabbit, and the blood was subjected to a centrifugal separation to obtain the serum which contains human interferon-α antibody (hereinafter, this product is referred to as [Antibody α-C-V]).

PREPARATIVE EXAMPLE 16

Using 60 micrograms of Antigen α-C-III which was obtained in Preparative Example 9 of Preparation of antigen, and by a procedure similar to that described in the above-mentioned Preparative Example 15 of Preparation of antibody, there was obtained the serum which contains human interferon-α antibody (hereinafter, this product is referred to as [Antibody α-C-VI]).

PREPARATIVE EXAMPLE 17

Using 30 micrograms of Antigen α-C-V which was obtained in Preparative Example 11 of Preparation of antigen, and by a procedure similar to that described in the above-mentioned Preparative Example 15 of Preparation of antibody, by using two rabbits (having 2.5 to 3.0 kg of body weight) there was obtained the serum which contains human interferon-α antibody (hereinafter this product is referred to as [Antibody α-C-VIII]).

PREPARATIVE EXAMPLE 18

Using 60 micrograms of Antigen α-C-V which was obtained in Preparative Example 11 of Preparation of antigen, and by a method similar to that described in the above-mentioned Preparative Example 15 of Preparation of antibody, five rabbits (each of which having 2.5 to 3.0 kg of body weight) were immunized and the blood taken out from the rabbits were subjected to a centrifugal separation to obtain the serums each of which contain the respective human interferon-α antibody (hereinafter, these products are respectively referred to as [Antibody α-C-IX], [Antibody α-C-X], [Antibody α-C-XI], [Antibody α-C-XII] and [Antibody α-C-XIII]).

PREPARATIVE EXAMPLE 19

250 micrograms of Antigen β-I which was obtained in Preparative Example 12 of Preparation of antigen, was dissolved in 1.5 ml of physiological saline solution, to this solution was added 1.5 ml of a complete Freund's adjuvant to prepare a suspension. This suspension was administered to four rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the rabbits. The blood was subjected to a centrifugal separation to obtain the serum which contains human interferon-β antibody (hereinafter, this product is referred to as [Antibody β-I]).

PREPARATIVE EXAMPLE 20

25 Micrograms of Antigen β-II which was obtained in Preparative Example 13 of Preparation of antigen, was dissolved in 1.5 ml of physiological saline solution, then to this solution was added 1.5 ml of a complete Freund's adjuvant to prepare a suspension. This suspension was administered to four rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every months in 3 times. 7 Days after the last administration of the suspension, the blood was taken out from the rabbits. The blood was subjected to a centrifugal separation to obtain the serum which contains human interferon-β antibody (hereinafter, this product is referred to as [Antibody β-II]).

PREPARATIVE EXAMPLE 21

25 Micrograms of Antigen β-III which was obtained in Preparative Example 14 of Preparation of antigen, was dissolved in 1.5 ml of physiological saline solution, then to this solution was added 1.5 ml of a complete Freund's adjuvant to prepare a suspension. This suspension was administered subcutaneously to four rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in three times. 7 Days after the last administration of the suspension, the blood was taken out from the rabbits. The blood was subjected to a centrifugal separation to obtain the serum which contains human interferon-β antibody (hereinafter, this product is referred to as [Antibody β-III]).

PREPARATIVE EXAMPLE 22

25 Micrograms of Antigen β-IV which was obtained in Preparative Example 15 of Preparation of antigen, was dissolved in 1.5 ml of physiological saline solution, then to this solution was added 1.5 ml of a complete Freund's adjuvant to prepare a suspension. This suspension was administered subcutaneously to four rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the rabbits. The blood was subjected to a centrifugal separation to obtain the serum which contains human interferon-β antibody (hereinafter, this product is referred to as [Antibody β-IV]).

PREPARATIVE EXAMPLE 23

25 Micrograms of Antigen β-V which was obtained in Preparative Example 16 of Preparation of antigen, was do dissolved in 1.5 ml of physiological saline solution, then to this solution was added 1.5 ml of a complete Freund's adjuvant to prepare a suspension. This suspension was administered subcutaneously to four rabbits (each of which having 2.5 to 3.0 kg of body weight) respectively, and the same amount of the suspension was administered to the same rabbits in every other weeks in 6 times. Further, the same amount of the suspension was additionally administered to the same rabbits in every month in 3 times. 7 Days after the last administration of the suspension, the blood was taken out from the rabbits. The blood was subjected to a centriful separation to obtain the serum which a contains human interferon-β (hereinafter, this product is referred to as [Antibody β-V]).

PREPARATIVE EXAMPLE 24

Using Antigen β-VI which was obtained in Preparative Example 17 of Preparation of antigen, and by a method similar to that described in the above-mentioned Preparative Example 15 of Preparation of antibody, there is obtained the serum which contains antibody having high potency and having specificity to human interferon-β (hereinafter, this product is referred to as [Antibody β-VI]).

Assay of the titer of antibodies-(1)

The titer of Antibody α-N-I through Antibody α-N-X were assayed as follows:

Each of Antibodies was diluted with physiological saline solution to prepare a series of diluted samples thereof, having 10, $10^2$, $10^3$, $10^4$, $10^5$, ... -fold diluted concentration (initial concentration). To 100 microliters each of these diluted samples was added 0.1 ml of a diluted solution of $^{125}I$ labelled-Peptide D [which was obtained in Preparative Example of labelled peptide-1, as mentioned previously, and was diluted to prepare a diluted solution having about 9,500 cpm of the radioactivity] and 0.2 ml of 0.05M-phosphate buffer solution (pH=7.4) [containing 0.25% of BSA, and 10 mM- EDTA and 0.02% of NaN₃], then this mixture was incubated at 4° C. for 24 hours. The resulting product of the antibody combined with the $^{125}$I labelled-Peptide D formed in the incubated mixture was isolated from the unreacted (not combined) $^{125}$I labelled-Peptide D by a dextran-activated carbon method and a centrifugal separation method (at 4° C. for 30 minutes, 3,000 rpm).

The combined ratio (%) of the antibody to the $^{125}$I labelled Peptide D in the resulting product was determined by counting the radioactivity of each samples in the series of diluted concentration. The data of combined ratio (%) obtained from the respective samples in the series of diluted concentration were plotted on a chart, in which the ordinate shows the combined ratio (%) of the antibody to the $^{125}$I labelled-Peptide D, while the abscissa shows the diluted concentration of the antibody. From the plotted chart, a diluted concentration of the antibody showing 50% of the combined ratio, which is the titer of the antibody, was obtained. Results are shown in Table 1.

TABLE 1

| Antibody | Titer | Antibody | Titer |
|---|---|---|---|
| α-N-I | 10,000 | α-N-V | 150,000 |
| α-N-II | 12,000 | α-N-VII | 180,000 |
| α-N-III | 120,000 | α-N-VIII | 42,000 |
| α-N-IV | 200,000 | α-N-X | 28,000 |

Test of the specificity of Antibody α-N-IV to human lymphoblastoid interferon

In conducting said test of specificity, the following materials were used as the samples to be tested:

(1) Human interferon-β (prepared by Tokyo Metropolitan Institute of Medical Science, specific activity: $3 \times 10^6$ U/mg of protein), in various concentrations (2) Peptide C which as obtained in Preparative Example A-3 of Synthesis of peptide, i.e., a peptide chain of human lymphoblastoid interferon (3) Human interferon-α (prepared by Hayashibara Biochemical Research Laboratory, lymphoblastoid interferon Lot. No. 800928)

(4) Human interferon-α (obtained from Dr. Cantell, Central Public Health Laboratory, Finland)

On the other hand, as the standard diluting agent, 0.05M-phosphate buffer solution (pH=7.4) containing 0.25% of BSA, 5 mM-EDTA and 0.02% of Na N₃ was used.

To each of test tubes, there is placed 0.2 ml of the standard diluting agent, 0.1 ml of the sample to be tested, 0.1 m.1 of Antibody α-N-IV obtained in Preparative Example-4 of Preparation of antibody (titer=200,000) and 0.1 ml of $^{125}$I labelled-Peptide D [which was obtained in Preparative Example of labelled peptide-1, as mentioned previously, and was diluted to prepare a diluted solution having about 2,800 cpm of the radioactivity]. Each of the test tubes containing the above-mentioned mixture was incubated at 4° C. for 72 hours, then 0.1 ml of normal porcine serum was added to the mixture, next 0.5 ml of a suspension of activated carbon being coated with dextran was added thereto, and the whole mixture was allowed to stand at 4° C. for 30 minutes, then the whole mixture was subjected to a centrifugal separation at 4° C. for 30 minutes under the condition of 3,000 rpm for isolating the resulting product of the antibody combined with the $^{125}$I labelled-peptide from the unreacted (not combined) $^{125}$I labelled-peptide. The radioactivity of each peptides was measured. The binding ratio (%) of $^{125}$I labelled-peptide and each samples at each concentrations and dilutions was determined taking binding ratio ($B_o$) corresponding to titer of used antibody as 100%. The results are shown in FIG. 1, wherein the ordinate shows the relative bound percentage [(%)=$B/B_o \times 100$], while the abscissa shows the concentration of the samples to be tested (Peptide C which was obtained in Preparative Example A-3 of Synthesis of peptide, i.e., a peptide chain of human lymphoblastoid interferon, human interferon-β and human interferon-α). In this FIG. 1, curve (a) is Peptide C, i.e., a peptide chain of human lymphoblastoid interferon, curve (b) is human interferon-α (obtained from Dr. Cantell, Central Public Health Laboratory, Finland), curve (c) is human interferon-α (prepared by Hayashibara Biochemical Research Laboratory) and curve (d) is human interferon-β. As can be seen from the curves shown in FIG. 1 that the reactivity of Antibody α-N-IV to human interferon-β is clearly different from the reactivity of Antibody α-N-IV to human interferon-β, which means that Antibody α-N-IV is an antibody having high specificity and it does not cross match to human interferon-β until the concentration of $3.0 \times 10^6$ U/ml.

Assay of the titer of antibodies-(2)

The titer of Antibody α-C-I through Antibody α-C-XIII were assayed as follows:

Each of Antibodies was diluted with physiological saline solution to prepare a series of diluted samples thereof, having 10, $10^2$, $10^3$, $10^4$, $10^5$, . . . -fold diluted concentration (initial concentration). To 100 microliters each of these diluted samples was added 0.1 ml of a diluted solution of $^{125}$I labelled-Peptide H [which was obtained in Preparative example of labelled peptide-2-1, as mentioned previously, and was diluted to prepare a diluted solution having about 9,500 cpm of the radioactivity] and 0.2 ml of 0.05M-phosphate buffer solution (pH=7.4) [containing 0.25% of BSA, and 10 nM-EDTA and 0.02% of NaN₃2, then this mixture was incubated at 4° C. for 24 hours. The resulting product of the antibody combined with the $^{125}$I labelled-Peptide H formed in the incluated mixture was isolated from the unreacted (not combined) $^{125}$I labelled-Peptide H by a dextran-activated carbon method and a centrifugal separation method (at 4° C. for 30 minutes, 3,000 rpm).

The combined ratio (%) of the antibody to the $^{125}$I labelled-Peptide H in the resulting product was determined by counting the radioactivity of each samples in the series of diluted concentration. The data of the combined ratio (%) obtained from the respective samples in the series of diluted concentration were plotted on a chart, in which the ordinate shows the combined ratio (%) of the antibody to the $^{125}$I labelled-Peptide H, while the abscissa shows the diluted concentration of the antibody (initial concentration). From the plotted chart, a diluted concentration of the antibody showing 50% of the combined ratio which is the titer of the antibody was obtained. Results are shown in Table 2.

TABLE 2

| Antibody | Titer | Antibody | Titer |
|---|---|---|---|
| α-C-I | 2,500 | α-C-VIII | 1,200 |
| α-C-II | 4,200 | α-C-IX | 6,000 |
| α-C-III | 50,000 | α-C-X | 1,100 |
| α-C-IV | 1,200 | α-C-XI | 2,200 |
| α-C-V | 10,400 | α-C-XII | 3,600 |
| α-C-VI | 2,600 | α-C-XIII | 1,000 |

TABLE 2-continued

| Antibody | Titer | Antibody | Titer |
|---|---|---|---|
| α-C-VII | 40,000 | | |

As can be seen from the results shown in Table 2, the C-terminal peptide of human interferon-as represented by the general formula (2) and derivatives thereof have strong antigenicity as compared with that of other peptides, for example as can be seen from the titer of Antibody α-C-IX through Antibody α-C-XIII that the useful antibodies can be produced in the most of the animals being administered the antigen.

Test of the specificy of Antibody α-C-III to human interferon-α

(a) In conducting said test os specificity, the following materials were used as the samples to be tested:

(1) Human interferon-β (prepared by Tokyo Metropolitan Institute of Medical Science, specific activity: $3 \times 10^6$ U/mg of protein), in various concentrations (2) Peptide G which was obtained in Preparative Example B-16 (b) of Synthesis of peptide, i.e., a peptide chain of human interferon-α

(3) Human interferon-α (lymphoblastoid interferon, prepared by Hayashibara Biochemical Research Laboratory)

On the other hand, as to the standard diluting agent, 0.05M-phosphate buffer solution (pH=7.4) containing 0.25% of BSA, 5 mM-EDTA and 0.02% of NaN₃ was used.

To each of test tubes, there is placed 0.2 ml of the standard diluting agent, 0.1 ml of the sample to be tested, 0.1 ml of Antibody α-C-III obtained in Preparative Example-11 of Preparation of antibody and 0.1 ml of $^{125}$I labelled-Peptide H [which was obtained in Preparative Example of labelled peptide-2-1, as mentioned previously, and was diluted to prepare a diluted solution having about 2,800 cpm of the radioactivity]. Each of the test tubes containing the above-mentioned mixture was incubated at 4° C. for 72 hours, then 0.1 ml of normal porcine serum was added to the incubated mixture, next 0.5 ml of a suspension of activated carbon being coated with dextran was added thereto, and the whole mixture was allowed to stand at 4° C. for 30 minutes. Then the whole mixture was subjected to a centrifugal separation at 4° C. for 30 minutes under the condition of 3,000 rpm for isolating the resulting product of the antibody combined with the $^{125}$I labelled-peptide from the unreacted (being not combined) $^{125}$I labelled-peptide. The radioactivity of each peptides was measured. The binding ratio (%) of $^{125}$I labelled-peptide and each samples at each concentration and dilutions was determined taking binding ratio (B₀) corresponding to titer of used antibody as 100%. As can be seen form the results obtained from this test, that the reactivity of Antibody α-C-III to human interferon-α is clearly different from the reactivity of Antibody α-C-III to human interferon-β, which means that Antibody α-C-III is an antibody having high specificity, with low cross matching property to human interferon-β.

Additionally, similar tests were conducted on the specificities of Antibody α-C-I, Antibody α-C-II, Antibody α-C-IV to Antibody α-C-VII and Antibody α-C-IX to Antibody α-C-XIII and are confirmed that these antibodies have high specificities to human interferon-α.

Figure 2:
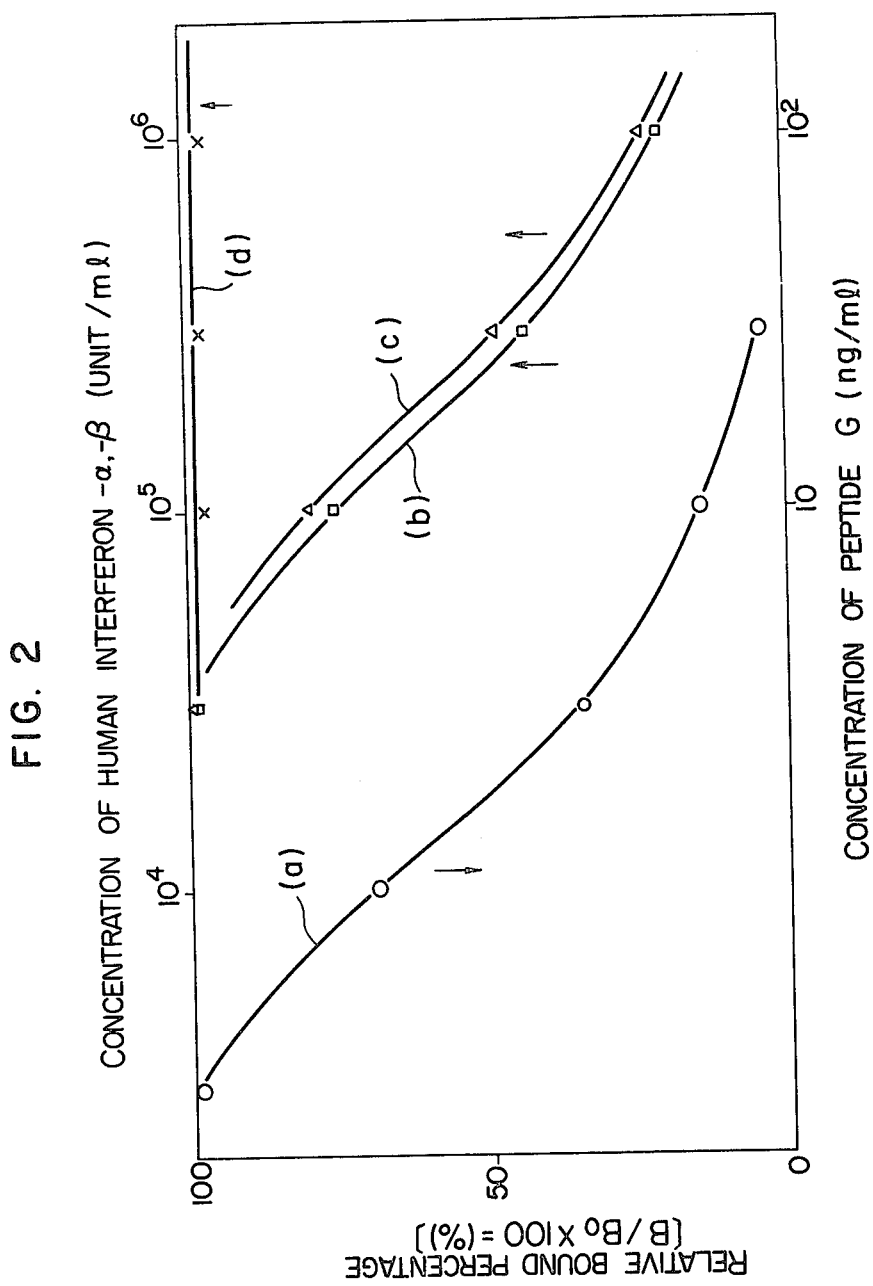

(b) Similar tests were conducted on Antibody α-C-VIII as in the test (a) mentioned above. The results are shown in FIG. 2, in which the ordinate shows the relative bound percentage [(%)=B/B₀×100], while the abscissa shows the concentrations of the samples to be tested (Peptide G which was obtained in Preparative Example B-16 (b) of Synthesis of peptide, i.e., a peptide chain of human interferon-α, human interferon-α [lymphoblastoid interferon, prepared by Hayashibara Biochemical Research Laboratory, and leucocytes interferon obtained from National Institute of Health] and human interferon-β (specific activity: $3 \times 10^6$ U/mg of protein, prepared by Tokyo Metropolitan Institute of Medical Science). In this FIG. 2, curve (a) is Peptide G, curve (b) is human interferon-α (prepared by Hayashibara Biochemical Research Laboratory), curve (c) is human interferon-α (obtained from National Institute of Health), and curve (d) is human interferon-β prepared by Tokyo Metropolitan Institute of Medical Science). As can be seen from the curves shown in FIG. 2 that the reactivity of Antibody α-C-VIII to human interferon-β is clearly different from the reactivity of Antibody α-C-VIII is an antibody having high specificity and it does not cross match to human interferon-β until the concentration of $1.0 \times 10^6$ U/ml.

Assay of the titer of antibody-(3)

The titer of Antibody β-I through Antibody β-VI were assayed as follows:

Each of Antibodies was diluted with physiological saline solution to prepare a series of diluted samples thereof, having 10, $10^2$, $10^3$, $10^4$, $10^5$ . . . -fold diluted concentration (initial concentration). To 100 microliters each of these diluted samples was added 0.1 ml of a diluted solution of $^{125}$I labelled-Peptide M [which was obtained in Preparative Example of labelled peptide-3, as mentioned previously, and was diluted to prepare a diluted solution having about 10,000 cpm of the radioactivity] and 0.2 ml of 0.1M-phosphate buffer solution (pH=7.4) [containing 0.1% of BSA, 0.15M-sodium chloride and 0.01% of NaN₃], then this mixture was incubated at 4° C. for 24 hours. The resulting product of the antibody combined with the $^{125}$I labelled-Peptide M formed in the incubated mixture was isolated from the unreacted (being not combined) $^{125}$I labelled-Peptide M by dextran-activated carbon method and a centrifugal separation method (at 4° C. for 15 minutes, 3,000 rpm).

The combined ratio (%) of the antibody to the $^{125}$I labelled Peptide M in the resulting product was determined by counting the radioactivity of each samples in the series of from the respective samples in the series of diluted concentration (initial concentration) were plotted on a chart, in which the ordinate shows the combined ratio (%) of the antibody to the $^{125}$I labelled-Peptide M, while the abscissa shows the diluted concentration of the antibody. From the plotted chart, a diluted concentration of the antibody showing 50% of the combined ratio which is the titer of the antibody was obtained. The results are shown in Table 3.

TABLE 3

| Antibody | Titer |
|---|---|
| α-V | 52,000 |
| α-VI | 100,000 |

Test of the specificity of Antibody β-V to human interferon-β

In conducting said specificity, the following materials were used as the samples to be tested:

(1) Human interferon-β (specific activity: $3 \times 10^6$ U/mg of protein, prepared by Tokyo Metropolitan Instituted of Medical Science)

(2) The 1st to 13th peptide chain of human interferon-β (Peptide M which was obtained in Example 5 of Preparative Example C of Synthesis of peptide)

(3) Human interferon-α (Lymphoblastoid interferon, Lot No. 800928, prepared by Hayashibara Biochemical Research Laboratory)

On the other hand, as to the standard diluting agent, 0.1M-sodium phosphate buffer solution (pH=7.4) containing 0.1% of BSA, 0.15M-NaCl and 0.01% of NaN₃ was used.

Figure 3:
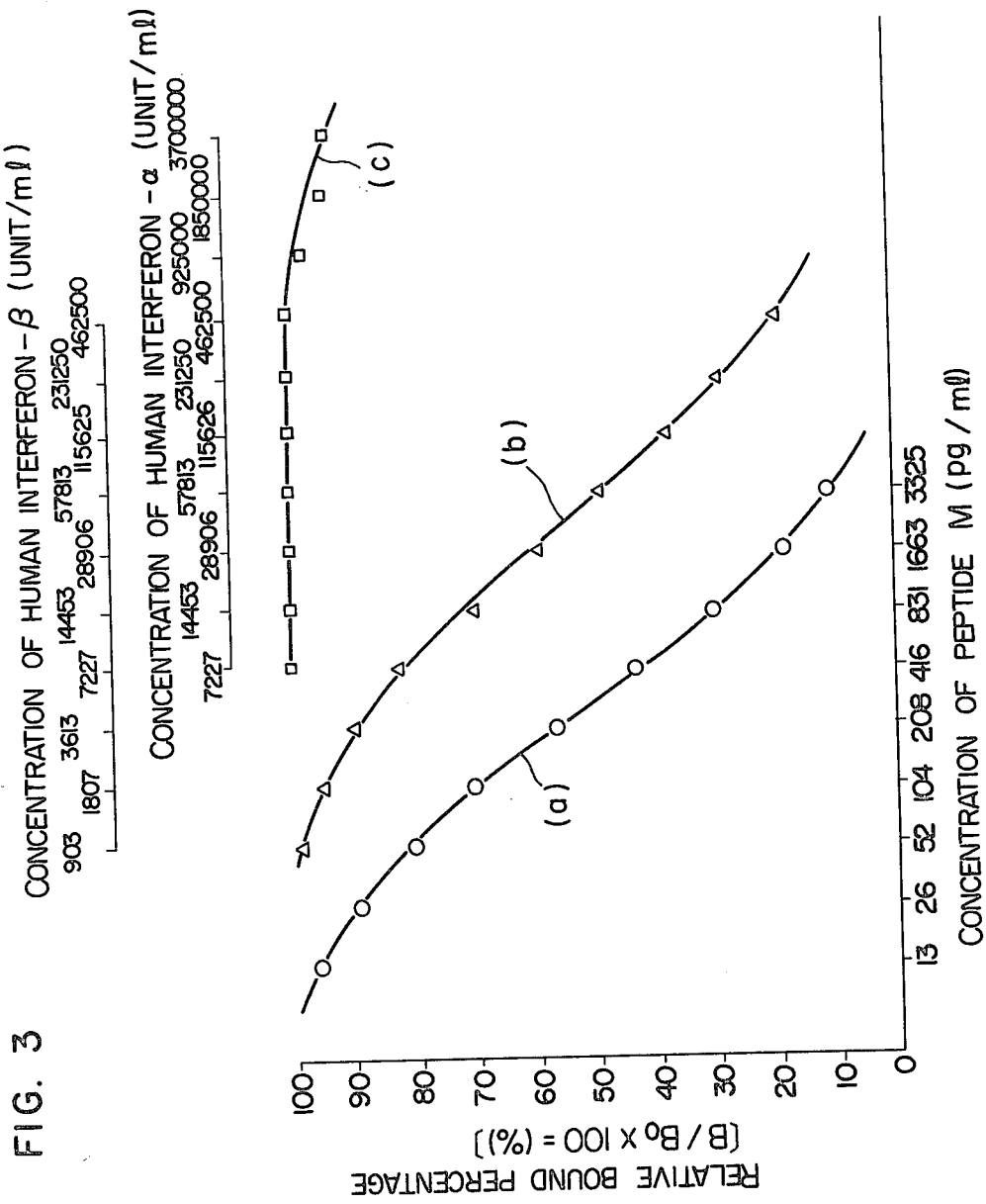
FIGS. 3 and 4 show curves indicating the specificity of the human interferon-β antibody obtained according to the present invention.

To each of test tubes, there is placed 0.2 ml of the standard diluting agent, 0.1 ml of the sample to be tested, 0.1 ml of antibody β-V obtained in Preparative Example 23 of Preparation of antibody (titer=52,000) and 0.1 ml of $^{125}$I labelled-Peptide M [which was obtained in Preparative example of labelled peptide-3, the mentioned above, was diluted to prepare a diluted solution having about 10,000 cpm of the radioactivity], then this mixture was incubated at 4° C. for 48 hours. To the incubated mixture was added 0.1 ml of normal sheep serum, next to this mixture was added 0.5 ml of a suspension of activated carbon coated with dextran, and the whole mixture was allowed to stand at 4° C. for 30 minutes, and was subjected to a centrifugal separation at 4° C. for 30 minutes under the condition of 3,000 rpm for isolating the resulting product of the antibody combined with the $^{125}$I labelled-peptide from the unreacted (being not combined) $^{125}$I labelled-peptide. The radioactivity of each peptides was measured. The binding ratio (%) of $^{125}$I labelled-peptide and each samples at each concentrations and dilutions was determined taking binding ratio ($B_o$) corresponding to titer of used antibody as 100%. The results are shown in FIG. 3, in which the ordinate shows the relative bound percentage [(%)=B/$B_o$×100], while the abscissa shows the concentration of the samples to be tested [the 1st to 13th peptide chain of human interferon-β (Peptide M), human interferon-β and human interferon-α]. In this FIG. 3, curve (a) is the 1st to 13th peptide chain of human interferon-β (Peptide M), curve (b) is human interferon-β, and curve (c) is human interf interferon-α. As can be seen from the curves shown in FIG. 3 that the reactivity of Antibody β-V to human interferon-α is clearly different from the reactivity of Antibody β-V to human interferon-β, from these facts that Antibody β-V is an antibody having high specificity and it does not cross match to human interferon-α until the concentration of $3.7 \times 10^6$ U/ml.

Figure 4:
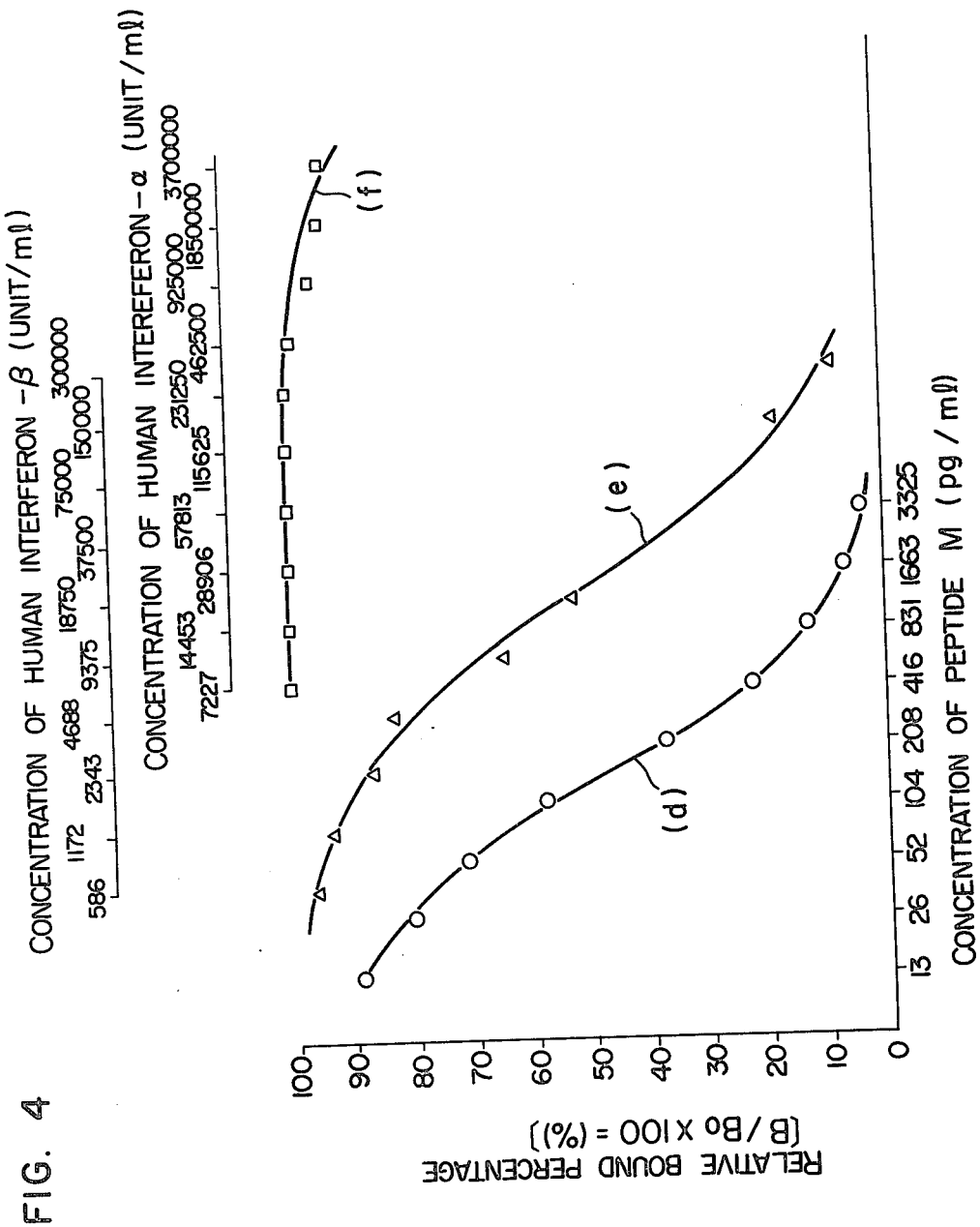

Additionally, similar tests were conducted on the specificities of Antibody β-VI to human interferon-β. The results are shown in FIG. 4, in which the ordinate shows the relative bound percentage [(%)=B/$B_o$×100], while the abscissa shows the concentrations of the samples tested [the 1st to 13th peptide chain of human interferon-β (Peptide M), human interferon-β and human interferon-α]. In this FIG. 4, curve (d) is the 1st to 13th peptide chain of human interferon-β (Peptide M), curve (e) is human interferon-β and curve (f) is human interferon-α.

Similar tests were conducted on the specifities of Antibody β-II, Antibody β-III and Antibody β-IV. Thus, each of test tubes, there is placed 0.2 ml of the above-mentioned standard diluting agent, 0.1 ml of the above-mentioned the sample to be tested, 0.1 ml of Antibody β-II, Antibody β-III or Antibody β-IV and 0.1 ml of $^{125}$I labelled-Peptide M, then the reaction was carried out under the condition similar to that mentioned previously. When the bonding reactivity between Antibody β-V or Antibody β-VI obtained from the 1st to 13th peptide chain of human interferon-β (Peptide M) and the 1st to 13th peptide of human interferon-β (Peptide) are taken as 100%, the relative bound percentage (%) of the respective Antibodies are shown in Table 4.

TABLE 4

| Antibody | Relative bound percentage | Antibody | Relative bound percentage |
|---|---|---|---|
| β-V | 100 | β-VI | 100 |
| β-II | 25 | β-II | 25 |
| β-III | 30 | β-III | 27 |
| β-IV | 50 | β-IV | 70 |

Determination of the sensitivity limit

Figure 5:
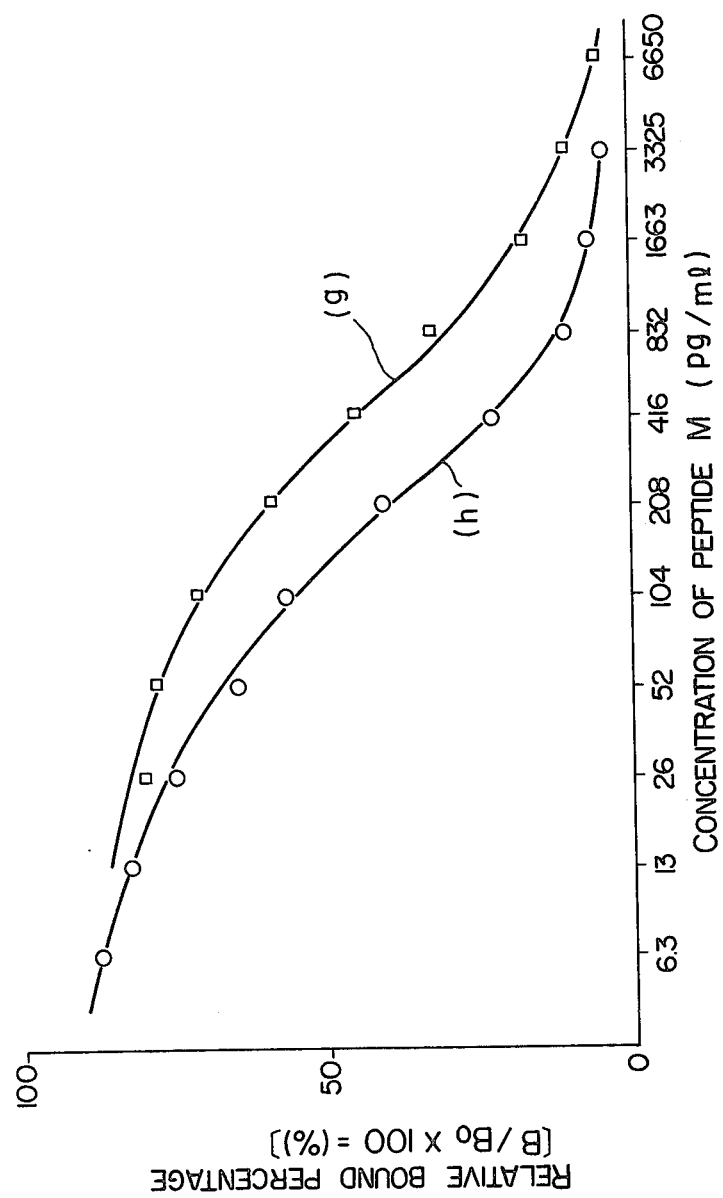
FIG. 5 shows curves indicating the relationship between the concentration of the 1st to 13th peptide chain of human interferon-β and the relative bound percentage (%) with respect to the human interferon-β antibody obtained according to the present invention.

To each of test tubes, there is placed 0.2 ml of the standard diluting agent, 0.1 ml of the 1st to 13th peptide chain of human interferon-β (Peptide M), 0.1 ml of Antibody β-V obtained in Example 23 of Preparation of antibody or Antibody β-VI obtained in Example 24 of Preparation of antibody, and 0.1 ml of $^{125}$I labelled-Peptide M [which was obtained in Preparative example of labelled peptide-3, as mentioned previously, and was diluted to prepare a diluted solution having about 10,000 cpm of the radioactivity], then this mixture was incubated at 4° C. for 48 hours. To the incubated mixture was added 0.1 ml of normal sheep serum, next to this mixture was added 0.5 ml of a suspension of activated carbon being coated with dextran, and the resulting mixture was allowed to stand 4° C. for 30 minutes, and was subjected to a centrifugal separation at 4° C. for 30 minutes under the condition of 3,000 rpm for isolating the resulting product of the antibody combined with the $^{125}$I labelled-peptide from the unreacted (being not combined) $^{125}$I labelled-peptide. The radioactivity of each peptides was measured. The binding ratio (%) of $^{125}$I labelled-peptides and each samples at each concentrations and dilutions was determined taking binding ratio ($B_o$) corresponding to titer of used antibody as 100%. The results are shown in FIG. 5, in which the ordinate shows the relative bound percentage [(%)=B/$B_o$×100], while the abscissa shows the concentration of the 1st to 13th peptide chain of human interferon-β (Peptide M), curve (g) is a data obtained by using Antibody β-V, and curve (h) is a data obtained by using Antibody β-VI. As can be seen from these curves in FIG. 5, that the minimum sensitivity limit in assaying human interferon is 13 picograms/ml when using Antibody β-V, and is 5 picograms/ml when using Antibody β-VI.

Assay of human interferon-α by fluorescence polarization immunoassay-1

(a) Preparation of fluorochrome labelled-peptide solution

FITC labelled-Peptide C [obtained in Preparative Example of labelled peptide-4 (1)] was dissolved in 0.1M-sodium phosphate buffer solution (pH=7) [containing 0.9 W/V% NaCl and 0.05 W/V% BSA] to prepare a solution having the concentration of $3\times10^{-9}$M-FITC labelled-Peptide C, (hereinafter, this solution is referred to as [Solution-A]).

(b) Preparation of fluorochrome labelled-peptide blank solution for blank test

A solution having the same composition as in the Solution-A except that without containing FITC labelled-Peptide C was prepared, (hereinafter, this solution is referred to as [Solution-B]).

(c) Preparation of antibody solution

Antibody α-N-VII [obtained in Preparative Example-7 of Preparation of antibody] (titer=180,000) was diluted 150-fold with physiological saline solution, (hereinafter, this solution is referred to as [Solution-C]).

(d) Preparation of diluting solution

A diluting solution (pH=7.8) containing 9.89 g/l of $H_3BO_3$, 4.32 g/l of $Na_2B_4O_7.10H_2O$, 9 g/l of NaCl, 0.005 W/V% of $NaN_3$ and 0.01 W/V% of BSA was prepared, (hereinafter, this solution is referred to as [Solution-D]).

(e) Preparation of a series of diluted solutions (1) Peptide C [obtained in Preparative Example A-3-5 of Preparation of peptide] was dissolved in 0.1M-sodium phosphate buffer solution (pH=6.5) containing 0.9 W/V% of NaCl, 0.05 W/V% of BSA to prepare a solution having the concentration of 5 micrograms/liter of Peptide C. Then said solution was diluted with Solution-D to prepare a series of diluted solutions having concentrations of 500, 250, 125, 62.5, 31.25, 15.6, 7.8, 3.9, 1.95, 0.925, 0.463 and 0 ng/ml of Peptide C.

(2) By using human interferon-α (Cantell) and method similar to that described in (1) as above, a series of diluted solutions of human interferon-α were prepared. The concentrations of a series of diluted solutions are $1\times10^6$, $0.5\times10^6$, $0.125\times10^6$, $0.063\times10^6$, $0.031\times10^6$, $0.016\times10^6$, $0.008\times10^6$ and 0 U/ml of human interferon-α.

(f) Determination of polarization degree (P value)

To 0.2 ml of each of the diluted solution prepared in (e)-(1) was added 0.05 ml of Solution-A, 0.1 ml of Solution-C and 0.65 ml of Solution-D to prepare a sample solution of Peptide C. Similarly, a reference sample solution of Peptide C was prepared by using 0.05 ml of Solution-B in place of Solution-A.

Similar to the above, a series of diluted sample solutions of human interferon-α and a series of diluted reference sample solutions thereof were prepared from the series of diluted solutions as described in (e)-(2).

Further, a sample solution of antibody for blank test was prepared by mixing 0.05 ml of Solution-A with 0.95 ml of Solution-D, and a reference sample solution of antibody for blank test was prepared by mixing 0.05 ml of Solution-B with 0.95 ml of Solution-D.

Each of these sample solutions and reference sample solutions were incubated at 4° C. for 12 hours, then the polarized light in the fluorescence was determined by an apparatus for measuring fluorescence polarization intensity. The polarization degree (P value) of each of the series of diluted sample solutions was calculated by the following formula.

$$P = \frac{(I_{VS} - I_{VR}) - (I_{HS} - I_{HR})}{(I_{VS} - I_{VR}) + (I_{HS} - I_{HR})} \times 100\ (\%)$$

Figure 6:
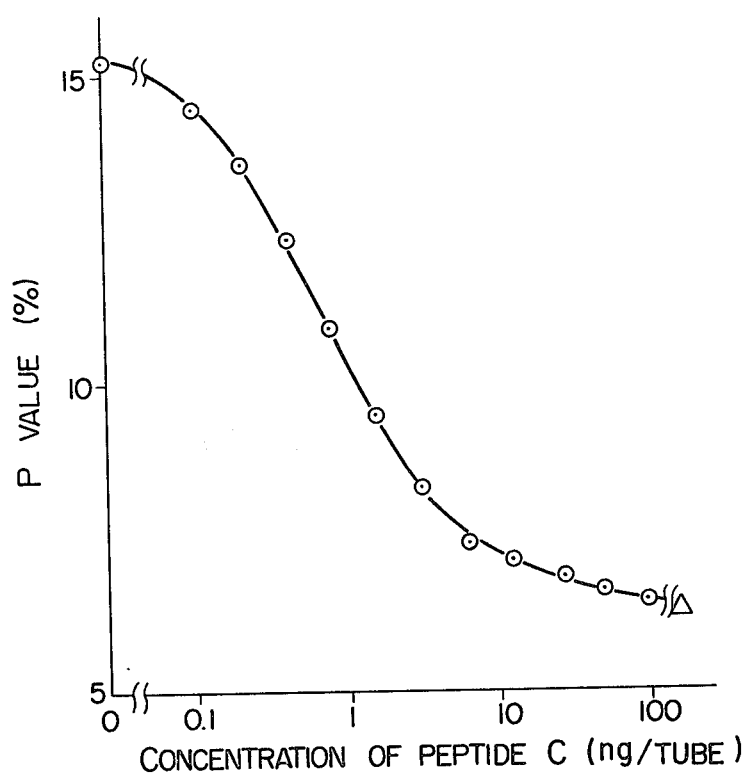
FIGS. 6 to 10 show the calibration curves in fluorescence polarization immunoassay system according to the present invention.
Figure 7:
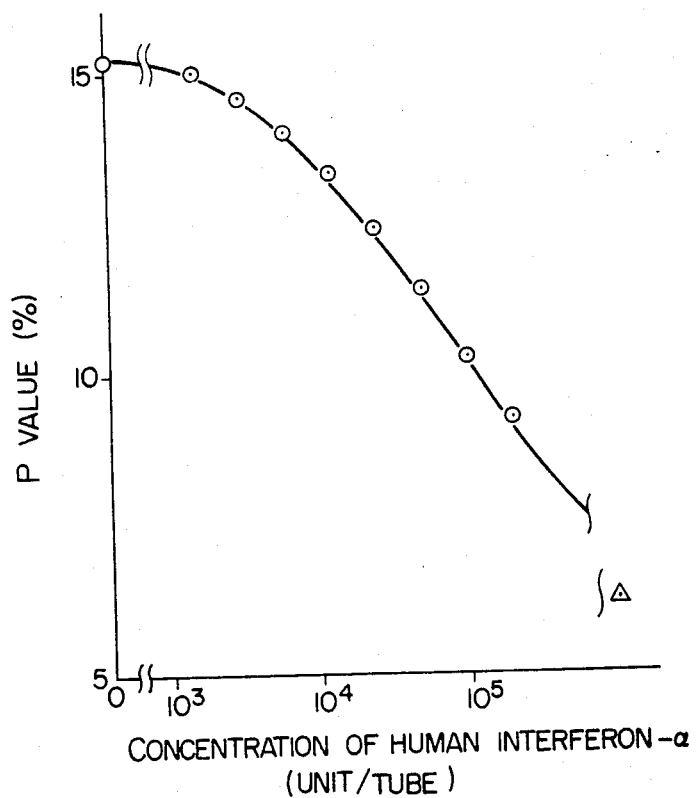

[wherein
$I_{VS}$: the strength of vertical polarized fluorescence of the sample
$I_{HS}$: the strength of horizontal polarized fluoroscence of the sample
$I_{VR}$: the strength of vertical polarized fluorescence of the reference sample
$I_{HR}$: the strength of horizontal polarized fluorescence of the reference sample] The results are shown in FIGS. 6 and 7. From these FIGS. 6 and 7 the concentration corresponding to a half of the change of P value is 0.79 ng/Tube in Peptide C, and is $7.2\times10^4$ U/Tube in human interferon-α, and the ratio of these value, that is 91 U/pg was obtained as the cross matching ratio.

Similarly, the P value was determined in a sample solution of human interferon-α of unknown concentration, and the potency was assayed from FIG. 6 or FIG. 7.

Assay of human interferon-α fluorescence polarization immonoassay-2

(a) Preparation of fluorochrome labelled-peptide solution

DTAF labelled-Peptide G [obtained in Preparative Example of labelled peptide-5 (2)] was dissolved in 0.1M-sodium phosphate buffer solution (pH=7) [containing 0.9 W/V% of NaCl and 0.05 W/V% of BSA] to prepare a solution having the concentration of $1.5\times10^{-9}$M-DTAF labelled-Peptide G, (hereinafter, this solution is referred to as [Solution-A']).

(b) Preparation of fluorochrome labelled-peptide blank solution blank test

A solution having the same composition as in the Solution-A' except that without containing DTAF labelled-Peptide G was prepared, (hereinafter, this solution is referred to as [Solution-B']).

(c) Preparation of antibody solution

Antibody α-C-VIII (titer=1,200) [obtained in Preparative Example-17 of Preparation of antibody] was diluted 40-fold with physiological saline solution, (hereinafter, this solution is referred to as [Solution-C']).

(d) Preparation of diluting solution

A diluting solution (pH=7.0) containing 9.89 g/l of $H_3BO_3$, 4.32 g/l of $Na_2B_4O_7.10H_2O$, 9 g/l of NaCl, 0.005 W/V% of $NaN_3$ and 0.01 W/V% of BSA was prepared, (hereinafter, this solution is referred to as [Solution-D']).

(e) Preparation of a series of diluted solutions (1) Peptide G [obtained in Preparative Example B-16 (b) of Preparation of peptide] was dissolved in 0.1M-sodium phosphate buffer solution (pH=6.5) containing 0.9 W/V% of NaCl and 0.05 W/V% of BSA, to prepare a solution having the concentration of 5 micrograms/liter of Peptide G. Then said solution was diluted with Solution-D' to prepare a series of diluted solutions having concentrations of 200, 66.7, 22.2, 7.4, 2.5, 0.8 and 0 nM of Peptide G.

(2) By using human interferon-α (Cantell) and method similar to that described in (1) as above, a series of diluted solutions of human interferon-α were prepared. The concentrations of a series of diluted solutions are $6.4 \times 10^6$, $3.2 \times 10^6$, $1.6 \times 10^6$, $0.8 \times 10^6$, $0.4 \times 10^6$, $0.2 \times 10^6$, $0.1 \times 10^6$, $0.05 \times 10^6$ and 0 U/ml of human interferon-α.

(f) Determination of polarization degree (P value)

To 0.1 ml of each of the diluted solution prepared in (e)-(1) was added 0.2 ml of Solution-A', and 0.2 ml of Solution-C' to prepare a sample solution of Peptide G. Similarly, a reference sample solution of Peptide G was prepared by using 0.1 ml of Solution-B' in place of Solution-A'.

Similar to the above, a series of diluted sample solutions of human interferon-α and a series of diluted reference sample solution thereof were prepared from the series of diluted solutoins as described in (e)-(2).

Further, a sample solution of antibody for blank test was prepared by mixing 0.2 ml of Solution-A' with 0.3 ml of Solution-D', and a reference sample solution of antibody for blank test was prepared by mixing 0.2 ml of Solution-B' with 0.3 ml of Solution-D'.

Each of these sample solutions and reference sample solutions were incubated at 4° C. for 12 hours, then the polarized light in the fluorescence was determined by an apparatus for measuring fluorescence polarization intensity. The polarization degree (P value) of each of the series of diluted sample solutions was calculated by the following formula.

$$P = \frac{(I_{VS} - I_{VR}) - (I_{HS} - I_{HR})}{(I_{VS} - I_{VR}) + (I_{HS} - I_{HR})} \times 100 \, (\%)$$

[wherein $I_{VS}$: the strength of vertical polarized fluorescence of the sample $I_{HS}$: the strength of horizontal polarized fluorescence of the sample $I_{VR}$: the strength of vertical polarized fluorescence of the reference sample $I_{HR}$: the strength of horizontal polarized fluorescence of the reference sample]

Figure 8:
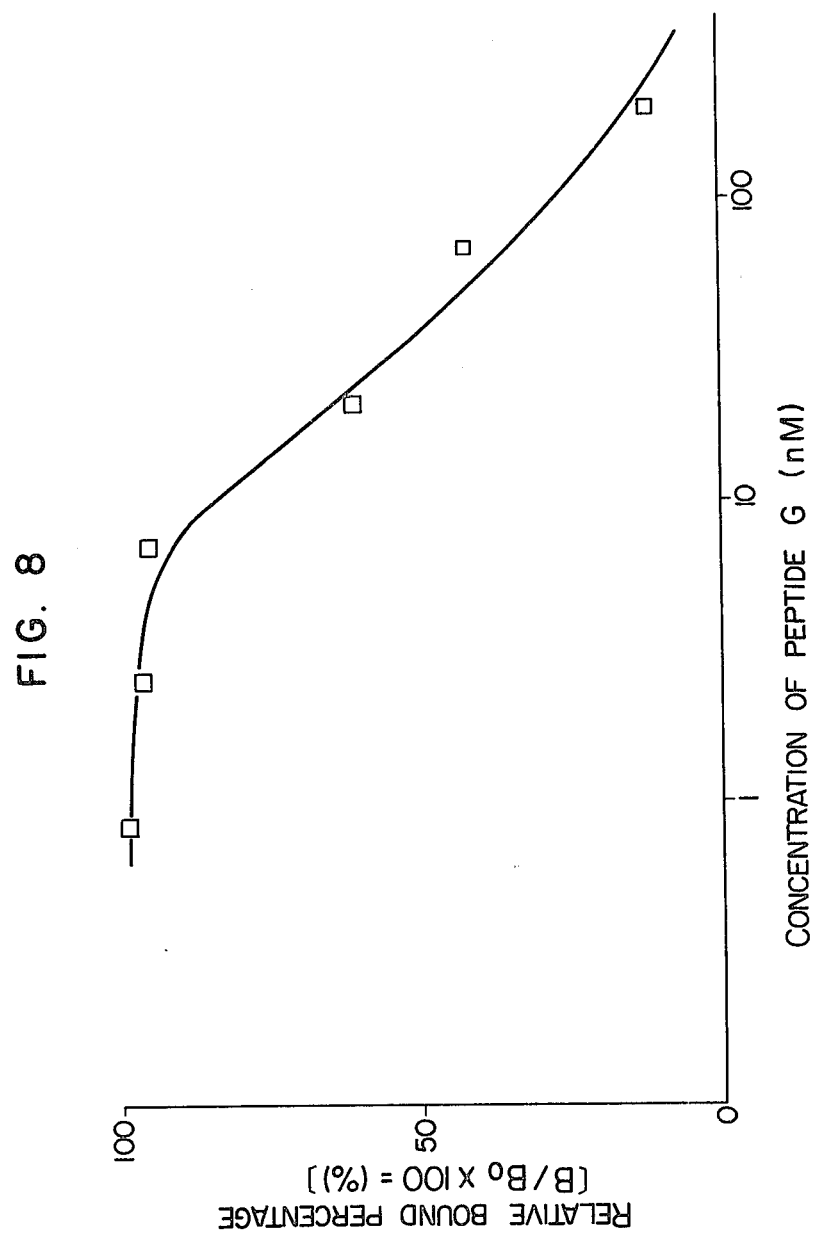

The results are shown in FIG. 8, wherein the relative bound percentage [$B/B_o$ (%)] is calculated from the following formula.

$$B/B_o = \frac{P - P_f}{P_o - P_f} \times 100 \, (\%)$$

[wherein

P: polarization degree of the sample $P_o$: polarization degree of the sample having zero concentration $P_f$: polarization degree obtained from the sample solution of the antibody for blank test]

From FIG. 8, the concentration corresponding to 50% value of $B/B_o$ is 36 mM in Peptide G. And similar to the above-mentioned procedure, the concentration corresponding to 50% value of $B/B_o$ was obtained as $1.0 \times 10^7$ U/Tube. Then the ratio of these values that is $2.78 \times 10^5$ U/ml/nM was obtained as the cross matching ratio.

Similarly, the P value and $B/B_o$ value were determined in sample solution of human interferon-α of unknown concentration, and the potency was assayed from FIG. 8.

Assay of human interferon-β by fluorescence polarization immunoassay-3

(a) Preparation of fluorochrome labelled-peptide solution

FITC labelled-Peptide M [obtained in Preparative Example of labelled peptide-6 (1)] was dissolved in 0.1M-sodium phosphate buffer solution (pH=7) [containing 0.9 W/V% of NaCl and 0.05 W/V% of BSA] to prepare a solution having the concentration of $3 \times 10^{-9}$M-FITC labelled-Peptide M, (hereinafter, this solution is referred to as [Solution-A"]).

(b) Preparation of fluorochrome labelled peptide blank solution for blank test

A solution having the same composition as in the Solution-A" except that without containing FITC-labelled-Peptide M was prepared, (hereinafter, this solution is referred to as [Solution-B"]).

(c) Preparation of antibody solution

Antibody β-V (potency-52,000) [obtained in Preparative Example-23 of Preparation of antibody] was diluted 800-fold with physiological saline solution, (hereinafter, this solution is referred to as [Solution-C"]).

(d) Preparation of diluting solution

A diluting solution (pH=7.8) containing 9.89 g/l of $H_3BO_3$, 4.32 g/l of $Na_2B_4O_7.10H_2O$, 9 g/l of NaCl, 0.005 W/V% of $NaN_3$ and 0.01 W/V% of BSA was prepared, (hereinafter, this solution is referred to as [Solution-D"]).

(e) Preparation of a series of diluted solutions (1) Peptide M [obtained in Preparative Example C-5 of Preparation of peptide] was dissolved in 0.1M-sodium phosphate buffer solution (pH-6.5) containing 0.9 W/V% of NaCl and 0.05 W/V% of BSA to prepare a solution having the concentration of 5 micrograms/liter of Peptide M. Then said solution was diluted with Solution-D" as mentioned above to prepare a series of diluted solutions having concentrations of 500, 250, 125, 62.5, 31.25, 15.6, 7.8, 3.9, 1.95, 0.925, 0.463 and 0 ng/ml of Peptide M.

(2) By using human interferon-β (prepared by Tokyo Metropolitan Institute of Medical Science), and method similar to that described in (1) as above, a series of diluted solutions of human interferon-β were prepared. The concentrations of the series of diluted solutions are $2 \times 10^6$, $1 \times 10^6$, $0.5 \times 10^6$, $0.25 \times 10^6$, $0.125 \times 10^6$, $0.063 \times 10^6$, $0.031 \times 10^6$, $0.016 \times 16^6$ and 0 U/ml of human interferon-β.

(f) Determination of polarization degree (P value)

To 0.2 ml of each of the diluted solution prepared in (e)-(1) was added 0.05 ml of Solution-A", 0.1 ml of Solution-C" and 0.65 ml of Solution-D" to prepare a sample solution of Peptide M.

Similarly, a reference sample solution of Peptide M was prepared by using 0.05 ml of Solution-B" in place of Solution A".

Similar to the above, a series of diluted sample solutions of human interferon-β and a series of diluted reference sample solutions thereof were prepared from the series of diluted solutions as described in (e)-(2).

Further, a sample solution of antibody for blank test was prepared by mixing 0.05 ml of Solution-A" with 0.95 ml of Solution-D", and a reference sample solution of antibody for blank test was prepared by mixing 0.05 ml of Solution-B" with 0.95 ml of Solution-D".

Each of these sample solutions and reference sample solutions were incubated at 4° C. for 12 hours, then the polarized light in the fluorescence was determined by an apparatus for measuring fluorescence polarization intensity. The polarization degree (P value) of each of the series of diluted sample solutions was calculated by the following formula.

$$P = \frac{(I_{VS} - I_{VR}) - (I_{HS} - I_{HR})}{(I_{VS} - I_{VR}) + (I_{HS} - I_{HR})} \times 100 \, (\%)$$

[wherein $I_{VS}$: the strength of vertical polarized fluorescence of the sample $I_{HF}$: the strength of horizontal polarized fluorescence of the sample $I_{VR}$: the strength of vertical polarized fluoresence of the reference sample $I_{HR}$: the strength of horizontal polarized fluorescence of the reference sample].

Figure 9:
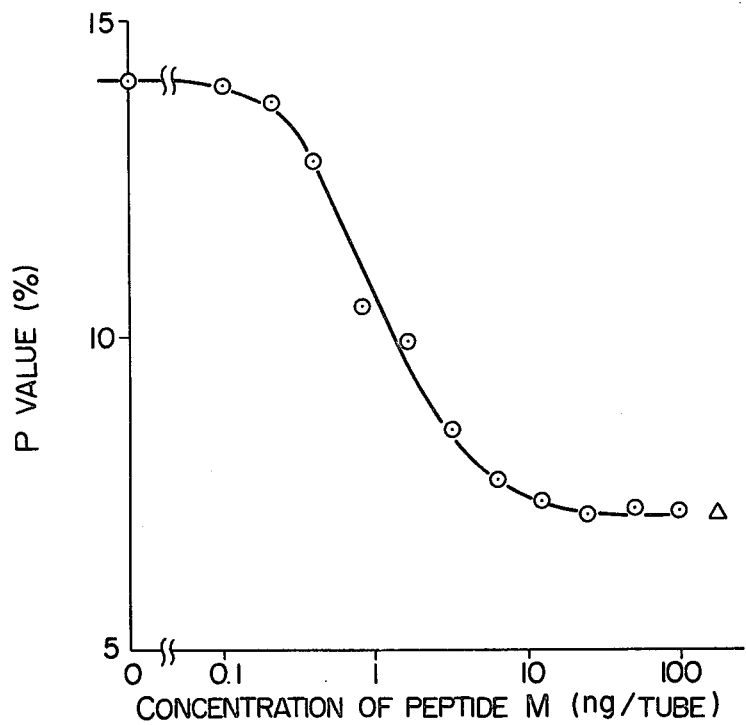
Figure 10:
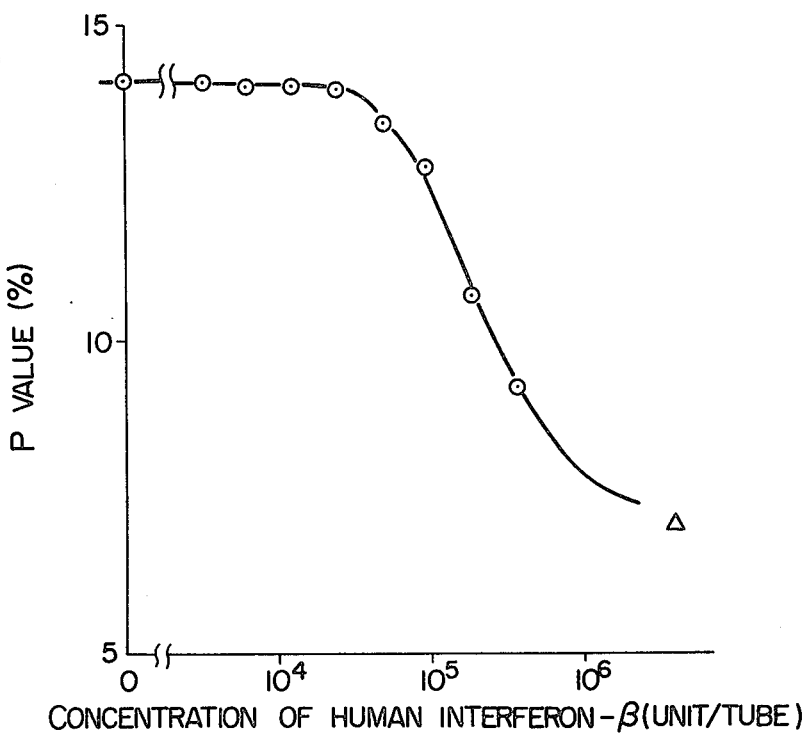

The results are shown in FIG. 9, and FIG. 10. From the FIG. 9, and FIG. 10 the concentration corresponding to a half of the change of P value is 1 ng/Tube in Peptide M, and is $2.1 \times 10^5$ U/Tube in human interferon-$\beta$, and the ratio of these values that 210 U/pg was obtained as the cross matching ratio.

Similarly, the P values were determined in sample solutions of human interferon-$\beta$ of unknown concentration, the potencies of the interferons were assayed from FIGS. 9 and 10.

[Preparation of immobilized antibodies]

PREPARATIVE EXAMPLE 1

(a) 0.74 Milliliter of Antibody $\beta$-V [obtained in Preparative Example 23 of Preparation of Preparation of antibody] was dissolved in 2.26 ml of distilled water, then 3 ml of a saturated ammonium sulfate aqueous solution was added thereto and the mixture was allowed to stand at 4° C. for 3 hours. Then 3 ml of distilled water was added to the said mixture, and allowed to stand at 4° C. for 3 hours. Next, this mixture was subjected to a centrifugal separation (3,500 rpm) at 4° C. for 15 minutes, the precipitate obtained was dissolved in distilled water to obtain 8 ml of an aqueous solution of the antibody ($OD_{280}=1.157$). The solution of the antibody was dialyzed with distilled water in three times, and was further dialyzed with 0.1M-sodium bicarbonate aqueous solution, containing 0.5M-sodium chloride, to obtain 7 ml of the antibody aqueous solution ($OD_{280}=0.923$).

(b) 1 Gram of dried cyanogen bromide-activated Sepharose 4B was washed with 200 ml of 1 mM-hydrochloric acid aqueous solution, then 30 ml of 0.1M-sodium bicarbonate aqueous solution (pH=8.4), containing 0.5M-sodium chloride, and 7 ml of the above-mentioned dialyzed antibody solution were added to the washed Sepharose 4B and inclubated at a room temperature for 2 hours. The mixture was filtered by a glass filter, the gel was dissolved in 40 ml of 1M-monoethanolamine-cl (pH=8.36), and was incubated at a room temperature for 2 hours. This solution was washed with 0.1M-acetate buffer solution, (pH=4.0), containing 0.5M-sodium chloride circulately, then washed with 0.1M-borate buffer solution (pH=8.4), contining 0.5M-sodium chloride in 4 times. By suspending in a physiological saline solution, there is obtained an immobilized product of human interferon-$\beta$ antibody-Sepharose 4B. From the fact that 35 ml of the filtrated obtained from filtration by a glass filter shown $OD_{280}=0.004$, it was confirmed that the most of the antibody is immobilized on Sepharose 4B.

PREPARATIVE EXAMPLE 2

(a) 0.74 Milliliter of Antibody $\beta$-I [obtained in Preparative Example 19 of Preparation of antibody] was dissolved in 2.26 ml of distilled water, then 3 ml of a saturated ammonium sulfate aqueous solution was added thereto and the mixture was allowed to stand at 4° C. for 3 hours. Then 3 ml of distilled water was added to the said mixture, allowed to stand at 5° C. for 3 hours. This mixture was subjected to a centrifugal separation (3,500 rpm) at 4° C. for 15 minutes, the precipitate obtained was dissolved in distilled water to obtain 8 ml of an aqueous solution of the antibody ($OD_{280}=1.154$). The solution of the antibody was dialyzed with distilled water in three times, and was further dialyzed with 0.1M-sodium bicarbonate aqueous solution, (pH=8.4) containing 0.5M-sodium chloride, to obtain 7 ml of the antibody aqueous solution ($OD_{280}=0.921$).

(b) 1 Gram of dried cyanogen bromide-activated Sepharose 4B was washed with 200 ml of 1 mM-hydrochloric acid aqueous solution, then to this washed Sepharose 4B was added 30 ml of 0.1M-sodium bicarbonate aqueous solution, containing 0.5M-sodium chloride, and 7 ml of the above-mentioned dialyzed antibody solution, then this mixture was incubated at a room temperature for 2 hours. After the incubation, the mixture was filtered by a glass filter, the gel obtained was dissolved in 40 ml of 1M-monoethanolamine-cl (pH=9.36), and was incubated at a room temperature for 2 hours. The solution was washed circulately with 0.1M-acetate buffer solution (pH=4.0), containing 0.5M-sodium chloride then washed with 0.1M-borate buffer solution, containing 0.5M-sodium chloride in 4 times. By suspending in a physiological saline solution, there is obtained an adsorbed product of human interferon-$\beta$ antibody being immobilized on Sepharose 4B. From the fact that 35 ml of the filtrate obtained from filtration by a glass filter shown $OD_{280}=0.004$, it was confirmed that the most of the antibody is being immobilized on Sepharose 4B.

PREPARATIVE EXAMPLE 3

(a) 0.74 Milliliter of Antibody $\beta$-II [obtained in Preparative Example 20 of Preparation of antibody] was dissolved in 2.26 ml of distilled water, then 3 ml of a saturated ammonium sulfate aqueous solution was added thereto and the resulting mixture was allowed to stand at 4° C. for 3 hours. Then 3 ml of distilled water was added to the said mixture, and allowed to stand at 4° C. for 3 hours. The resulting mixture was subjected to a centrifugal separation (3,500 rpm) at 4° C. for 15 minutes, the precipitate obtained was dissolved in distilled water to obtain 8 ml of an aqueous solution of the antibody ($OD_{280}=1.155$). Next, the solution of the antibody was dialyzed with distilled water in three times and was further dialyzed with 0.1M-sodium bicarbonate aqueous solution (pH=8.4), containing 0.5M-sodium chloride, to obtain 7 ml of the antibody aqueous solution ($OD_{280}=0.921$).

(b) 1 Gram of dried cyanogen bromide-activated Sepharose 4B was washed with 200 ml of 1 mM-hydrochloric acid aqueous solution, then to the washed Sepharose 4B was added 30 ml of 0.1M-sodium bicarbonate aqueous solution, containing 0.5M-sodium chloride, and 7 ml of the above-mentioned dialyzed antibody solution, then the resulting mixture was incubated at a room temperature for 2 hours. After the incubation, the mixture was filtered by a glass filter, the gel obtained was dissolved in 40 ml of 1M-monoethanolamine-cl (pH 8.36), and was incubated at a room temperature for two hours. This solution was washed circulately with 0.1M-acetate buffer solution (pH=4.0), containing 0.5M-sodium chloride next washed further with 0.1M-borate buffer solution, containing 0.5M-sodium chloride in 4 times. By suspending in a physiological saline solution, there is obtained an adsorbed product of human interferon-$\beta$ antibody being immobilized on Sepharose 4B. From the fact that 35 ml of the filtrate obtained from filtration of the adsorbed product by a glass filter shown $OD_{280}=0.004$, it was confirmed that the most of the antibody is being immobilized on Sepharose 4B.

PREPARATIVE EXAMPLE 4

(a) 0.74 Milliliter of Antibody $\beta$-III [obtained in Preparative Example 21 of Preparation of antibody] was dissolved in 2.26 ml of distilled water, then 3 ml of saturated ammonium sulfate aqueous solution was added thereto and the resulting mixture was allowed to stand at 4° C. for 3 hours. Then 3 ml of distilled water was added to said mixture, and allowed to stand at 4° C. for 3 hours. The resulting mixture was subjected to a centrifugal separation (3,500 rpm) at 4° C. for 15 minutes, the precipitate obtained was dissolved in distilled water to obtain 8 ml of an aqueous solution of the antibody ($OD_{280}=1.156$). Next, the solution of the antibody was dialyzed with distilled water 3 times, and was further dialyzed with 0.1M-sodium bicarbonate aqueous solution (pH=8.4), containing 0.5M-sodium chloride, to obtain 7 ml of the antibody aqueous solution ($OD_{280}=0.922$).

(b) 1 Gram of dried cyanogen bromide-activated Sepharose 4B was washed with 200 ml of 1 mM-hydrochloric acid aqueous solution, then to this washed Sepharose 4B was added 30 ml of 0.1M-sodium bicarbonate aqueous solution, contianing 0.5M-sodium chloride, and 7 ml of the above-mentioned dialyzed antibody solution, then the resulting mixture was incubated at a room temperature for 2 hours. After the incubation, the mixture was filtered by a glass filter, the gel obtained was dissolved in 40 ml of 1M-monoethanolamine-cl (pH=8.36), and was incubated at a room temperatxre for 2 hours. This solution was washed circulately with 0.1M-acetate buffer solution (pH=4.0), containing 0.5M-sodium chloride, next washed further with 0.1M-borate buffer solution, containing 0.5M-sodium chloride 4 times. By suspending in a physiological saline solution, there is obtained an adsorbed product of human interferon-$\beta$ antibody being immobilized on Sepharose 4B. From the fact that 35 ml of the filtrate obtained from filtration of the adsorbed product by a glass filter shown $OD_{280}=0.004$, it was confirmed that the most of the antibody is being immobilized on Sepharose 4B.

PREPARATIVE EXAMPLE 5

(a) 0.74 Milliliter of Antibody $\beta$-IV [obtained in Preparative Example 22 of Preparation of antibody] was dissolved in 2.26 ml of distilled water, then 3 ml of a saturated ammonium sulfate aqueous solution was added the-eto and the resulting mixture was allowed to stand at 4° C. for 3 hours. Then 3 ml of distilled water was added to said mixture, and allowed to stand at 4° C. for 3 hours. The resulting mixture was subjected to a centrifugal separation (3,500 rpm) at 4° C. for 15 minutes, the precipitate obtained was dissolved in distilled water to obtain 8 ml of an aqueous solution of the antibody ($OD_{280}=1.153$). Next, the solution of the antibody was dialyzed with distilled water 3 times, and was further dialyzed with 0.1M-sodium bicarbonate aqueous solution (pH=8.4), containing 0.5M-sodium chloride, to obtain 7 ml of the antibody aqueous solution ($OD_{280}=0.920$).

(b) 1 Gram of dried cyanogen bromide-activated Sepharose 4B was washed with 200 ml of 1-mM-hydrochloric acid aqueous solution, then to this washed Sepharose 4B was added 30 ml of 0.1M-sodium bicarbonate aqueous solution, containing 0.5M-sodium chloride, and 7 ml of the above-mentioned dialyzed antibody solution, then the resulting mixture was incubated at a room temperature for 2 hours. After the incubation, the mixture was filtered by a glass filter, the gel obtained was dissolved in 40 ml of 1M-monoethanolamine-cl (pH=8.36), and was incubated at a room temperature for 2 hours. This solution was washed circulately with 0.1M-acetate buffer solution (pH=4.0), containing 0.5M-sodium chloride, next washed further with 0.1M-borate buffer solution, containing 0.5M-sodium chloride 4 times. By suspending in a physiological saline solution, there was obtained an adsorbed product of human interferon-$\beta$ antibody being immobilized on Sepharose 4B. From the fact that, 35 ml of the filtrate obtained from filtration of the adsorbed product by a glass filter shown $OD_{280}=0.004$, it was confirmed that the most of the antibody is being immobilized on Sepharose 4B.

PREPARATIVE EXAMPLE 6

(a) 0.74 Milliliter of Antibody $\beta$-VI [obtained in Preparative Example 24 of Preparation of antibody] was dissolved in 2.26 ml of distilled water, then 3 ml of a saturated ammonium sulfate aqueous solution was added thereto and the resulting mixture was allowed to stand at 4° C. for 3 hours. Then 3 ml of distilled water was added to said mixture, and allowed to stand at 4° C. for 3 hours. The resulting mixture was subjected to a centrifugal separation (3,500 rpm) at 4° C. for 15 minutes, the precipitate obtained was dissolved in distilled waster to obtain 8 ml of an aqueous solution of the antibody ($OD_{280}=1.158$). Next, the solution of the antibody was dialyzed with distilled water 3 times, and was further dialyzed with 0.1M-sodium bicarbonate aqueous solution (pH=8.4), containing 0.5M-sodium chloride, to obtain 7 ml of the antibody aqueous solution ($OC_{280}=0.924$).

(b) 1 Gram of dried cyanogen bromide-activated Sepharose 4B was washed with 200 ml of 1 mM-hydrochloric acid aqueous solution, then to this washed Sepharose 4B was added 30 ml of 0.1M-sodium bicarbonate aqueous solution, containing 0.5M-sodium chloride, and 7 ml of the above-mentioned dialyzes antibody solution, then the resulting mixture was incubated at a room temperature for 2 hours. After the incubation, the mixture was filtered by a glass filter, the gel obtained was dissolved in 40 ml of 1M-monoethanolamine-cl (pH=8.36), and was incubated at a room temperature for 2 hours. Then this solution was washed circulately with 0.1M-acetate buffer solution (pH=4.0), containing 0.5M-sodium chloride, next, washed further with 0.1M-borate buffer solution, containing 0.5M-sodium chloride, 4 times. By suspending in a physiological saline solution, there was obtained an adsorbed product of human interferon-β antibody being immobilized on Sepharose 4B. From the fact that 35 ml of the filtrated obtained from the filtration of the adsorbed product by using a glass filter shown $OD_{280}=0.004$, it was confirmed that the most of the antibody is being immobilized on Sepharose 4B.

PREPARATIVE EXAMPLE 7

A piece of filter paper (Toyo Filter Paper No. 2, manufactured by Toyo Filter Paper Co., Ltd.) was cut into small pieces of papaer having 0.5 cm×0.5 cm, and weighed about 1 g of them. Said small pieces of filter paper (cellulose) were put into 100 ml of an aqueous solution containing 1 g of cyanogen bromide and kept the pH of the mixture to about pH 11.0 to 11.5 by adding a solution of sodium hydroxide to activate the cellulose at a room temperature for 6 to 8 minutes. After completion of the activation, the reaction mixture was subjected to filtration to remove the reaction liquid, the resulting solid matter was washed several times with ice-cooled 0.5M-sodium bicarbonate buffer solution (pH=8.4) containing 0.5M-sodium chloride, then the washed solid matter was suspended in the same buffer solution. To this suspension was added the antibody aqueous solution ($OD_{280}=0.918$) obtained by a method similar to that described in the above-mentioned Preparative Example 1 (a), then the resulting mixture was treated by a method similar to that described in the above-mentioned Preparative Example 1 (b) to obtain an adsorbed product of human interferon-β being immobilized on cellulose. From the fact that the filtrate obtained through a glass filter show $OD_{280}=0.004$, it was confirmed that the most of the antibody is immobilized on the cellulose.

PREPARATIVE EXAMPLE 8

1 Gram of a crosslinked dextran (Sephadex G-25) was suspended in 10 ml of water to prepare a crosslinked dextran suspended aqueous suspension. To this suspension was added 10 ml of 2M-sodium bicarbonate aqueous solution and was stirred smoothly. Then the szirring speed was increased and 500 microliters of an acetonitrile solution of cyanogen bromide (2 g/ml) was added in one time and stirred vigorously for 1 to 2 minutes, and the reaction mixture was filtered to remove the reaction liquid through a glass filter. The solid matter obtained was washed several times with 0.1M-sodium bicarbonate buffer solution (pH 8.4), containing 0.5M-sodium chloride. After washing, the solid material, was suspended in the same buffer solution, and the antibody aqueous solution ($OD_{280}=0.921$) [obtained in Preparative Example 1 (a) as mentioned above] was added thereto and was treated by a method similar to that described in the above-mentioned Preparative Example 1 (b) to obtain an adsorbed product of human interferon-β being immobilized on crosslinked dextran. From the fact that the filtrate obtained through a glass filter show $OD_{280}=0.004$, it was confirmed that the most of the antibody is immobilized on the crosslinked dextran.

PREPARATIVE EXAMPLE 9

1 Milliliter of Antibody β-N-IV [obtained in Preparative Example 4 of Preparation of antibody] was dissolved in 2.0 ml of distilled water, then 3 ml of a saturated ammonium sulfate aqueous solution was added thereto and the resulting mixture was allowed to stand at 4° C. for 3 hours. Then 3 ml of distilled water was added to said mixture, and allowed to stand at 4° C. for 3 hours. The resulting mixture was subjected to a centrifugal separation (3,500 rpm) at 4° C. for 15 minutes, the precipitate was dissolved in distilled water to obtain 10 ml of an aqueous solution of the antibody ($OD_{280}=1.538$). Next, said solution of the antibody was dialyzed with distilled water 3 times, and was further dialyzed with 0.1M-sodium bicarbonate aqueous solution (pH 8.4), containing 0.5M-sodium chloride, to obtain 10 ml of the antibody aqueous solution ($OD_{280}=1.501$).

(b) 1 Gram of dried cyanogen bromide-activated Sepharose 4B was washed with 200 ml of 1 mM-hydrochloric acid aqueous solution, then to this washed Sepharose 4B was added 30 ml of 0.1M-sodium bicarbonate aqueous solution, containing 0.5M-sodium chloride, and 7 ml of the above-mentioned dialyzed antibody solution, then the resulting mixture was incubated at a room temperature for 2 hours. After the incubation, the mixture was filtered by a glass filter, the gel obtained was dissolved in 40 ml of 1M-monoethanolamine-cl (pH=8.36), and was incubated at a room temperatxre for 2 hours. This solution was washed circulately with 0.1M-acetate buffer solution (pH=4.0), containing 0.5M-sodium chloride, next was washed further 4 times with 0.1M-borate buffer solution, containing 0.5M-sodium chloride. By suspending in a physiological saline solution, there was obtained an adsorbed product of human interferon-α antibody being immobilized on Sepharose 4B. From the fact that 35 ml of the filtrate obtained from filtration of the adsorbed product by a glass filter shown $OD_{280}=0.004$, it was confirmed that the most of the antibody was being immobilized on Sepharose 4B.

PREPARATIVE EXAMPLE 10

By using Antibody α-N-I, to α-N-III and Antibody α-N-V to Antibody α-N-X [obtained in Preparative Examples 1 to 3 and 5 to 10 of Preparation of antibody] in place of Antibody α-N-IV as used in the above-mentioned Preparative Example 9, by using a method similar to that described in Preparative Example 9, respectively, the following antibody aqueous solutions were obtained:

| Antibody aqueous solution | Antibody used | $OD_{280}$ |
|---|---|---|
| A | α-N-I | 1.501 |
| B | α-N-II | 1.522 |
| C | α-N-III | 1.512 |
| D | α-N-V | 1.532 |
| E | α-N-VI | 1.515 |
| F | α-N-VII | 1.526 |
| G | α-N-VIII | 1.513 |
| H | α-N-IX | 1.527 |
| I | α-N-X | 1.521 |

(b) By using each of the antibody aqueous solutions obtained in the above-mentioned step (a), and by using a method similar to that described in the above-mentioned Preparative Example 9-(b), corresponding adsorbed products of human interferon-β being immobilized on Sepharose 4B were obtained respectively. From the facts that each of the filtrates obtained from filtrations through glass filter shown about

PREPARATIVE EXAMPLE 11

A piece of filter paper (Toyo Filter Paper No. 2, manufactured by Toyo Filter Paper Co., Ltd.) was cut into small pieces of paper having the size of 0.5 cm×0.5 cm, and was weighed about 1 g of them. Said small pieces of filter paper (cellulose) were put into 100 ml of an aqueous solution containing 1 g of cyanogen bromide and kept the pH of the mixture to about pH 11.0 to 11.5 by adding a solution of sodium hydroxide, followed by activated the cellulose at a room temperature for 6 to 8 minutes. After completion of the activation, the reaction mixture was subjected to filtration to remove the reaction liquid. The resulting solid matter was washed several times with ice-cooled 0.5M-sodium bicarbonate buffer solution (pH=8.4), containing 0.5M-sodium chloride, then the washed solid matter was suspended in the same buffer solution. To this suspension was added the antibody aqueous solution ($OD_{280}=1.502$) obtained by a method similar to that described in the above-mentioned Preparative Example 9 (a), then the resulting mixture was treated by a method similar to that described in the above-mentioned Preparative Example 9 (b) to obtain an adsorbed product of the human interferon-α antibody being immobilized on the cellulose. From the fact that the filtrate obtained from the filtration of the adsorbed product by using a glass filter show $OD_{280}=0.004$, it was confirmed that the most of the antibody is being immobilized on the cellulose.

PREPARATIVE EXAMPLE 12

1 Gram of a crosslinked dextran (Sephadex G-25) was suspended in 10 ml of water to prepare a cro crosslinked dextran suspended aqueous suspension. To this suspension was added 10 ml of 2M-sodium bicarbonate aqueous solution and was stirred smoothly. Then the stirring speed was increased and 500 microliters of an acetonitrile solution of cyanogen bromide (2 g/ml) was added in one time and stirred vigorously for 1 to 2 minutes, and the reaction mixture was filtrated to remove the reaction liquid through a glass filter. The solid matter obtained was washed several time with 0.1M-sodium bicarbonate buffer solution (pH=8.4), containing 0.5M-sodium chloride. After washing, the solid matter was suspended in the same buffer solution, and the antibody aqueous solution ($OC_{280}=1.511$) [obtained in Preparative Example 9 (a) as mentioned above] was added thereto and was treated by a method similar to that described in the above-mentioned Preparative Example 9 (b) to obtain an adsorbed product of human interferon-α antibody being immobilized on the crosslinked dextran. From the fact that the filtrate obtained from the filtration of the adsorbed product by using a glass filter shows $OD_{280}=0.004$, it was confirmed that the most of the antibody is being immobilized on the cellulose.

PREPARATIVE EXAMPLE 13

(a) 1.0 Milliliter of Antibody α-C-VIII [obtained in Preparative Example 17 of Preparation of antibody] was dissolved in 2.0 ml of distilled water, then 3 ml of a saturated ammonium sulfate aqueous solution was added thereto and the resulting mixture was allowed to stand at 4° C. for 3 hours. Then 3 ml of distilled water was added to said mixture, and was allowed to stand at 4° C. for 3 hours. The resulting mixture was subjected to a centrifugal separation (3,500 rpm) at 4° C. for 15 minutes, the precipitate obtained was dissolved in distilled water to obtain 10 ml of the antibody aqueous solutio-($OD_{280}=1.526$). Next, the solution of the antibody was dialyzed 3 times with distilled water, and was further dialyzed with 0.1M-sodium bicarbonate aqueous solution (pH=8.4), containing 0.5M-sodium chloride, to obtain 10 ml of the antibody aqueous solution ($OD_{280}=1.511$).

(b) 1 Gram of dried cyanogen bromide-activated Sephrose 4B was washed with 200 ml of 1 mM-hydrochloric acid, then to this washed Sepharose 4B was added 30 ml of 0.1M-sodium bicarbonate aqueous solution, containing 0.5M-sodium chloride, and 7 ml of the above-mentioned dialyzed antibody solution, then the resulting mixture was incubated at a room temperature for 2 hours. After the incubation, the mixture was filtered by a glass filter, the gel obtained was dissolved in 40 ml of 1M-monoethanolamine-CL (pH=8.36), and was incubated at a room temperature for 2 hours. This solution was washed circulately with 0.1M-acetate buffer solution (pH=4.0), containing 0.5M-sodium chloride, next was washed further with 0.1M-borate buffer solution, containing 0.5M-sodium chloride. By suspending in a physiological saline solution, there was obtained an adsorbed product of human interferon-α antibody being immobilized on Sepharose 4B. From the fact that 35 ml of the filtrate obtained from the filtration of the adsorbed product by a glass filter shown $OD_{280}=0.004$, it was confirmed that the most of the antibody was being immobized on Sepharose 4B.

PREPARATIVE EXAMPLE 14

(a) By using Antibody α-C-I to Antibody α-C-VII and Antibody α-C-IX to Antibody α-C-XIII [obtained in Preparative Examples 11 to 18 of Preparation of antibody] in place of using Antibody α-C-VIII as used in the above-mentioned Preparative Example 13, respectively, the following antibody aqueous solutions were obtained:

| Antibody aqueous solution | Antibody used | $OD_{280}$ |
| --- | --- | --- |
| J | α-C-III | 1.511 |
| K | α-C-I | 1.502 |
| L | α-C-II | 1.512 |
| M | α-C-IV | 1.506 |
| N | α-C-V | 1.513 |
| O | α-C-VI | 1.507 |
| P | α-C-VII | 1.513 |
| Q | α-C-IX | 1.502 |
| R | α-C-X | 1.501 |
| S | α-C-XI | 1.509 |
| T | α-C-XII | 1.507 |
| U | α-C-XIII | 1.506 |

(b) By using each of the antibody aqueous solutions obtained in the above-mentioned step (a), and by using a method similar to that described in the above-mentioned Preparative Example 13-(b), corresponding adsorbed products of human interferon-α being immobilized on Sepharose 4B were obtained respectively. From the facts that each of the filtrates obtained from the filtrations through glass filter show about $OD_{280}=0.004$, it was confirmed that the most of the antibodies in the respective products were being immobilized on Sepharose 4B.

PREPARATIVE EXAMPLE 15

A piece of filter paper (Toyo Filter Paper No. 2, manufactured by Toyo Filter Paper Co., Ltd.) as cut into small pieces of paper having the size of 0.5 cm×0.5 cm, and was weighed about 1 g of them. Said small pieces of filter paper (cellulose) were put into 100 ml of an aqueous solutoin containing 1 g of cyanogen bromide and kept the pH of the mixture to about pH 11.0 to 11.5 by adding a solution of sodium hydroxide, to activate the cellulose at a room temperature for 6 to 8 minutes. After completion of the activation, the reaction mixture was filtrated to remove the reaction liquid, the resulting solid metter was washed several times with ice-cooled 0.5M-sodium bicarbonate buffer solution (pH=8.4), containing 0.5M-sodium chloride, then the washed solid matter was suspended in the same buffer solution. To this suspension was added the antibody aqueous solution ($OD_{280}=1.502$) [obtained by a method similar to that described in the above-mentioned Preparative Example 13-(a)] then the resulting mixture was treated by a method similar to that described in the above-mentioned Preparative Example 13 (b) to obtain an adsorbed product of the human interferon-α antibody being immobilized on the cellulose. From the fact that the filtrate obtained from the filtration of the adsorbed product by using a glass filter shown $OD_{280}=0.004$, it was confirmed that the most of the antibody is being immobilized on the cellulose.

PREPARATIVE EXAMPLE 16

1 Gram of a crosslinked dextran (Sephadex G-25) was suspended in 10 ml of water to prepare a crosslinked dextran suspended aqeuous suspension. To this suspension was added 10 ml of 2M-sodium bicarbonate aqueous solution and was stirred smoothly. Then the stirring speed was increased and 500 microliters of an acetonitrile solution of cyanogen bromide (2 g/ml) was added in one time and stirred vigorously for 1 to 2 minutes, and the reaction mixture was filtrated to remove the reaction liquid through a glass filter. The solid matter obtained was washed several times with 0.1M-sodium bicarbonate buffer solution (pH-8.4), containing 0.5M-sodium chloride. After washing, the solid matter was suspended in the same buffer solution, and the antibody aqueous solution ($OD_{280}=1.505$) [obtained by a method similar to that in Preparative Example 13 (a) as mentioned above] was added thereto and was treated by a method similar to that described in the above-mentioned Preparative Example 13 (b) to obtain an adsorbed product of human interferon-α antibody being immobilized on the crosslinked dextran. From the fact that the filtrate obtained from the filtration of the adsorbed product by using a glass filter shows $OD_{280}=0.004$, it was confirmed that the most of the antibody is being immobilized on the crosslinked dextran.

[Purification of human interferons]

(1) 0.5 Milliliter (5.9 mg of proteins) of human interferon-β ($OD_{280}=11.8$, prepared by Tokyo Metropolitan Institute of Medical Science) was dissolved in physiological saline solution, then this solution was filled in an affinity chromatography using the adsorbed product of human interferon-β antibody immobilized on Sepharose 4B [obtained in Preparative Example 1 (b) of Preparation of immobilized antibodies], and was eluted with 0.1M-phosphate buffer solution (pH=7.4), containing 0.15M-sodium chloride. When the eluate become $OD_{280}=0.0002$ the absorbed product was eluted with 0.5M-acetic acid buffer solution (pH=2.5), containing 0.5M-sodium chloride to isolate the purified human interferon-β from the adsorbed product.

Before the treatment by affinity chromatography, the human interferon-β shows the converted OD value=5.9 [a value obtained at 1 mg of proteins when $OD_{280}=1$], and also shows activity of $1.5\times10^6$ Unit/ml, the concentration of 13,240 pg/ml, in immunity reaction of human interferon-β, on the contrary after the treatment by affinity chromatography, the converted OD value of the human interferon-β was 0.059, and also shown the activity of $1.37\times10^6$ Unit/ml and the concentration of 12,050 pg/ml in immunity reaction of human interferon-β. Therefore, the specific activity before the treatment by affinity chromatography was $2.54\times10^5$ Unit/mg, while the specific activity after the treatment by affinity chromatography was $2.32\times10^7$ Unit/mg, which is a significant value of 91.3 times in the specific activity. As can be seen from the results obtained by using the adsorbed product (mmobilized antibody on the carrier) human interferon-β can be purified as 91 times purity as possible and a yield thereof can be also achieved quantitatively.

By using each of the immobilized antibodies [obtained in Preparative Examples 2 to 8 of Preparation of immobilized antibody], according to the present invention, excellent performances in isolating and purification of human interferons were shown through the treatment by affinity chromatography.

(2) 0.5 Milliliter (10.1 mg of proteins) of human interferon-α ($OD_{280}=20.2$, prepared by Hayashibara Biochemical Research Laboratory) was dissolved in physiological saline solution, then this solution was filled in an affinity chromatography using the adsorbed product of human interferon-α antibody immobilized on Sepharose 4B [obtained in Preparative Example 9 (b) of Preparation of immobilized antibodies], and was eluted with 0.1-phosphate buffer solution (pH=7.4), containing 0.15M-sodium chloride. When the eluate become $OD_{280}=0.002$ or lower, then the adsorbed product was eluted with 0.5M-acetic acid buffer solution (pH=2.5), containing 0.5M-sodium chloride to isolate the purified human interferon-α from the adsorbed product.

Before the treatment by using the affinity chromatography, the human interferon-α shows the converted OD value=10.1 [a value obtained at 1 mg of proteins when $OD_{280}=1$], and also shows the activity of $1\times10^6$ Unit/ml and the concentration of 6900 pg/ml, in an immunity reaction of human interferon-α, on the contrary after the treatment by using the affinity chromatography, the converted OD value of the human interferon-α was 0.080, and also shown the activity of $8\times10^5$ Unit/ml and the concentration of 55,000 pg/ml in immunity reaction of human interferon-α. Therefore, the specific activity before the treatment by using affinity chromatography was $5.9\times10^4$ Unit/mg, while the specific activity after the treatment by using affinity chromatography was $1\times10^7$ Unit/mg, which is a significant value of 169 times in the specific activity. As can be seen from the results obtained by using the adsorbed product (immobilized antibody on the carrier) human interferon-α can be purified as 169 times purity as possible and the yield thereof can be also achieved quantitatively.

By using each of the immobilized antibodies obtained in Preparative Examples 10 to 12 of Preparation of immobilized antibodym according to the present invention, excellent performances in isolating and purification of human interferons were shown through the treatment by affinity chromatography.

(3) 0.5 Molliliter (10.1 mg of proteins) of human interferon-α ($OD_{280}=20.2$, prepared by National Institute of Health) was dissolved in physiological saline solution, then this solution was filled in an affinity chromatography using the adsorbed product of human interferon-α antibody immobilized on Sepharose 4B [obtained in Preparative Example 13 (b) of Preparation of immobilized antibodies], and was eluted with 0.1M-phosphate buffer solution (pH=7.4), containing 0.15M-sodium chloride. When the eluate become $OD_{280}=0.002$ or lower, then the adsorbed product was eluted with 0.5M-acetic acid buffer solution (pH=2.5), containing 0.5M-sodium chloride to isolate the purified human interferon-α from the adsorbed product.

Before the treatment by using the affinity chromatography, the human interferon-α shows the converted OD value=10.1 [a value obtained at 1 mg of proteins when $OD_{280}=1$], and also shows activity of $x \times 10^6$ Unit/ml and the concentration of 23,000 pg/ml in an immunity reaction of human interferon-α, on the contrary after the treatment by using the affinity chromatography, the converted OD value of the human interferon-α was OD=0.060, and also shows the activity of $8.2 \times 10^5$ Unit/ml and the concentration of in an immunity reaction of human interferon-α. Therefore, the specific activity before the treatment by using an affinity chromatography was $9.9 \times 10^4$ Unit/mg, while the specific activity after the treatment by using the affinity chromatography was $1.37 \times 10^7$ Unit/mg, which is a significant value of 138 times higher in the specific activity. As can be seen from the results obtained by using the adsorbed product (mmobilized antibody on the carrier) human interferon-α can be purified as 138 times higher purity as possible and the yield there of a can also be achieved quantitatively.

By using each of the immobilized antibodies obtained in Preparative Examples 14 to 16 of Preparation of immobilized antibody, according to the present invention, excellent performances in isolating and purification of human interferons were shown through the treatment by using the affinity chromatography.

What is claimed is:

1. A human interferon antibody obtained by collecting an antibody being produced in a mammalian body after administering, to the mammal, a human interferon antigen prepared by reacting a human interferon-related peptide selected from the group consisting of a peptide represented by the formula:

$$R^1\text{-Leu-Ile-Leu-Leu-Ala-Gln-OH} \qquad (1)$$

wherein $R^1$ is selected from the group consisting of a hydrogen atom and group of the formula H-Thr-His-Ser-Leu-Gly-Asn-Arg-Arg-Ala-; a peptide represented by the formula:

$$R^2\text{-Glu-Ser-Leu-Arg-Ser-Lys-Glu-OH} \qquad (2)$$

wherein $R^2$ is selected from the group consisting of a hydrogen atom, a group of the formula H-Thr-Asn-Leu-Gln-, a group of the formula H-Ser-Leu-Ser-Thr-Asn-Leu-Gln- and a group of the formula H-Thr-Ser-Leu-Ser-Thr-Asn-Leu-Gln-; and a peptide represented by the formula:

$$R^3\text{-Leu-Gln-Arg-Ser-Ser-OH} \qquad (3)$$

wherein $R^3$ is selected from the group consisting of a hydrogen atom, a group of the formula H-Phe-, a group of the formula H-Leu-Gly-Phe- and a group of the formula H-Tyr-Asn-Leu-Leu-Gly-Phe-, as a hapten, with a carrier in the presence of a hapten-carrier binding agent.

2. The human interferon antibody according to claim 1, wherein the human interferon antigen is prepared by reacting a human interferon-related peptide of the general formula (1), as a hapten, with a carrier in the presence of a hapten-carrier binding agent.

3. The human interferon antibody according to claim 1, wherein the human interferon antigen is prepared by reacting a human interferon-related peptide of the general formula (2), as a hapten, with a carrier in the presence of a hapten-carrier binding agent.

4. The human interferon antibody according to claim 1, wherein the human interferon antigen is prepared by reacting a human interferon-related peptide represented by the general formula (3), as a hapten, with a carrier in the presence of a hapten-carrier binding agent.

5. The human interferon antibody according to claim 2, 3 or 4, wherein the human interferon antigen is prepared by using a carrier selected from the group consisting of an animal serum albumin, an animal serum globulin, an animal thyroglobulin, an animal hemoglobulin, an animal hemocyanin, an ascars-extract, a polylysine, a polyglutamic acid, a lysineglutamic acid copolymer, a lysine-containing copolymer and an ornithine-containing copolymer, and a hapten-carrier binding agent is a carrier selected from the group consisting of an aliphatic dialdehyde, a dimaleimide compound, a maleimidecarboxyl-N-hydroxysuccinimideester compound and carbodiimide.

6. The human interferon antibody according to claim 5, wherein the animal is a mammal selected from the group consisting of a rabbit and a guinea pig.

7. The human interferon antibody according to claim 6, wherein the human interferon antibody being produced in a mammal body is obtained by administering to the mammal, a human interferon antigen by mixing with a Freund's adjuvant.

8. The human interferon antibody according to claim 7, wherein the human interferon antibody being produced in a mammal body is obtained by administering to a rabbit, a human interferon antigen prepared by using a peptide represented by the general formula, H-Ser-Leu-Ser-Thr-Asn-Leu-Gln-Glu-Ser-Leu-Arg-Ser-Lys-Glu-OH as the hapten; glutaraldehyde as the hapten-carrier binding agent; and BSA as the carrier.

9. The human interferon antibody according to claim 7, wherein the human interferon antibody being produced in a mammal body is obtained by administering to a rabbit, a human interferon antigen prepared by using a peptide represented by the general formula, H-Ser-Leu-Ser-Thr-Asn-Leu-Gln-Glu-Ser-Leu-Arg-Ser-lys-Glu-OH as the hapten; DCC as the hapten-carrier binding agent; and BSA as the carrier.

10. A process for preparing a human interferon antibody by collecting an antibody being produced in a mammalian body by administering, to the mammal, a human interferon antigen prepared by reacting a human interferon-derived peptide selected from the group consisting of a peptide represented by the formula:

$$R^1\text{-Leu-Ile-Leu-Leu-Ala-Gln-OH} \tag{1}$$

wherein $R^1$ is selected from the group consisting of a hydrogen atom and group of the formula H-Thr-His-Ser-Leu-Gly-Asn-Arg-Arg-Ala-; a peptide represented by the formula:

$$R^2\text{-Glu-Ser-Leu-Arg-Ser-Lys-Glu-OH} \tag{2}$$

wherein $R^2$ is selected from the group consisting of a hydrogen atom, a group of the formula H-Thr-Asn-Leu-Gln-, a group of the formula H-Ser-Leu-Ser-Thr-Asn-Leu-Gln- and a group of the formula H-Thr-Ser-Leu-Ser-Thr-Asn-Leu-Gln-; and a peptide represented by the formula:

$$R^3\text{-Leu-Gln-Arg-Ser-Ser-OH} \tag{3}$$

wherein $R^3$ is selected from the group consisting of a hydrogen atom, a group of the formula H-Phe-, a group of the formula H-Leu-Gly-Phe- and a group of the formula H-Tyr-Asn-Leu-Leu-Gly-Phe-, as a hapten, with a carrier in the presence of a hapten-carrier binding agent.

* * * * *